US009890382B2

(12) United States Patent
Bentwich et al.

(10) Patent No.: US 9,890,382 B2
(45) Date of Patent: Feb. 13, 2018

(54) NUCLEIC ACID COMPOSITIONS RELATED TO MIR-138-1-3P AND USES THEREOF

(71) Applicant: Rosetta Genomics Ltd., Rehovot (IL)

(72) Inventors: Itzhak Bentwich, Tel Aviv (IL); Amir Avniel, Tel Aviv (IL); Yael Karov, Tel Aviv (IL); Ranit Aharonov, Tel Aviv (IL)

(73) Assignee: ROSETTA GENOMICS LTD., Rehovot (IL)

( * ) Notice: Subject to any disclaimer, the term of this patent is extended or adjusted under 35 U.S.C. 154(b) by 0 days.

(21) Appl. No.: 15/586,783

(22) Filed: May 4, 2017

(65) Prior Publication Data
US 2017/0240894 A1    Aug. 24, 2017

Related U.S. Application Data

(60) Division of application No. 14/756,185, filed on Aug. 13, 2015, now Pat. No. 9,650,679, which is a division of application No. 13/986,516, filed on May 8, 2013, now Pat. No. 9,133,453, which is a division of application No. 12/661,041, filed on Mar. 10, 2010, now Pat. No. 8,461,315, which is a division of application No. 11/130,645, filed on May 16, 2005, now Pat. No. 7,709,616, which is a continuation of application No. PCT/US2005/016986, filed on May 14, 2005, and a continuation-in-part of application No. 10/709,577, filed on May 14, 2004, now Pat. No. 7,687,616, and a continuation-in-part of application No. 10/709,572, filed on May 14, 2004, now Pat. No. 7,888,497.

(60) Provisional application No. 60/666,340, filed on Mar. 30, 2005, provisional application No. 60/665,094, filed on Mar. 25, 2005, provisional application No. 60/662,742, filed on Mar. 17, 2005, provisional application No. 60/593,329, filed on Jan. 6, 2005, provisional application No. 60/593,081, filed on Dec. 8, 2004, provisional application No. 60/522,860, filed on Nov. 15, 2004, provisional application No. 60/522,457, filed on Oct. 4, 2004, provisional application No. 60/522,449, filed on Oct. 3, 2004, provisional application No. 60/522,452, filed on Oct. 3, 2004.

(51) Int. Cl.
*C12N 15/11* (2006.01)
*C12N 15/113* (2010.01)
*C12Q 1/68* (2006.01)

(52) U.S. Cl.
CPC .......... *C12N 15/113* (2013.01); *C12Q 1/6876* (2013.01); *C12N 2310/141* (2013.01); *C12Q 2600/178* (2013.01)

(58) Field of Classification Search
CPC ................................................. C12N 2310/141
See application file for complete search history.

(56) References Cited

U.S. PATENT DOCUMENTS

| | | | |
|---|---|---|---|
| 5,998,383 A | * | 12/1999 | Wright ................ C12N 9/0093 435/183 |
| 7,250,289 B2 | | 7/2007 | Zhou |
| 7,407,784 B2 | | 8/2008 | Butzke et al. |
| 7,655,785 B1 | | 2/2010 | Bentwich |
| 7,820,809 B2 | | 10/2010 | Khvorova et al. |
| 2005/0075492 A1 | | 4/2005 | Chen et al. |
| 2005/0261218 A1 | | 11/2005 | Esau |
| 2006/0247193 A1 | | 11/2006 | Kazunari |
| 2008/0125583 A1 | | 5/2008 | Rigoutsos et al. |
| 2008/0269072 A1 | | 10/2008 | Hart et al. |
| 2012/0094374 A1 | | 4/2012 | Bentwich |
| 2014/0017780 A1 | | 1/2014 | Bentwich |
| 2016/0046935 A1 | | 2/2016 | Bentwich et al. |

FOREIGN PATENT DOCUMENTS

| | | |
|---|---|---|
| WO | 2003/029459 A2 | 4/2003 |
| WO | 2004/016317 A1 | 2/2004 |

OTHER PUBLICATIONS

Apr. 18, 1997. "EST28528 Cerebellum II *Homo sapiens* cDNA 5' end." XP002630735.
May 16, 2002. "*Homo sapiens* miR-102-precursor-1 micro RNA, complete sequence." XP002630736.
Jan. 16, 2001. "CM3-RT0006-091200-545-b05 RT0006 *Homo sapiens* cDNA, mRNA sequence." XP002630737.
May 16, 2002. "*Homo sapiens* miR-102-precursor-7.1 micro RNA, complete sequence." XP002630738.
"Human Genome, U95Av2", Oct. 2, 2002, XP002215481, http://www.affymetrix.com.
"GeneChip Human Genome U133 Set", Feb. 26, 2003, XP002232760, http://www.affymetrix.com/support/technical/datasheets/hgu133_datasheet.pdf.
Constantine L. et al., "Use of genechip high-density oligonucleotide arrays for gene expression monitoring", Life Science News, Amersham Life Science, US, Jan. 1, 1998, pp. 11-14, XP002964122.
Nov. 16, 2001, "Mus musculus 16 days neonate male diencephalon cDNA, Riken full-length enriched library, clone: G630058E01, 3' end partial sequence.", XP002630739.
Dec. 6, 2000, "UI-M-CG0p-bqm-b-04-0-UI.s1 NIH_BMAP_Ret4_S2 Mus musculus cDNA clone UI-M-CG0p-bqm-b-04-0-UI 3', mRNA sequence." XP002630740.

(Continued)

*Primary Examiner* — Dana H Shin
(74) *Attorney, Agent, or Firm* — Polsinelli PC; Ron Galant

(57) ABSTRACT

Described herein are polynucleotides associated with prostate and lung cancer. The polynucleotides are miRNAs and miRNA precursors. Related methods and compositions that can be used for diagnosis, prognosis, and treatment of those medical conditions are disclosed. Also described herein are methods that can be used to identify modulators of prostate and lung cancer.

3 Claims, 5 Drawing Sheets

(56) References Cited

OTHER PUBLICATIONS

Bartel D.P., "MicroRNAs: Genomics, biogenesis, mechanism, and function.", Cell, vol. 116, No. 2, Jan. 23, 2004, pp. 281-297, XP002359089.
Lee R.C., et al., "An extensive class of small RNAs in Caenorhabditis elegans", Science, American Association for the Advancement of Science, US, vol. 294, No. 5543, Oct. 26, 2001, pp. 862-864, XP002284273.
Lewis B.P., "Prediction of Mammalian MicroRNA Targets", Cell, Cell Press, Cambridge, NA, US, vol. 115, No. 7, Dec. 26, 2003, pp. 787-798, XP002295226.
Grad Y. et al., "Computational and Experimental Identification of C. Elegans Micrornas", Molecular Cell, Cell Press, Cambridge, MA, US, vol. 11, No. 5, May 1, 2003, pp. 1253-1263, XP009032050.
McManus, M.T., "MicroRNAs and cancer," Seminars in Cancer Biology, 13:253-258 (2003).
Calin, G.A., Human microRNA genes are frequently located at fragile sites and genomic regions involved in cancers, PNAS, 101(9): 2999-3004 (2004).
Paul, et al., "Inosine exists in mRNA at tissue-specific levels and is most abundant in brain mRNA," 1998, The EMBO Journal, vol. 17, pp. 1120-1127.
GenBank Accession No. BB017822, last updated Jun. 22, 2000.
GenBank Accession No. BF019006.1, last updated Dec. 29, 2000.
Lagos-Quintana, et al., Identification of tissue-specific microRNAs from mouse, 2002, Current Biology, vol. 12, pp. 735-739.

\* cited by examiner

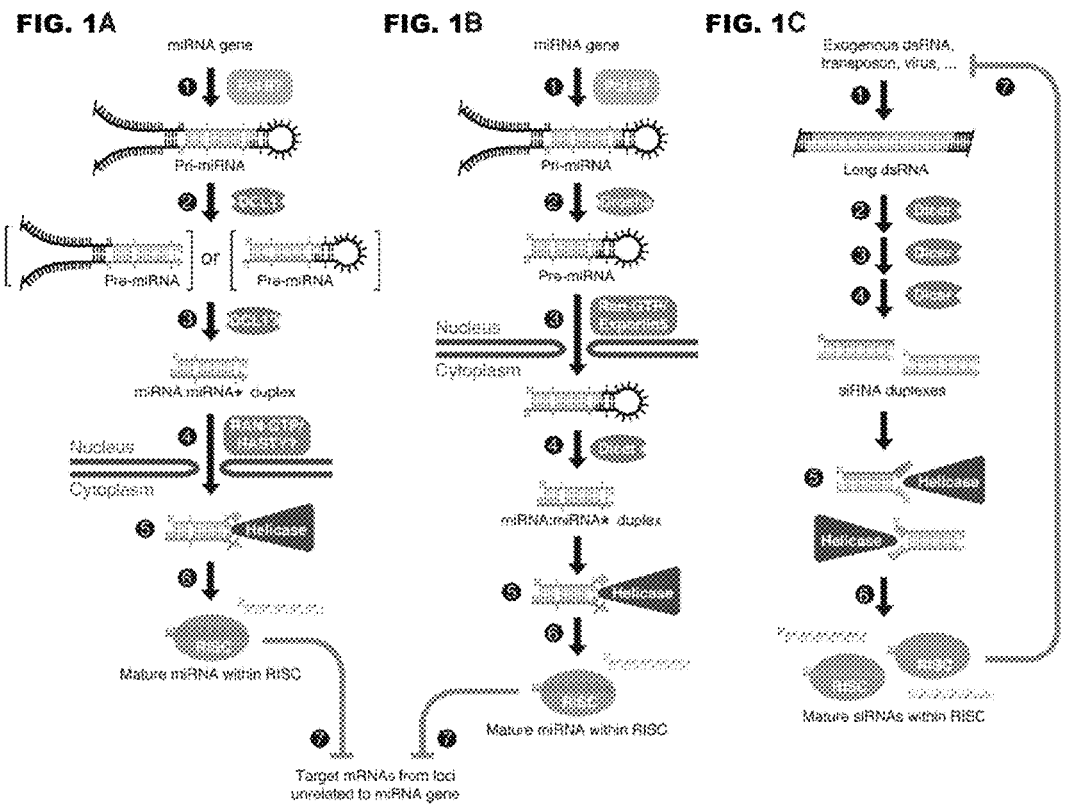

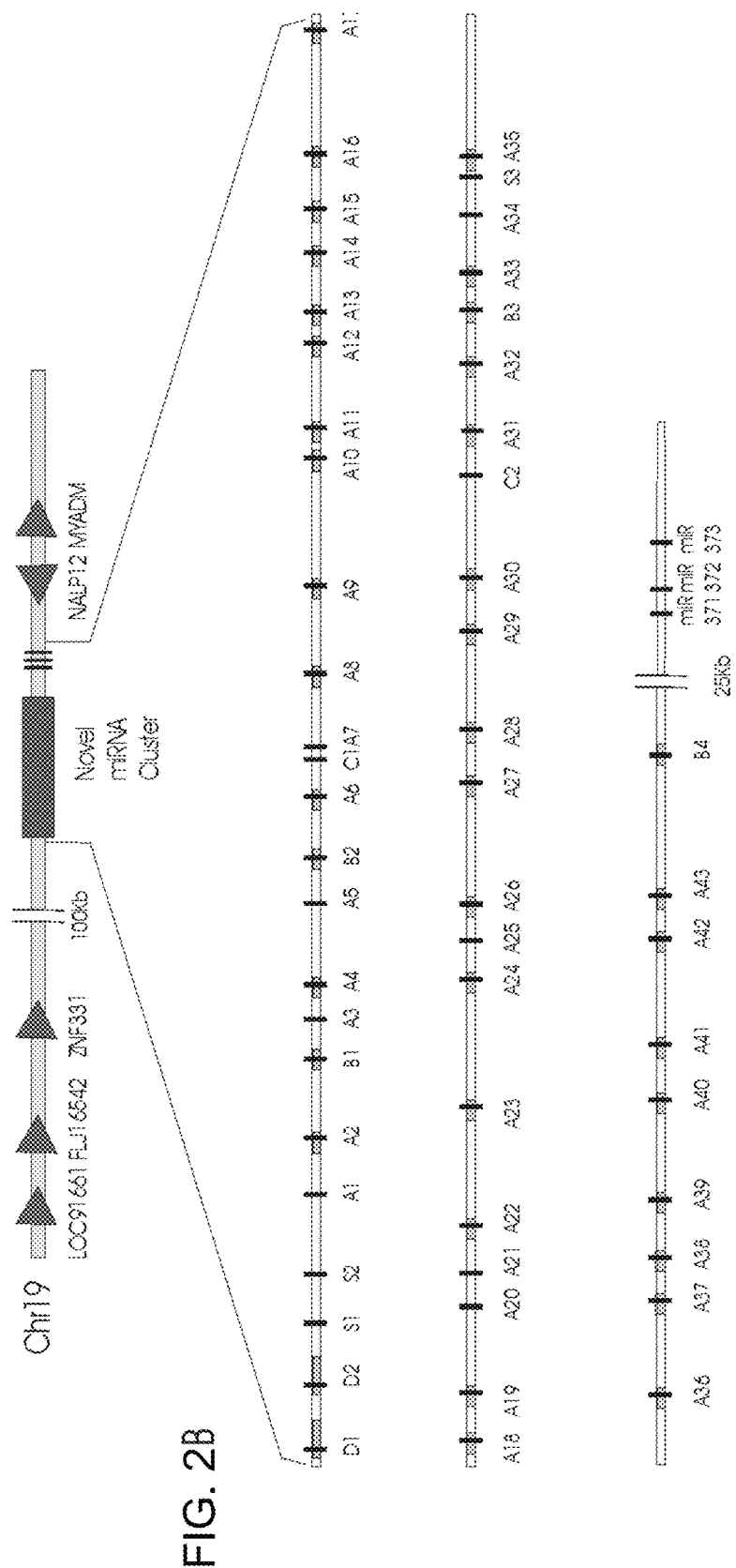

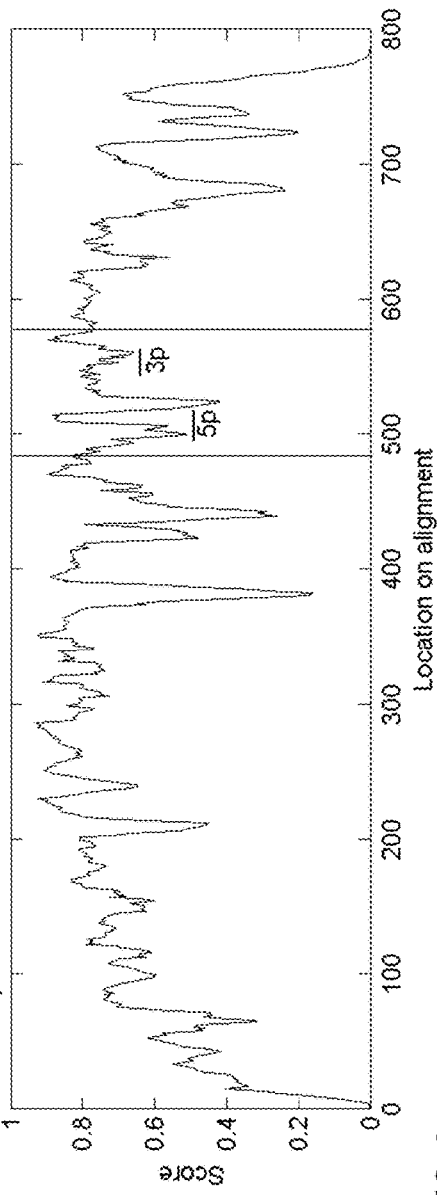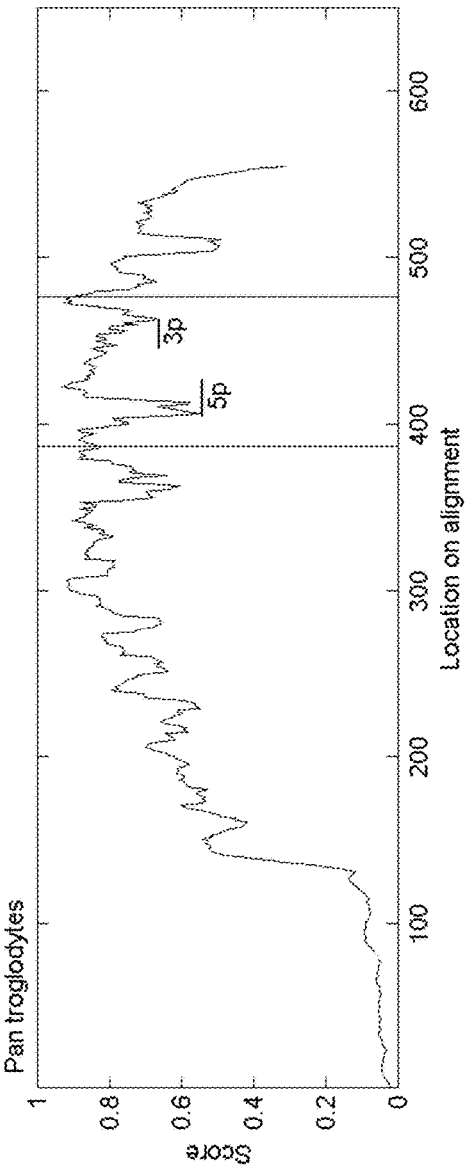
FIG. 3A Homo Sapiens
FIG. 3B Pan troglodytes

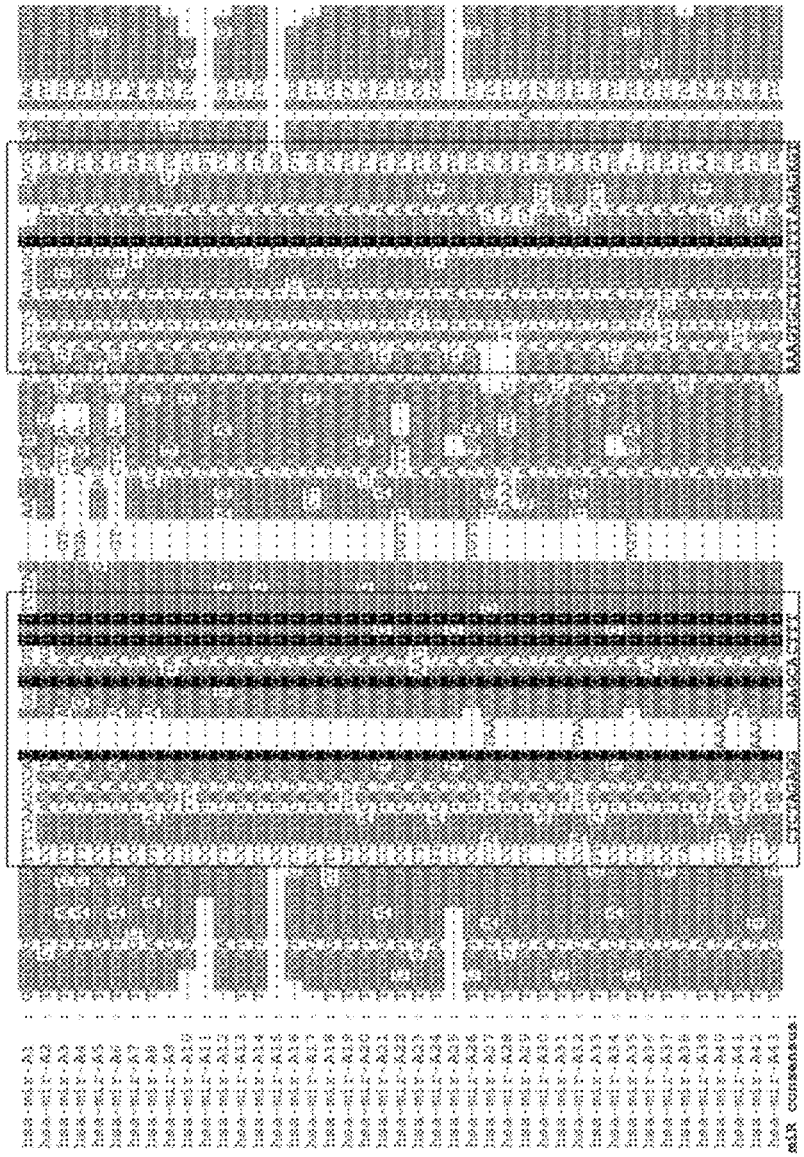
FIG. 4A
FIG. 4B
FIG. 4C

NUCLEIC ACID COMPOSITIONS RELATED TO MIR-138-1-3P AND USES THEREOF

FIELD OF THE INVENTION

The invention relates in general to microRNA molecules as well as various nucleic acid molecules relating thereto or derived therefrom.

REFERENCES TO THE SEQUENCE LISTING AND TABLES

Applicant hereby makes reference to the sequence listing and tables that were submitted electronically via EFS-Web. The sequence listing consists of a filed named "Sequence-Listing.txt," (14 KB), created on May 3, 2017. The tables consist of the following files: "Table1.txt" (1 KB), which was created on May 3, 2017; and "Table2.txt" (2 KB), "Table3.txt" (1 KB), "Table4.txt" (6 KB), "Table1.txt" (1 KB), "Table6.txt" (38 KB), "Table1.txt" (2 KB), "Table1.txt" (4 KB), "Table9.txt" (190 KB), which were created on May 2, 2017. The sequence listing and tables are all incorporated herein by reference.

SUMMARY OF THE INVENTION

The present invention is related to an isolated nucleic acid comprising a sequence of a pri-miRNA, pre-miRNA, miRNA, miRNA*, anti-miRNA, or a miRNA binding site, or a variant thereof. The nucleic acid may comprise the sequence of a hairpin referred to in Table 1; the sequence of a miRNA referred to in Table 1; the sequence of a target gene binding site referred to in Table 4; or a sequence comprising at least 12 contiguous nucleotides at least 60% identical thereto. The isolated nucleic acid may be from 5-250 nucleotides in length.

The present invention is also related to a probe comprising the nucleic acid. The probe may comprise at least 8-22 contiguous nucleotides complementary to a miRNA referred to in Table 2 as differentially expressed in prostate cancer or lung cancer.

The present invention is also related to a plurality of the probes. The plurality of probes may comprise at least one probe complementary to each miRNA referred to in Table 2 as differentially expressed in prostate cancer. The plurality of probes may also comprise at least one probe complementary to each miRNA referred to in Table 2 as differentially expressed in lung cancer.

The present invention is also related to a composition comprising a probe or plurality of probes.

The present invention is also related to a biochip comprising a solid substrate, said substrate comprising a plurality of probes. Each of the probes may be attached to the substrate at a spatially defined address. The biochip may comprise probes that are complementary to a miRNA referred to in Table 2 as differentially expressed in prostate cancer. The biochip may also comprise probes that are complementary to a miRNA referred to in Table 2 as differentially expressed in lung cancer.

The present invention is also related to a method of detecting differential expression of a disease-associated miRNA. A biological sample may be provide and the level of a nucleic acid measured that is at least 70% identical to a sequence of a miRNA referred to in Table 1; or variants thereof. A difference in the level of the nucleic acid compared to a control is indicative of differential expression.

The present invention is also related to a method of identifying a compound that modulates a pathological condition. A cell may be provided that is capable of expressing a nucleic acid at least 70% identical to a sequence of a miRNA referred to in Table 1 or variants thereof. The cell may be contacted with a candidate modulator and then measuring the level of expression of the nucleic acid. A difference in the level of the nucleic acid compared to a control identifies the compound as a modulator of a pathological condition associated with the nucleic acid.

The present invention is also related to a method of inhibiting expression of a target gene in a cell. Into the cell,

TABLES

The patent contains table(s) that have been included at the end of the specification.

BACKGROUND OF THE INVENTION

MicroRNAs (miRNAs) are short RNA oligonucleotides of approximately 22 nucleotides that are involved in gene regulation. MicroRNAs regulate gene expression by targeting mRNAs for cleavage or translational repression. Although miRNAs are present in a wide range of species including C. elegans, Drosophila and humans, they have only recently been identified. More importantly, the role of miRNAs in the development and progression of disease has only recently become appreciated.

As a result of their small size, miRNAs have been difficult to identify using standard methodologies. A limited number of miRNAs have been identified by extracting large quantities of RNA. MiRNAs have also been identified that contribute to the presentation of visibly discernable phenotypes. Expression array data shows that miRNAs are expressed in different developmental stages or in different tissues. The restriction of miRNAs to certain tissues or at limited developmental stages indicates that the miRNAs identified to date are likely only a small fraction of the total miRNAs.

Computational approaches have recently been developed to identify the remainder of miRNAs in the genome. Tools such as MiRscan and MiRseeker have identified miRNAs that were later experimentally confirmed. Based on these computational tools, it has been estimated that the human genome contains 200-255 miRNA genes. These estimates are based on an assumption, however, that the miRNAs remaining to be identified will have the same properties as those miRNAs already identified. Based on the fundamental importance of miRNAs in mammalian biology and disease, the art needs to identify unknown miRNAs. The present invention satisfies this need and provides a significant number of miRNAs and uses therefore.

a nucleic acid may be introduced in an amount sufficient to inhibit expression of the target gene. The target gene may comprise a binding site substantially identical to a binding site referred to in Table 4; or a variant thereof. The nucleic acid may comprise a sequence of one of SEQ ID NOS: 1-4; or a variant thereof. Expression of the target gene may be inhibited in vitro or in vivo.

The present invention is also related to a method of increasing expression of a target gene in a cell. Into the cell, a nucleic acid may be introduced in an amount sufficient to inhibit expression of the target gene. The target gene may comprise a binding site substantially identical to a binding site referred to in Table 4; or a variant thereof. The nucleic acid may comprise a sequence substantially complementary to one of SEQ ID NOS: 1-4; or a variant thereof. Expression of the target gene may be inhibited in vitro or in vivo. Expression of the target gene may be increased in vitro or in vivo.

The present invention is also related to a method of treating a patient with a disorder set forth on Table 6 comprising administering to a patient in need thereof a nucleic acid comprising a sequence of one of SEQ ID NOS: 1-4; or a variant thereof.

BRIEF DESCRIPTION OF THE DRAWINGS

FIGS. 1A-1C demonstrate a model of maturation for miRNAs.

FIG. 2A shows a schematic illustration of the MC19cluster on 19q13.42. FIG. 2A shows the ~500,000 bp region of chromosome 19, from 58,580,001 to 59,080,000 (according to the May 2004 USCS assembly), in which the cluster is located including the neighboring protein-coding genes. The MC19-1 cluster is indicated by a rectangle. Mir-371, mir-372, and mir-373 are indicted by lines. Protein coding genes flanking the cluster are represented by large arrow-heads. FIG. 2B shows a detailed structure of the MC19-1 miRNA cluster. A region of ~102,000 bp, from 58,860,001 to 58,962,000 (according to the May 2004 USCS assembly), is presented. MiRNA precursors are represented by a black bars. It should be noted that all miRNAs are at the same orientation from left to right. Shaded areas around miRNA precursors represent repeating units in which the precursor is embedded. The location of mir-371, mir-372, and mir-373, is also presented.

FIGS. 3A-3B are a graphical representation of multiple sequence alignment of 35 human repeat units at distinct size of ~690 nt (FIG. 3A) and 26 chimpanzees repeat units (FIG. 3B). The graph was generated by calculating a similarity score for each position in the alignment with an averaging sliding window of 10 nt (Maximum score −1, minimum score-0). The repeat unit sequences were aligned by ClustalW program. Each position of the resulting alignment was assigned a score which represented the degree of similarity at this position. The region containing the miRNA precursors is bordered by vertical lines. The exact location of the mature miRNAs derived from the 5' stems (5p) and 3' stems (3p) of the precursors is indicted by vertical lines.

FIGS. 4A-4C show sequence alignments of the 43 A-type pre-miRNAs of the MC19-1 cluster. FIG. 4A shows the multiple sequence alignment with the Position of the mature miRNAs marked by a frame. The consensus sequence is shown at the bottom. Conserved nucleotides are colored as follows: black-100%, dark grey—80% to 99%, and clear grey—60% to 79%. FIG. 4B shows alignments of consensus mature A-type miRNAs with the upstream human cluster of mir-371, mir-372, miR-373. FIG. 4C shows alignments of consensus mature A-type miRNAs with the hsa-mir-371-373 mouse orthologous cluster. The miRNAs hsa-miR-A1 through hsa-miR-A43 of FIG. 4A have SEQ ID NOs: 13 through 66, respectively. In FIG. 4B, the following miRNAs have the following sequences: hsa-miR-371, 3p (SEQ ID NO: 67), hsa-miR-372, 3p (SEQ ID NO: 68), hsa-miR-373, 3p (SEQ ID NO: 69), hsa-miR-A-3p (consensus)(SEQ ID NO: 70), hsa-miR-373-5-p (SEQ ID NO: 71), hsa-miR-A-5p (consensus)(SEQ ID NO: 77). In FIG. 4C, the following miRNAs have the following sequences: hsa-miR-302a (SEQ ID NO: 72), hsa-miR-302b (SEQ ID NO: 73), hsa-miR-302c (SEQ ID NO: 74), hsa-miR-302d (SEQ ID NO: 75), and hsa-miR-A-3p (consensus)(SEQ ID NO: 76). FIG. 5A shows a Northern blot analysis of two selected A-type miRNAs. Expression was analyzed using total RNA from human brain (B), liver (L), thymus (T), placenta (P) and HeLa cells (H). The expression of mir-98 and ethidium bromide staining of the tRNA band served as control. FIG. 5B shows RT-PCR analysis of the mRNA transcript containing the A-type miRNA precursors. Reverse transcription of 5 μg total RNA from placenta was performed using oligo-dT. This was followed by PCR using the denoted primers (indicated by horizontal arrows). The region examined is illustrated at the top. Vertical black bars represent the pre-miRNA; shaded areas around the pre-miRNAs represent the repeating units; the location of four ESTs is indicted at the right side; the poly-A site, as found in the ESTs and located downstream to an AATAAA consensus, is indicated by a vertical arrow. The fragments expected from RT-PCR using three primer combinations are indicated below the illustration of the cluster region. The results of the RT-PCR analysis are presented below the expected fragments. FIG. 5C shows the sequencing strategy of the FR2 fragment. The fragment was cloned into the pTZ57R\T vector and sequenced using external and internal primers.

DETAILED DESCRIPTION

Figure 5A:
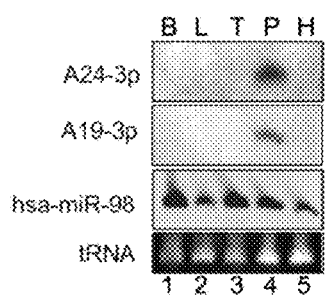
FIGS. 5A-C show expression analysis of the MC19-1 miRNAs.

The present invention provides nucleotide sequences of miRNAs, precursors thereto, targets thereof and related sequences. Such nucleic acids are useful for diagnostic purposes, and also for modifying target gene expression. Other aspects of the invention will become apparent to the skilled artisan by the following description of the invention.

1. Definitions

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

a. Animal

"Animal" as used herein may mean fish, amphibians, reptiles, birds, and mammals, such as mice, rats, rabbits, goats, cats, dogs, cows, apes and humans.

b. Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

c. Biological Sample

"Biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. Archival tissues, such as those having treatment or outcome history, may also be used.

d. Complement

"Complement" or "complementary" as used herein may mean Watson-Crick or Hoogsteen base pairing between nucleotides or nucleotide analogs of nucleic acid molecules.

e. Differential Expression

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type which may be detectable by standard techniques. Some genes will be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

f. Gene

"Gene" used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA and antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

g. Host Cell

"Host cell" used herein may be a naturally occurring cell or a transformed cell that contains a vector and supports the replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO, HeLa.

h. Identity

"Identical" or "identity" as used herein in the context of two or more nucleic acids or polypeptide sequences, may mean that the sequences have a specified percentage of nucleotides or amino acids that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered end and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

i. Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

j. Nucleic Acid

"Nucleic acid" or "oligonucleotide" or "polynucleotide" used herein may mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid may be used for the same purpose as a given nucleic acid. Thus, a nucleic acid also encompasses substantially identical nucleic acids and complements thereof. As will also be appreciated by those in the art, a single strand provides a probe for a probe that may hybridize to the target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and nonribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modifications of the ribose-phosphate backbone may be done for a variety of reasons, e.g., to increase the stability and half-life of such molecules in physiological environments or as probes on a biochip. Mixtures of naturally occurring nucleic acids and analogs may be made; alternatively, mixtures of different nucleic acid analogs, and mixtures of naturally occurring nucleic acids and analogs may be made.

k. Operably Linked

"Operably linked" used herein may mean that expression of a gene is under the control of a promoter with which it is spatially connected. A promoter may be positioned 5' (upstream) or 3' (downstream) of the gene under its control. The distance between the promoter and the gene may be approximately the same as the distance between that promoter and the gene it controls in the gene from which the promoter is derived. As is known in the art, variation in this distance can be accommodated without loss of promoter function.

l. Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

m. Promoter

"Promoter" as used herein may mean a synthetic or naturally-derived molecule which is capable of conferring, activating or enhancing expression of a nucleic acid in a cell. A promoter may comprise one or more specific regulatory elements to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

n. Selectable Marker

"Selectable marker" used herein may mean any gene which confers a phenotype on a cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein-encoding gene and luciferase gene.

o. Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids, but to no other sequences. Stringent conditions are sequence-dependent and will be different in different circumstances. Generally, stringent conditions are selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

p. Substantially Complementary

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

q. Substantially Identical

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence.

r. Target

"Target" as used herein may mean a polynucleotide that may be bound by one or more probes under stringent hybridization conditions.

s. Terminator

"Terminator" used herein may mean a sequence at the end of a transcriptional unit which signals termination of transcription. A terminator may be a 3'-non-translated DNA sequence containing a polyadenylation signal, which may facilitate the addition of polyadenylate sequences to the 3'-end of a primary transcript. A terminator may be derived from sources including viral, bacterial, fungal, plants, insects, and animals. Representative examples of terminators include the SV40 polyadenylation signal, HSV TK polyadenylation signal, CYC1 terminator, ADH terminator, SPA terminator, nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit gene (SSU) gene terminator sequences, subclover stunt virus (SCSV) gene sequence terminators, rho-independent *E. coli* terminators, and the lacZ alpha terminator.

t. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrate into a host genome.

2. MicroRNA

While not being bound by theory, the current model for the maturation of mammalian miRNAs is shown in FIG. 1. A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. As indicated on FIG. 1, the stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as single-stranded RNAs into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke at al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA complementarity sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity.

It should be notes that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. Nucleic Acid

The present invention relates to an isolated nucleic acid comprising a nucleotide sequence referred to in SEQ ID NOS: 1-4, or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 100 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides. The nucleic acid may be synthesized or expressed in a cell (in vitro or in vivo) using a synthetic gene described below. The nucleic acid may be synthesized as a single strand molecule and hybridized to a substantially complementary nucleic acid to form a duplex, which is considered a nucleic acid of the invention. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

a. Pri-miRNA

The nucleic acid of the invention may comprise a sequence of a pri-miRNA or a variant thereof. The pri-miRNA sequence may comprise from 45-250, 55-200, 70-150 or 80-100 nucleotides. The sequence of the pri-miRNA may comprise a pre-miRNA, miRNA and miRNA* as set forth below. The pri-miRNA may also comprise a miRNA or miRNA* and the complement thereof, and variants thereof. The pri-miRNA may comprise at least 19% adenosine nucleotides, at least 16% cytosine nucleotides, at least 23% thymine nucleotides and at least 19% guanine nucleotides.

The pri-miRNA may form a hairpin structure. The hairpin may comprise a first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides.

The sequence of the pri-miRNA may comprise the sequence of a hairpin referred to in Table 1, or variants thereof. The numerical identifiers for HID (hairpins) and MID (miRNAs) in Tables 1-9 correspond to SEQ ID NOS: 1-4 as follows.

TABLE 10

| MID Sequence Identifiers | |
|---|---|
| HID Numerical Identifier | SEQ ID NO |
| 778 | 1 |

TABLE 11

| HID Sequence Identifiers | |
|---|---|
| MID Numerical Identifier | SEQ ID NO |
| 8545 | 2 |
| 8546 | 3 |
| 8547 | 4 |

The MID and HID numerical identifiers in the tables above refer to the hairpins and miRNAs with the same numerical identifiers described in Tables 1-10 of U.S. Patent Publication No. 2016/0046935, the contents of which are incorporated herein by reference, and use the same numbers as the sequence identifiers in the sequence listing of U.S. Patent Publication No. 2016/0046935, the contents of which are incorporated herein by reference.

b. Pre-miRNA

The nucleic acid of the invention may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth below. The pre-miRNA may also comprise a miRNA or miRNA* and the complement thereof, and variants thereof. The sequence of the pre-miRNA may also be that of a pri-miRNA excluding from 0-160 nucleotides from the 5' and 3' ends of the pri-miRNA.

The sequence of the pre-miRNA may comprise the sequence of a hairpin referred to in Table 1, or variants thereof.

c. MiRNA

The nucleic acid of the invention may also comprise a sequence of a miRNA, miRNA* or a variant thereof. The miRNA sequence may comprise from 13-33, 18-24 or 21-23 nucleotides. The sequence of the miRNA may be the first 13-33 nucleotides of the pre-miRNA. The sequence of the miRNA may be the last 13-33 nucleotides of the pre-miRNA.

The sequence of the miRNA may comprise the sequence of a miRNA referred to in Table 1, or variants thereof.

d. Anti-miRNA

The nucleic acid of the invention may also comprise a sequence of an anti-miRNA that is capable of blocking the activity of a miRNA or miRNA*. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25 or 26 nucleotides. The sequence of the anti-miRNA may comprise (a) at least 5 nucleotides that are substantially identical to the 5' of a miRNA and at least 5-12 nucleotide that are substantially complimentary to the flanking regions of the target site from the 5' end of said miRNA, or (b) at least 5-12 nucleotides that are substantially identical to the 3' of a miRNA and at least 5 nucleotide that are substantially complimentary to the flanking region of the target site from the 3' end of said miRNA.

The sequence of the anti-miRNA may comprise the compliment of a sequence of a miRNA referred to in Table 1, or variants thereof.

e. Binding Site of Target

The nucleic acid of the invention may also comprise a sequence of a target miRNA binding site, or a variant thereof. The target site sequence may comprise a total of 5-100 or 10-60 nucleotides. The target site sequence may comprise at least 5 nucleotides of the sequence of a target gene binding site referred to in Table 4, or variants thereof.

4. Synthetic Gene

The present invention also relates to a synthetic gene comprising a nucleic acid of the invention operably linked to a transcriptional and/or translational regulatory sequences. The synthetic gene may be capable of modifying the expression of a target gene with a binding site for the nucleic acid of the invention. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

The present invention also relates to a vector comprising a synthetic gene of the invention. The vector may be an expression vector. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

The present invention also relates to a host cell comprising a vector of the invention. The cell may be a bacterial, fungal, plant, insect or animal cell.

7. Probes

The present invention also relates to a probe comprising a nucleic acid of the invention. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

8. Biochip

The present invention also relates to a biochip. The biochip may comprise a solid substrate comprising an attached probe or plurality of probes of the invention. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder.

The probes may be attached to the biochip in a wide variety of ways, as will be appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linkers. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. miRNA Expression Analysis

The present invention also relates to a method of identifying miRNAs that are associated with disease or a pathological condition comprising contacting a biological sample with a probe or biochip of the invention and detecting the amount of hybridization. PCR may be used to amplify nucleic acids in the sample, which may provide higher sensitivity.

The ability to identify miRNAs that are overexpressed or underexpressed in pathological cells compared to a control can provide high-resolution, high-sensitivity datasets which may be used in the areas of diagnostics, therapeutics, drug development, pharmacogenetics, biosensor development, and other related areas. An expression profile generated by the current methods may be a "fingerprint" of the state of the sample with respect to a number of miRNAs. While two states may have any particular miRNA similarly expressed, the evaluation of a number of miRNAs simultaneously allows the generation of a gene expression profile that is characteristic of the state of the cell. That is, normal tissue may be distinguished from diseased tissue. By comparing expression profiles of tissue in known different disease states, information regarding which miRNAs are associated in each of these states may be obtained. Then, diagnosis may be performed or confirmed to determine whether a tissue sample has the expression profile of normal or disease tissue. This may provide for molecular diagnosis of related conditions.

10. Determining Expression Levels

The present invention also relates to a method of determining the expression level of a disease-associated miRNA comprising contacting a biological sample with a probe or biochip of the invention and measuring the amount of hybridization. The expression level of a disease-associated miRNA is information in a number of ways. For example, a differential expression of a disease-associated miRNA compared to a control may be used as a diagnostic that a patient suffers from the disease. Expression levels of a disease-associated miRNA may also be used to monitor the treatment and disease state of a patient. Furthermore, expression levels of e disease-associated miRNA may allow the screening of drug candidates for altering a particular expression profile or suppressing an expression profile associated with disease.

A target nucleic acid may be detected by contacting a sample comprising the target nucleic acid with a biochip comprising an attached probe sufficiently complementary to the target nucleic acid and detecting hybridization to the probe above control levels.

The target nucleic acid may also be detected by immobilizing the nucleic acid to be examined on a solid support such as nylon membranes and hybridizing a labelled probe with the sample. Similarly, the target nucleic may also be detected by immobilizing the labeled probe to the solid support and hybridizing a sample comprising a labeled target nucleic acid. Following washing to remove the non-specific hybridization, the label may be detected.

The target nucleic acid may also be detected in situ by contacting permeabilized cells or tissue samples with a labeled probe to allow hybridization with the target nucleic acid. Following washing to remove the non-specifically bound probe, the label may be detected.

These assays can be direct hybridization assays or can comprise sandwich assays, which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

a. Diagnostic

The present invention also relates to a method of diagnosis comprising detecting a differential expression level of a disease-associated miRNA in a biological sample. The sample may be derived from a patient. Diagnosis of a disease state in a patient allows for prognosis and selection of therapeutic strategy. Further, the developmental stage of cells may be classified by determining temporarily expressed miRNA-molecules.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

b. Drug Screening

The present invention also relates to a method of screening therapeutics comprising contacting a pathological cell capable of expressing a disease related miRNA with a candidate therapeutic and evaluating the effect of a drug candidate on the expression profile of the disease associated miRNA. Having identified the differentially expressed miRNAs, a variety of assays may be executed. Test compounds may be screened for the ability to modulate gene expression of the disease associated miRNA. Modulation includes both an increase and a decrease in gene expression.

The test compound or drug candidate may be any molecule, e.g., protein, oligopeptide, small organic molecule, polysaccharide, polynucleotide, etc., to be tested for the capacity to directly or indirectly alter the disease phenotype or the expression of the disease associated miRNA. Drug candidates encompass numerous chemical classes, such as small organic molecules having a molecular weight of more than 100 and less than about 500, 1,000, 1,500, 2,000 or 2,500 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Combinatorial libraries of potential modulators may be screened for the ability to bind to the disease associated miRNA or to modulate the activity thereof. The combinatorial library may be a collection of diverse chemical compounds generated by either chemical synthesis or biological synthesis by combining a number of chemical building blocks such as reagents. Preparation and screening of combinatorial chemical libraries is well known to those of skill in the art. Such combinatorial chemical libraries include, but are not limited to, peptide libraries encoded peptides, benzodiazepines, diversomers such as hydantoins, benzodiazepines and dipeptide, vinylogous polypeptides, analogous organic syntheses of small compound libraries, oligocarbamates, and/or peptidyl phosphonates, nucleic acid libraries, peptide nucleic acid libraries, antibody libraries, carbohydrate libraries, and small organic molecule libraries.

11. Gene Silencing

The present invention also relates to a method of using the nucleic acids of the invention to reduce expression of a target gene in a cell, tissue or organ. Expression of the target gene may be reduced by expressing a nucleic acid of the invention that comprises a sequence substantially complementary to one or more binding sites of the target mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target mRNA, which may lead to activation of RISC-mediated gene silencing. An example for a study employing over-expression of miRNA is Yekta et al 2004, Science 304-594, which is incorporated herein by reference. One of ordinary skill in the art will recognize that the nucleic acids of the present invention may be used to inhibit expression of target genes using antisense methods well known in the art, as well as RNAi methods described in U.S. Pat. Nos. 6,506,559 and 6,573,099, which are incorporated by reference.

The target of gene silencing may be a protein that causes the silencing of a second protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which is incorporated herein by reference.

12. Gene Enhancement

The present invention also relates to a method of using the nucleic acids of the invention to increase expression of a target gene in a cell, tissue or organ. Expression of the target gene may be increased by expressing a nucleic acid of the invention that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid of the invention that is substantially complementary to a portion of the binding site in the target gene, such that binding of the nucleic acid to the binding site may prevent miRNA binding.

13. Therapeutic

The present invention also relates to a method of using the nucleic acids of the invention as modulators or targets of disease or disorders associated with developmental dysfunctions, such as cancer. In general, the claimed nucleic acid molecules may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. Further, miRNA molecules can be modified, in order that they are processed and then generated as double-stranded siRNAs which are again directed against therapeutically relevant targets. Furthermore, miRNA molecules may be used for tissue reprogramming procedures, e.g. a differentiated cell line might be transformed by expression of miRNA molecules into a different cell type or a stem cell.

14. Compositions

The present invention also relates to a pharmaceutical composition comprising the nucleic acids of the invention and optionally a pharmaceutically acceptable carrier. The compositions may be used for diagnostic or therapeutic applications. The administration of the pharmaceutical composition may be carried out by known methods, wherein a nucleic acid is introduced into a desired target cell in vitro or in vivo. Commonly used gene transfer techniques include calcium phosphate, DEAE-dextran, electroporation, microinjection, viral methods and cationic liposomes.

15. Kits

The present invention also relates to kits comprising a nucleic acid of the invention together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods of this invention.

EXAMPLE 1

Prediction of MiRNAs

We surveyed the entire human genome for potential miRNA coding genes using two computational approaches similar to those described in U.S. Patent Application No. 60/522,459, Ser. No. 10/709,577 and Ser. No. 10/709,572, the contents of which are incorporated herein by reference, for predicting miRNAs. Briefly, non-protein coding regions of the entire human genome were scanned for hairpin structures. The predicted hairpins and potential miRNAs were scored by thermodynamic stability, as well as structural and contextual features. The algorithm was calibrated by using miRNAs in the Sanger Database which had been validated.

1. First Screen

The first screen was described in U.S. patent application Ser. No. 10/709,572, in which Table 2 shows the sequence ("PRECURSOR SEQUENCE"), sequence identifier ("PRECUR SEQ-ID") and organism of origin ("GAM ORGANISM") for each predicted hairpin from the first computational screen, together with the predicted miRNAs ("GAM NAME"). Table 1 of U.S. patent application Ser. No. 10/709,572, the contents of which are incorporated herein by reference, shows the sequence ("GAM RNA SEQUENCE") and sequence identifier ("GAM SEQ-ID") for each miRNA ("GAM NAME"), along with the organism of origin ("GAM ORGANISM") and Dicer cut location ("GAM POS"). The sequences of the predicted hairpins and miRNA are also set forth in the Sequence Listing of U.S. patent application Ser. No. 10/709,572, the contents of which are incorporated herein by reference.

2. Second Screen

Table 1 lists the numerical identifier for each predicted hairpin ("HID") of the second computational screen. Table 1 also lists the genomic location for each hairpin ("Hairpin Location"). The format for the genomic location is a concatenation of <chr_id><strand><start position>. For example, 19+135460000 refers chromosome 19, +strand, start position 135460000. Chromosomes 23-25 refer to chromosome X, chromosome Y and mitochondrial DNA. The chromosomal location is based on the hg17 assembly of the human genome by UCSC (genome.ucsc.edu), which is based on NCBI Build 35 version 1 and was produced by the International Human Genome Sequencing Consortium.

Table 1 also lists whether the hairpin is conserved in evolution ("C"). There is an option that there is a paper of the genome version. The hairpins were identified as conserved ("Y") or nonconserved ("N") by using phastCons data. The phastCons data is a measure of evolutionary conservation for each nucleotide in the human genome against the genomes of chimp, mouse, rat, dog, chicken, frog, and zebrafish, based on a phylo-HMM using best-in-genome pair wise alignment for each species based on BlastZ, followed by multiZ alignment of the 8 genomes (Siepel et al, J. Comput. Biol 11, 413-428, 2004 and Schwartz et al., Genome Res. 13, 103-107, 2003). A hairpin is listed as conserved if the average phastCons conservation score over the 7 species in any 15 nucleotide sequence within the hairpin stem is at least 0.9 (Berezikov, E. et al. Phylogenetic Shadowing and Computational Identification of Human microRNA Genes. Cell 120, 21-24, 2005).

Table 1 also lists the genomic type for each hairpin ("T") as either intergenic ("G"), intron ("I") or exon ("E"). Table 1 also lists the numerical identifier ("MID") for each predicted miRNA and miRNA*. Table 1 also lists the prediction score grade for each hairpin ("P") on a scale of 0-1 (1 the hairpin is the most reliable), as described in Hofacker et al., Monatshefte f. Chemie 125: 167-188, 1994. If the grade is zero or null, they are transformed to the lower value of PalGrade that its p-value is <0.05. Table 1 also lists the p-value ("Pval") calculated out of background hairpins for the values of each P scores. As shown in Table, there are few instances where the Pval is >0.05. In each of these cases, the hairpins are highly conserved or they have been validated (F=Y).

Table 1 also lists whether the miRNAs were validated by expression analysis ("E") (Y=Yes, N=No), as detailed in Table 2. Table 1 also lists whether the miRNAs were validated by sequencing ("S") (Y=Yes, N=No). If there was a difference in sequences between the predicted and sequenced miRNAs, the sequenced sequence is predicted. It should be noted that failure to sequence or detect expression of a miRNA does not necessarily mean that a miRNA does not exist. Such undetected miRNAs may be expressed in tissues other than those tested. In addition, such undetected miRNAs may be expressed in the test tissues, but at a difference stage or under different condition than those of the experimental cells.

Table 1 also listed whether the miRNAs were shown to be differentially expressed ("D") (Y=Yes, N=No) in at least one disease, as detailed in Table 2). Table 1 also whether the miRNAs were present ("F") (Y=Yes, N=No) in Sanger DB Release 6.0 (April 2005) (http://nar.oupjournals.org/) as being detected in humans or mice or predicted in humans. As discussed above, the miRNAs listed in the Sanger database are a component of the prediction algorithm and a control for the output.

Table 1 also lists a genetic location cluster ("LC") for those hairpins that are within 5,000 nucleotides of each other. Each miRNA that has the same LC share the same genetic cluster. Table 1 also lists a seed cluster ("SC") to group miRNAs by their seed of 2-7 by an exact match. Each miRNA that has the same SC have the same seed. For a discussion of seed lengths of 5 nucleotides, see Lewis et al., Cell, 120; 15-20 (2005).

EXAMPLE 2

Prediction of Target Genes

The predicted miRNAs from the two computational screens of Example 1 were then used to predict target genes and their binding sites using two computational approaches similar to those described in U.S. Patent Application No. 60/522,459, Ser. No. 10/709,577 and Ser. No. 10/709,572, the contents of which are incorporated herein by reference, for predicting miRNAs.

1. First Screen

Table 6 of U.S. patent application Ser. No. 10/709,572, the contents of which are incorporated herein by reference, lists the predicted target genes ("TARGET") and binding site sequence ("TARGET BINDING SITE SEQUENCE") and binding site sequence identifier ("TARGET BINDING SITE SEQ-ID") from the first computational screen, as well as the organism of origin for the target ("TARGET ORGANISM"). Table 12 of U.S. patent application Ser. No. 10/709,572, the contents of which are incorporated herein by reference, lists the diseases ("DISEASE NAME") that are associated with the target genes ("TARGET-GENES ASSOCIATED WITH DISEASE"). Table 14 of U.S. patent application Ser. No. 10/709,572, the contents of which are incorporated herein by reference, lists the sequence identifiers for the miRNAs ("SEQ ID NOs OF GAMS ASSOCIATED WITH DISEASE") and the diseases ("DISEASE NAME") that are associated with the miRNA based on the target gene. The sequences of the binding site sequences are also set forth on the Sequence Listing of U.S. patent application Ser. No. 10/709,572, the contents of which are incorporated herein by reference.

2. Second Screen

Table 4 lists the predicted target gene for each miRNA (MID) and its hairpin (HID) from the second computational screen. The names of the target genes were taken from NCBI Reference Sequence release 9 (www.ncbi.nlm.nih.gov; Pruitt et al., Nucleic Acids Res, 33(1):D501-D504, 2005; Pruitt et al., Trends Genet., 16(1):44-47, 2000; and Tatusova et al., Bioinformatics, 15(7-8):536-43, 1999). Target genes were identified by having a perfect complimentary match of a 7 nucleotide miRNA seed (positions 2-8) and an A on the UTR (total=8 nucleotides). For a discussion on identifying target genes, see Lewis et al., Cell, 120: 15-20, (2005). For a discussion of the seed being sufficient for binding of a miRNA to a UTR, see Lim Lau et al., (Nature 2005) and Brenneck et al, (PLoS Biol 2005).

Binding sites were then predicted using a filtered target genes dataset by including only those target genes that contained a UTR of a least 30 nucleotides. The binding site screen only considered the first 4000 nucleotides per UTR and considered the longest transcript when there were several transcripts per gene. The filtering reduced the total number of transcripts from 23626 to 14239. Table 4 lists the SEQ ID NO for the predicted binding sites for each target gene, as described in the Sequence Listing of International Publication WO 2005/111211, the contents of which are incorporated herein by reference. The sequence of the binding site includes the 20 nucleotides 5' and 3' of the binding site as they are located on the spliced mRNA. Except for those miRNAs that have only a single predicted binding site or those miRNAs that were validated, the data in Table 4 has been filtered to only indicate those target genes with at least 2 binding sites.

Table 5 shows the relationship between the miRNAs ("MID")/hairpins ("HID") and diseases by their target genes. The name of diseases are taken from OMIM. For a discussion of the rational for connecting the host gene the hairpin is located upon to disease, see Baskerville and Bartel, RNA, 11: 241-247 (2005) and Rodriguez et al., Genome Res., 14: 1902-1910 (2004). Table 5 shows the number of miRNA target genes ("N") that are related to the disease. Table 5 also shows the total number of genes that are related to the disease ("T"), which is taken from the genes that were predicted to have binding sites for miRNAs. Table 5 also shows the percentage of N out of T and the p-value of hypergeometric analysis ("Pval"). Table 8 shows the disease codes for Tables 5 and 6. For a reference of hypergeometric analysis, see Schaum's Outline of Elements of Statistics II: Inferential Statistics.

Table 6 shows the relationship between the miRNAs ("MID")/hairpins ("HID") and diseases by their host genes. We defined hairpins genes on the complementary strand of a host gene as located on the gene: Intron_c as Interon and Exon_c as Exon. We choose the complementary strands as they can cause disease. For example, a mutation in the miRNA that is located on the complementary strand. In those case that a miRNA in on both strands, two statuses like when Intron and Exon_c Intron is the one chosen. The logic of choosing is Intron>Exon>Intron_c>Exon_c>Intergenic. Table 9 shows the relationship between the target sequences ("Gene Name") and disease ("Disease Code").

EXAMPLE 3

Validation of miRNAs

1. Expression Analysis—Set 1

To confirm the hairpins and miRNAs predicted in Example 1, we detected expression in various tissues using the high-throughput microarrays similar to those described in U.S. Patent Application No. 60/522,459, Ser. No. 10/709,577 and Ser. No. 10/709,572, the contents of which are incorporated herein by reference. For each predicted precursor miRNA, mature miRNAs derived from both stems of the hairpin were tested.

Table 2 shows the hairpins ("HID") of the second prediction set that were validated by detecting expression of related miRNAs ("MID"), as well as a code for the tissue ("Tissue") that expression was detected. The tissue and diseases codes for Table 2 are listed in Table 7. Some of the tested tissues wee cell line. Lung carcinoma cell line (H1299) with/without P53: H1299 has a mutated P53. The cell line was transfected with a construct with P53 that is temperature sensitive (active at 32° C.). The experiment was conducted at 32° C.

Table 2 also shows the chip expression score grade (range of 500-65000). A threshold of 500 was used to eliminate non-significant signals and the score was normalized by MirChip probe signals from different experiments. Variations in the intensities of fluorescence material between experiments may be due to variability in RNA preparation or labeling efficiency. We normalized based on the assumption that the total amount of miRNAs in each sample is relatively constant. First we subtracted the background signal from the raw signal of each probe, where the background signal is defined as 400. Next, we divided each miRNA probe signal by the average signal of all miRNAs, multiplied the result by 10000 and added back the background signal of 400. Thus, by definition, the sum of all miRNA probe signals in each experiment is 10400.

Table 2 also shows a statistical analysis of the normalized signal ("Spval") calculated on the normalized score. For each miRNA, we used a relevant control group out of the full predicted miRNA list. Each miRNA has an internal control of probes with mismatches. The relevant control group contained probes with similar C and G percentage (abs diff <5%) in order to have similar Tm. The probe signal P value is the ratio over the relevant control group probes with the same or higher signals. The results are p-value ≤0.05 and score is above 500. In those cases that the SPVal is listed as 0.0, the value is less than 0.0001.

2. Expression Analysis—Set 2

To further confirm the hairpins and miRNAs predicted in Example 1, we detected expression in additional tissues. Table 2 of U.S. Provisional Patent Application No. 60/655,094, the contents of which are incorporated herein by reference, lists expression data of miRNAs by the following: HID: hairpin sequence identifier for sequence set forth in the Sequence Listings of U.S. Provisional Patent Application No. 60/655,094, the contents of which are incorporated herein by reference; MID: miRNA sequence identifier for sequence set forth in the Sequence Listings of U.S. Provisional Patent Application No. 60/655,094, the contents of which are incorporated herein by reference; Tissue: tested tissue; S: chip expression score grade (range=100-65000); Dis. Diff. Exp.: disease related differential expression and the tissue it was tested in; R: ratio of disease related expression (range=0.01-99.99); and abbreviations: Brain Mix A—a mixture of brain tissue that are affected in Alzheimer; Brain Mix B—a mixture of all brain tissues; and Brain SN—Substantia Nigra.

3. Sequencing

To further validate the hairpins ("HID") of the second prediction, a number of miRNAs were validated by sequencing methods similar to those described in U.S. Patent Application No. 60/522,459, Ser. No. 10/709,577 and Ser. No. 10/709,572, the contents of which are incorporated herein by reference. Table 3 shows the hairpins ("HID") that were validated by sequencing a miRNA (MID) in the indicated tissue ("Tissue").

EXAMPLE 4

MiRNAs of Chromosome 19

A group of the validated miRNAs from Example 3 were highly expressed in placenta, have distinct sequence similarity, and are located in the same locus on chromosome 19 (FIG. 2A-2B). These predicted miRNAs are spread along a region of ~100,000 nucleotides in the 19q13.42 locus. This genomic region is devoid of protein-coding genes and seems to be intergenic. Further analysis of the genomic sequence, including a thorough examination of the output of our prediction algorithm, revealed many more putative related miRNAs, and located mir-371, mir-372, and mir-373 approximately 25,000 bp downstream to this region. Overall, 54 putative miRNA precursors were identified in this region. The miRNA precursors can be divided into four distinct types of related sequences (FIGS. 2A-2B). About 75% of the miRNAs in the cluster are highly related and were labeled as type A. Three other miRNA types, types B, C and D, are composed of 4, 2, and 2 precursors, respectively. An additional 3 putative miRNA precursors (S1 to S3) have unrelated sequences. Interestingly, all miRNA precursors are in the same orientation as the neighboring mir-371, mir-372, and mir-373 miRNA precursors.

Further sequence analysis revealed that the majority of the A-type miRNAs are embedded in a ~600 bp region that is repeated 35 times in the cluster. The repeated sequence does not appear in other regions of the genome and is conserved only in primates. The repeating unit is almost always bounded by upstream and downstream Alu repeats. This is in sharp contrast to the MC14-1 cluster which is extremely poor in Alu repeats.

FIG. 3A shows a comparison of sequences of the 35 repeat units containing the A-type miRNA precursors in human. The comparison identified two regions exhibiting the highest sequence similarity. One region includes the A-type miRNA, located in the 3' region of the repeat. The second region is located ~100 nucleotides upstream to the A-type miRNA precursors. However, the second region does not show high similarity among the chimp repeat units while the region containing the A-type miRNA precursors does (FIG. 3B).

Examination of the region containing the A-type repeats showed that the 5' region of the miRNAs encoded by the 5' stem of the precursors (5p miRNAs) seem to be more variable than other regions of the mature miRNAs. This is matched by variability in the 3' region of the mature miRNAs derived from the 3' stems (3p miRNAs). As expected, the loop region is highly variable. The same phenomenon can also be observed in the multiple sequence alignment of all 43 A-type miRNAs (FIGS. 4A-4C).

The multiple sequence alignment presented in FIGS. 4A-4C revealed the following findings with regards to the predicted mature miRNAs. The 5p miRNAs can be divided into 3 blocks. Nucleotides 1 to 6 are C/T rich, relatively variable, and are marked in most miRNAs by a CTC motif in nucleotides 3 to 5. Nucleotides 7 to 15 are A/G rich and apart from nucleotides 7 and 8 are shared among most of the miRNAs. Nucleotides 16 to 23 are C/T rich and are, again, conserved among the members. The predicted 3p miRNAs, in general, show a higher conservation among the family members. Most start with an AAA motif, but a few have a different 5' sequence that may be critical in their target recognition. Nucleotides 8 to 15 are C/T rich and show high conservation. The last 7 nucleotides are somewhat less conserved but include a GAG motif in nucleotides 17 to 19 that is common to most members.

Analysis of the 5' region of the repeated units identified potential hairpins. However, in most repeating units these hairpins were not preserved and efforts to clone miRNAs from the highest scoring hairpins failed. There are 8 A-type precursors that are not found within a long repeating unit. Sequences surrounding these precursors show no similarity to the A-type repeating units or to any other genomic sequence. For 5 of these A-type precursors there are Alu repeats located significantly closer downstream to the A-type sequence.

The other miRNA types in the cluster showed the following characteristics. The four B group miRNAs are found in a repeated region of ~500 bp, one of which is located at the end of the cluster. The two D-type miRNAs, which are ~2000 nucleotides from each other, are located at the beginning of the cluster and are included in a duplicated region of 1220 nucleotides. Interestingly, the two D-type precursors are identical. Two of the three miRNAs of unrelated sequence, S1 and S2, are located just after the two D-type miRNAs, and the third is located between A34 and A35. In general, the entire ~100,000 nucleotide region containing the cluster is covered with repeating elements. This includes the miRNA-containing repeating units that are specific to this region and the genome wide repeat elements that are spread in the cluster in large numbers.

EXAMPLE 5

Cloning of Predicted MiRNAs

To further validate the predicted miRNAs, a number of the miRNAs described in Example 4 were cloned using methods similar to those described in U.S. Patent Application No. 60/522,459, Ser. No. 10/709,577 and Ser. No. 10/709,572, the contents of which are incorporated herein by reference. Briefly, a specific capture oligonucleotide was designed for each of the predicted miRNAs. The oligonucleotide was used to capture, clone, and sequence the specific miRNA from a placenta-derived library enriched for small RNAs.

We cloned 41 of the 43 A-type miRNAs, of which 13 miRNAs were not present on the original microarray but only computationally predicted, as well as the D-type miRNAs. For 11 of the predicted miRNA precursors, both 5p and 3p predicted mature miRNAs were present on the microarray and in all cases both gave significant signals. Thus, we attempted to clone both 5' and 3' mature miRNAs in all cloning attempts. For 27 of the 43 cloned miRNA, we were able to clone miRNA derived from both 5' and 3' stems. Since our cloning efforts were not exhaustive, it is possible that more of the miRNA precursors encode both 5' and 3' mature miRNAs.

Many of the cloned miRNAs have shown heterogeneity at the 3' end as observed in many miRNA cloning studies (Lagos-Quintana 2001, 2002, 2003) (Poy 2004). Interestingly, we also observed heterogeneity at the 5' end for a significant number of the cloned miRNAs. This heterogeneity seemed to be somewhat more prevalent in 5'-stem derived miRNAs (9) compared to 3'-stem derived miRNAs (6). In comparison, heterogeneity at the 3' end was similar for both 3' and 5'-stem derived miRNAs (19 and 13, respectively). The 5' heterogeneity involved mainly addition of one nucleotide, mostly C or A, but in one case there was an addition of 3 nucleotides. This phenomenon is not specific to the miRNAs in the chromosome 19 cluster. We have observed it for many additional cloned miRNAs, including both known miRNAs as well as novel miRNAs from other chromosomes (data not shown).

EXAMPLE 6

Analysis of MiRNA Expression

To further examine the expression of the miRNAs of Example 4, we used Northern blot analysis to profile miRNA expression in several tissues. Northern blot analysis was performed using 40 µg of total RNA separated on 13% denaturing polyacrylamide gels and using 32P end labeled oligonucleotide probes. The oligonucleotide probe sequences were 5' ACTCTAAAGAGAAGCGCTTTGT-3' (SEQ ID NO: 5) (A19-3p, NCBI: HSA-MIR-RG-21) and 5' ACCCACCAAAGAGAAGCACTTT-3' (SEQ ID NO:6) (A24-3p, NCBI: HSA-MIR-RG-27). The miRNAs were expressed as ~22 nucleotide long RNA molecules with tissue specificity profile identical to that observed in the microarray analysis (FIG. 5A).

Figure 5B:
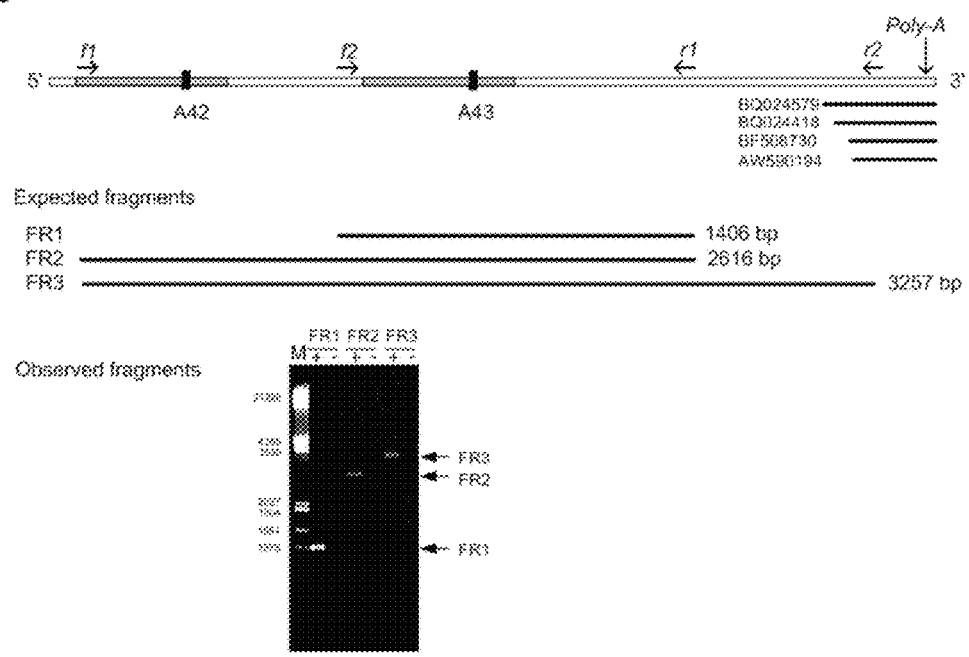
Figure 5C:
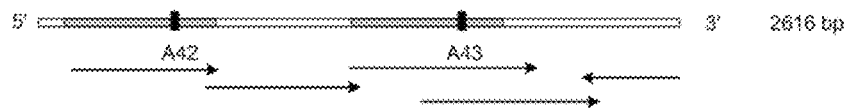

In order to determine how the MC19-1 cluster is transcribed. A survey of the ESTs in the region identified only one place that included ESTs with poly-adenylation signal and poly-A tail. This region is located just downstream to the A43 precursor. The only other region that had ESTs with poly-adenylation signal is located just after mir-373, suggesting that mir-371,2,3 are on a separate transcript. We performed initial studies focusing on the region around mir-A43 to ensure that the region is indeed transcribed into poly-adenylated mRNA. RT-PCR experiments using primers covering a region of 3.5 kb resulted in obtaining the expected fragment (FIG. 5B). RT-PCR analysis was performed using 5 μg of placenta total RNA using oligo-dT as primer. The following primers were used to amplify the transcripts:

```
f1: 5'-GTCCCTGTACTGGAACTTGAG-3';      (SEQ ID NO: 7)

f2: 5'-GTGTCCCTGTACTGGAACGCA-3';     (SEQ ID NO: 8)

r1: 5'-GCCTGGCCATGTCAGCTACG-3';       (SEQ ID NO: 9)

r2: 5'-TTGATGGGAGGCTAGTGTTTC-3';     (SEQ ID NO: 10)

r3: 5' GACGTGGAGGCGTTCTTAGTC-3';     (SEQ ID NO: 11)
and r4: 5'-TGACAACCGTTGGGGATTAC-3'.      (SEQ ID NO: 12)
```

The authenticity of the fragment was validated by sequencing. This region includes mir-A42 and mir-A43, which shows that both miRNAs are present on the same primary transcript.

Further information on the transcription of the cluster came from analysis of the 77 ESTs located within it. We found that 42 of the ESTs were derived from placenta. As these ESTs are spread along the entire cluster, it suggested that the entire cluster is expressed in placenta. This observation is in-line with the expression profile observed in the microarray analysis. Thus, all miRNAs in the cluster may be co-expressed, with the only exception being the D-type miRNAs which are the only miRNAs to be expressed in HeLa cells. Interestingly, none of the 77 ESTs located in the region overlap the miRNA precursors in the cluster. This is in-line with the depletion of EST representation from transcripts processed by Drosha.

Examination of the microarray expression profile revealed that miRNAs D1/2, A12, A21, A22, and A34, have a somewhat different expression profile reflected as low to medium expression levels in several of the other tissues examined. This may be explained by alternative splicing of the transcript(s) encoding the miRNAs or by the presence of additional promoter(s) of different tissues specificity along the cluster.

Comparison of the expression of 3p and 5p mature miRNAs revealed that both are expressed for many miRNA precursors but in most cases at different levels. For most pre-miRNAs the 3p miRNAs are expressed at higher levels then the 5p miRNAs. However, in 6 cases (mir-D1,2, mir-A1, mir-A8, mir-A12, mir-A17 and mir-A33) both 3p and 5p miRNAs were expressed at a similar level, and in one case (mir-A32) the 5p miRNA was expressed at higher levels then the 3p miRNA.

EXAMPLE 7

Conservation

Comparison of the sequences from all four types of predicted miRNAs of Example 4 to that of other species (chimp, macaque, dog, chicken, mouse, rat, drosophila, zebra-fish, fungi, c. elegans) revealed that all miRNAs in the cluster, and in fact the entire region, are not conserved beyond primates. Interestingly, homologues of this region do not exist in any other genomes examined, including mouse and rat. Thus, this is the first miRNA cluster that is specific to primates and not generally shared in mammals. Homology analysis between chimp and human show that all 35 repeats carrying the A-type miRNAs are contiguous between the two species. Furthermore, the entire cluster seems to be identical between human and chimp. Thus, the multiple duplications leading to the emergence of the MC19-1 cluster must have occurred prior to the split of chimp and human and remained stable during the evolution of each species. It should be noted that human chromosome 19 is known to include many tandemly clustered gene families and large segmental duplications (Grimwood et al, 2004). Thus, in this respect the MC19-1 cluster is a natural part of chromosome 19.

In comparison, the MC14-1 cluster is generally conserved in mouse and includes only the A7 and A8 miRNAs within the cluster are not conserved beyond primates (Seitz 2004). In contrast all miRNAs in the MC19-1 cluster are unique to primates. A survey of all miRNAs found in Sanger revealed that only three miRNA, mir-198, mir-373, and mir-422a, are not conserved in the mouse or rat genomes, however, they are conserved in the dog genome and are thus not specific to primates. Interestingly, mir-371 and mir-372, which are clustered with mir-373, and are located 25 kb downstream to the MC19-1 cluster, are homologous to some extent to the A-type miRNAs (FIGS. 4A-4C), but are conserved in rodents.

Comparison of the A-type miRNA sequences to the miRNAs in the Sanger database revealed the greatest homology to the human mir-302 family (FIG. 4C). This homology is higher than the homology observed with mir-371,2,3. The mir-302 family (mir-302a, b, c, and d) are found in a tightly packed cluster of five miRNAs (including mir-367) covering 690 nucleotides located in the antisense orientation in the first intron within the protein coding exons of the HDCMA18P gene (accession NM_016648). No additional homology, apart from the miRNA homology, exists between the mir-302 cluster and the MC19-1 cluster. The fact that both the mir-371,2,3 and mir-302a,b,c,d are specific to embryonic stem cells is noteworthy.

EXAMPLE 8

Differential Expression of miRNAs

Using chip expression methods similar to those described in 0, microarray images were analyzed using Feature Extraction Software (Version 7.1.1, Agilent). Table 2 shows the ratio of disease related expression ("R") compared to normal tissues. Table 2 also shows the statistical analysis of the normalized signal ("RPval"). The signal of each probe was set as its median intensity. Signal intensities range from background level of 400 to saturating level of 66000. 2 channels hybridization was performed and Cy3 signals were compared to Cy5 signals, where fluor reversed chip was preformed (normal vs. disease), probe signal was set to be its average signal. Signals were normalized by dividing them with the known miRNAs average signals such that the sum of known miRNAs signal is the same in each experiment or channel. Signal ratios between disease and normal tissues were calculated. Signal ratio greater than 1.5 indicates a significant upregulation with a P value of 0.007 and signal ratio greater than 2 has P value of 0.003. P values were estimated based on the occurrences of such or greater signal ratios over duplicated experiments.

The differential expression analysis in Table 2 indicates that the expression of a number of the miRNAs are significantly altered in disease tissue. In particular, the MC19-1 miRNAs of Example 4 are differentially expressed in prostate and lung cancer. The relevance of the MC19-1 miRNAs to cancer is supported by the identification of a loss of heterozygosity within the MC19-1 region in prostate cancer derived cells (Dumur et al. 2003).

TABLE 1

HAIRPINS AND MICRORNAS

| HID | Hairpin Loc | C | T | MID | P | Pval | E | S | D | F | LC | SC |
|---|---|---|---|---|---|---|---|---|---|---|---|---|
| 778 | 3+44130716 | Y | G | 8545 | 0.46 | 0.0101 | Y | N | Y | Y | | 1154 |
| 778 | 3+44130716 | Y | G | 8546 | 0.46 | 0.0101 | N | N | N | N | | 1155 |
| 778 | 3+44130716 | Y | G | 8547 | 0.46 | 0.0101 | N | Y | N | N | | 6 |

TABLE 2

EXPRESSION AND DIFFERENTIAL EXPRESSION IN DISEASES OF MICRORNAS

| HID | MID | Tissue | S | SPval | Disease | R | RPval |
|---|---|---|---|---|---|---|---|
| 778 | 8545 | 10 | 589 | 0.0104 | | | |
| 778 | 8545 | 11 | 91177 | 0 | | | |
| 778 | 8545 | 7 | 6175 | 0 | | | |
| 778 | 8545 | 9 | 957 | 0.0052 | | | |
| 778 | 8545 | 13 | 7047 | 0 | | | |
| 778 | 8545 | 12 | 1813 | 0.0078 | | | |
| 778 | 8545 | 5 | 936 | 0.007 | | | |
| 778 | 8545 | | | | 1 | 1.62 | 0.0068 |
| 778 | 8545 | | | | 2 | 0.43 | 0.0053 |
| 778 | 8545 | 10 | 627 | 0.0078 | | | |
| 778 | 8545 | 11 | 205621 | 0 | | | |
| 778 | 8545 | 7 | 6818 | 0 | | | |
| 778 | 8545 | 9 | 1029 | 0.0035 | | | |
| 778 | 8545 | 13 | 7911 | 0 | | | |
| 778 | 8545 | 12 | 2091 | 0.0078 | | | |
| 778 | 8545 | 5 | 1019 | 0.0052 | | | |
| 778 | 8545 | | | | 1 | 1.64 | 0.0067 |
| 778 | 8545 | | | | 2 | 0.39 | 0.005 |
| 778 | 8545 | 10 | 589 | 0.0104 | | | |
| 778 | 8545 | 7 | 6175 | 0 | | | |
| 778 | 8545 | 9 | 957 | 0.0052 | | | |
| 778 | 8545 | 13 | 7047 | 0 | | | |
| 778 | 8545 | 12 | 1813 | 0.0078 | | | |
| 778 | 8545 | 5 | 936 | 0.007 | | | |
| 778 | 8545 | | | | 1 | 1.62 | 0.0068 |
| 778 | 8545 | | | | 2 | 0.43 | 0.0053 |

TABLE 3

SEQUENCED MICRORNAS

| HID | MID | Tissue |
|---|---|---|
| 778 | 8547 | 11 |

TABLE 4

TARGET GENES AND BINDING SITES

| HID | MID | Target Genes and Binding Sites |
|---|---|---|
| 778 | 8545 | ARL10B (109601, 109602); ARNT2 (109611, 109612); CCT5 (109603, 109604); DIRAS1 (109622, 109623); EPHA8 (109599, 109600); GPR124 (109605, 109606, 109607); IXL (109620, 109621); NFIX (109617, 109618, 109619); PCOLN3 (109613, 109614); RARA (109615, 109616); SYT13 (109608, 109609, 109610); |
| 778 | 8546 | C2orf26 (109628, 109629); CHML (109626, 109627); DGKI (109632, 109633); EFCBP1 (109634, 109635); EFNB3 (109636, 109637); FLJ20160 (109630, 109631); HRNR (109624, 109625); |
| 778 | 8547 | 13CDNA73 (109805); AASDHPPT (109783); ABCA6 (109844); ABI1 (109774); ACACA (109840); ADARB1 (109863); ADCY2 (109718); AEBP2 (109792); ALS2CR3 (109679); ANKH (109724); ANP32E (109653); AP1G1 (109830); ARHGAP18 (109743); ARL6IP5 (109688); ATOH7 (109777); ATP11A (109808); ATP11C (109876); ATP2B3 (109871); ATXN10 (109865); BBS5 (109669); BCL2L14 (109791); BID (109866); BLP1 (109754); BRPF3 (109733); BRUNOL6 (109823); C10orf26 (109770); C12orf22 (109799); C13orf25 (109806); C1orf21 (109647); C20orf7 (109859); C6orf198 (109744); C9orf28 (109760); CCND2 (109790); CCPG1 (109822); CD22 (109851); CD2AP (109735); CD80 (109700); CDC2L6 (109740); CDCA5 (109787); CDH13 (109827); CHRFAM7A (109821); CIR (109678); CLEC1A (109798); CNTNAP5 (109667); COL4A6 (109873); COMMD3 (109764); CRI2 (109855); CRISPLD2 (109828); CSPG3 (109849); CTSS (109654); CYP3A7 (109750); CYP4F3 (109848); DDAH2 (109739); DDX19L (109826); DDX3Y (109877); DHFR (109725); DKFZp564J157 (109794); DKK2 (109714); DLEU7 (109809); DMXL1 (109720); DPP9 (109854); DUSP3 (109842); DYM (109847); E2F7 (109802); E2IG5 (109689); EAF1 (109682); ECHDC1 (109742); EFHA2 (109751); ENPEP (109707); EPB41L1 (109860); ERBB4 (109680); ESCO1 (109846); FAHD1 (109824); FARP2 (109674); FCHSD1 (109728); FCRL2 (109645); FIP1L1 (109704); FLJ35775 (109755); FPRL2 (109852); FSTL5 (109716); FXC1 (109779); GCET2 (109698); GDAP1L1 (109861); GDF6 (109757); GHR (109719); GMFB (109814); GNPNAT1 (109813); GORASP1 (109694); GOSR1 (109833); GP5 (109703); GPC3 (109875); GREM2 (109658); HAN11 (109836); HECA (109736); HLCS (109864); HPS3 (109691); HRB (109673); HS2ST1 (109643); HSXIAPAF1 (109832); hSyn (109796); IHPK1 (109696); IL8RB (109672); INA (109771); ING1 (109807); IQCC (109639); IRF4 (109732); ISGF3G (109810); ISLR (109818); IVD (109817); JAGN1 (109681); JMJD1C (109776); KA36 (109841); KAB (109659); KCNJ2 (109837); KIAA0478 (109638); KIAA0553 (109843); KIAA1078 (109648); KIAA1463 (109793); KIAA1609 (109831); KIAA1712 (109709); KIAA1729 (109711); KIT |

TABLE 4-continued

TARGET GENES AND BINDING SITES

| HID | MID | Target Genes and Binding Sites |
|---|---|---|
| | | (109705); KLHL4 (109870); KLHL8 (109712); LDB3 (109768); LOC340156 (109737); LPXN (109786); LRP2BP (109717); LRPPRC (109676); LRRTM2 (109727); LUZP1 (109651); MAGEB4 (109869); MAGEB6 (109868); MAK3 (109699); MARVELD1 (109769); MEGF10 (109722); MGC51082 (109856); MLLT2 (109706); MOBKL2B (109763); MRFAP1L1 (109710); MXI1 (109772); MYO1D (109839); MYST2 (109834); NAP1L1 (109801); NAP1L5 (109713); NARG1 (109708); NAV1 (109649); NBS1 (109756); NCKIPSD (109695); NEU3 (109781); NFX1 (109759); NIN (109812); NIPA1 (109819, 109820); NKTR (109685, 109686); NMNAT2 (109655); NSUN4 (109640); NUDT13 (109767); NUDT16 (109690); OXSR1 (109684); P2RY1 (109692); PAK7 (109862); PCAF (109683); PDE10A (109745); PDE5A (109715); PDE6A (109729); PDK1 (109670); PDPR (109825); PHF20L1 (109753); PHYHIPL (109766); PLAA (109762); PLCB1 (109858); PLEKHK1 (109775); POLQ (109701); POMZP3 (109748); PRKCE (109661); PRKG1 (109765); PRSS23 (109782); PSD4 (109665); PTGFR (109642); PTPN11 (109797); RAB3GAP (109668); RAB4A (109650); RAB6A (109788); RALB (109666); RALGPS1 (109761); RANBP9 (109738); RAP2B (109693); RASGRP3 (109660); RIOK3 (109845); RIPK5 (109657); RPIA (109662); SAMD12 (109758); SAMD9 (109749); SEPT6 (109874); SFRS11 (109641); SFXN5 (109677); SGCD (109723); SLC25A16 (109778); SLC25A27 (109734); SLC36A2 (109730); SLC5A7 (109664); SLICK (109656); SLITRK3 (109702); SMC1L1 (109872); SMC6L1 (109675); SNX24 (109721); SPARC (109731); SPOCK (109726); SPRED1 (109816); STAT2 (109800); STXBP4 (109835); TBC1D15 (109795); TBRG1 (109784); TDE2 (109741); THUMPD1 (109829); TMCC3 (109803); TRAPPC6B (109811); TRIM68 (109785); TUBAL3 (109773); TUFT1 (109644); UCP3 (109789); UHMK1 (109646); UNC5D (109752); VGL-3 (109697); WARS2 (109652); XBP1 (109867); ZAK (109671); ZFYVE1 (109815); ZNF160 (109857); ZNF2 (109663); ZNF215 (109780); ZNF507 (109850); ZNF528 (109853); ZNF588 (109746); ZNF605 (109804); ZNF624 (109838); ZNF660 (109687); ZNF92 (109747); |

TABLE 30

| HID | MID | Dis | N | T | Per. | Pval | Target Gene Names |
|---|---|---|---|---|---|---|---|
| 778 | 8547 | 183 | 1 | 3 | 33.3 | 0.0493 | KIT |
| 778 | 8547 | 69 | 1 | 3 | 33.3 | 0.0493 | SPARC |
| 778 | 8547 | 176 | 2 | 12 | 16.7 | 0.0164 | CDH13, PDE5A |

TABLE 6

RELATION OF MICRORNAS TO DISEASES BY HOST GENES

| HID | MID | H. Gene | Disease(s) |
|---|---|---|---|
| 31 | 7030, 7029 | CDH6 | 167, 157 |
| 39 | 7046, 7045 | PAK1 | 31 |
| 42 | 7052, 7051 | MAPK8IP1 | 64 |
| 99 | 7166, 7165 | ITGB3 | 172, 171, 118, 127, 154, 41, 67, 92, 53, 40, 111, 51, 102 |
| 103 | 7174, 7173 | GRM7 | 162 |
| 125 | 7219, 7218 | MOBP | 123 |
| 127 | 7223, 7222 | PBX1 | 109 |
| 128 | 7225, 7224 | MUC1 | 110, 133, 31 |
| 189 | 7347, 7346 | MYO7A | 60 |
| 191 | 7351, 7350 | CDH13 | 31, 176, 133, 110, 51, 167 |
| 212 | 7396, 7395 | PAH | 162 |
| 224 | 7420, 7419 | TBXA2R | 110, 133, 18 |
| 232 | 7438, 7437 | NR3C2 | 57, 98 |
| 239 | 7454, 7453 | IL16 | 112, 56, 92, 160, 18 |
| 243 | 7462, 7461 | NRG1 | 31, 162, 154, 8, 123 |
| 246 | 7468, 7467 | ERBB4 | 31, 51, 154 |
| 267 | 7512, 7511 | CCND3 | 31, 122, 35, 118, 112, 109 |
| 291 | 7568, 7567 | ALCAM | 118 |
| 293 | 7572, 7571 | DAB1 | 162 |
| 301 | 7588, 7587 | PAM | 154, 123, 110 |
| 311 | 7610, 7609 | GRIA4 | 82, 77, 8 |
| 338 | 7664, 7663 | SLC1A3 | 82, 8 |
| 355 | 7698, 7697 | NRP2 | 36 |
| 363 | 7714, 7713 | PTPN6 | 31, 112, 109, 93, 35 |
| 364 | 7716, 7715 | GOLGA5 | 173 |
| 375 | 7739, 7738 | HTR2C | 162, 29, 120 |
| 390 | 7769, 7768 | COL2A1 | 135, 60 |
| 396 | 7781, 7780 | MLLT2 | 109 |

TABLE 6-continued

RELATION OF MICRORNAS TO DISEASES BY HOST GENES

| HID | MID | H. Gene | Disease(s) |
|---|---|---|---|
| 410 | 7809, 7808 | TGFBR3 | 31 |
| 450 | 7888, 7887 | GRIK2 | 82 |
| 466 | 7920, 7919 | TIAM1 | 157, 70, 31 |
| 480 | 7948, 7947 | LAMB1 | 154, 51 |
| 481 | 7950, 7949 | SEMA3F | 110 |
| 482 | 7952, 7951 | PMS2 | 118, 79, 51, 154, 151 |
| 505 | 7998, 7997 | EPS15 | 109 |
| 506 | 8000, 7999 | ST7 | 51, 31, 24, 90, 83 |
| 560 | 8108, 8107 | CDH13 | 31, 176, 133, 110, 51, 167 |
| 588 | 8164, 8163 | HK2 | 134, 132, 64 |
| 616 | 8219, 8218 | CYLD | 166, 157 |
| 621 | 8229, 8228 | CHRNA7 | 144, 8, 24, 162 |
| 626 | 8239, 8238 | IL15 | 167, 110, 31, 92 |
| 631 | 8249, 8248 | PTN | 118, 31, 167, 154, 141, 133 |
| 633 | 8253, 8252 | PAH | 162 |
| 634 | 8255, 8254 | ERBB4 | 31, 51, 154 |
| 648 | 8283, 8282 | AMPH | 31 |
| 654 | 8295, 8294 | EGFR | 51, 31, 167, 133, 110 |
| 669 | 8325, 8324 | PTHR1 | 136 |
| 680 | 8348, 8347 | HOXC4 | 166, 157, 27 |
| 681 | 8350, 8349 | MLLT4 | 109 |
| 682 | 8352, 8351 | RANBP17 | 109 |
| 683 | 8354, 8353 | ATP6V1B1 | 158 |
| 689 | 8366, 8365 | NRP2 | 36 |
| 710 | 8410, 8409 | TNC | 118, 110, 98, 31, 180, 154, 79, 51 |
| 714 | 8418, 8417 | TPO | 60, 174, 102, 61 |
| 727 | 8444, 8443 | MLLT2 | 109 |
| 731 | 8452, 8451 | FHIT | 133, 110, 42, 31 |
| 744 | 8478, 8477 | DSTN | 8 |
| 780 | 8551, 8550 | S100A1 | 157 |
| 800 | 8591, 8590 | ITGA5 | 51, 35, 155, 112, 109, 90, 133, 122, 118 |
| 803 | 8597, 8596 | MLLT3 | 109 |
| 813 | 8617, 8616 | PTPRG | 157, 110, 31 |
| 823 | 8637, 8636 | MAP2K5 | 154 |
| 830 | 8651, 8650 | SCN5A | 185, 34 |
| 838 | 8667, 8666 | GABRA3 | 82, 29, 47, 123 |
| 839 | 8669, 8668 | PTPRN | 64, 105, 85 |
| 861 | 8713, 8712 | FGFR2 | 79, 31, 30, 154 |
| 897 | 8785, 8784 | TJP2 | 51, 31, 154 |
| 925 | 8845, 8844 | CYP11B2 | 98 |
| 935 | 8865, 8864 | LPP | 110, 109 |
| 945 | 8885, 8884 | EPHB2 | 167 |
| 982 | 8958, 8957 | ALK | 112, 93 |
| 1029 | 9052, 9051 | TACR1 | 92, 56, 120, 18, 103, 160, 141 |
| 1031 | 9056, 9055 | SCN5A | 185, 34 |
| 1037 | 9068, 9067 | EIF4A1 | 118, 90 |
| 1053 | 9100, 9099 | GRIA4 | 82, 77, 8 |
| 1069 | 9132, 9131 | WNT3A | 122 |
| 1086 | 9168, 9167 | BCL11A | 112, 109, 93 |
| 1103 | 9202, 9201 | TP73L | 26, 42, 30, 27, 83, 51, 48, 166, 110 |
| 1115 | 9226, 9225 | GRIN2B | 162, 77, 8 |
| 1125 | 9246, 9245 | BIK | 31 |
| 1132 | 9260, 9259 | GRIA2 | 8, 77, 82, 162 |
| 1138 | 9272, 9271 | GLDC | 96 |
| 1139 | 9274, 9273 | PRKCD | 157, 154 |
| 1153 | 9302, 9301 | GPC3 | 31, 90 |
| 1181 | 9361, 9360 | RPS6KB1 | 31 |
| 1241 | 9481, 9480 | ITGA3 | 31, 154, 118, 79, 51 |
| 1253 | 9505, 9504 | ROBO1 | 31, 157, 110 |
| 1259 | 9517, 9516 | MEIS1 | 109 |
| 1264 | 9527, 9526 | RORA | 154, 31 |
| 1291 | 9581, 9580 | IGF1 | 60, 133, 31, 51, 67, 110, 92, 105, 64, 132 |
| 1297 | 9593, 9592 | CACNA2D2 | 133 |
| 1298 | 9595, 9594 | DAB1 | 162 |
| 1299 | 9597, 9596 | NTRK3 | 116, 8, 109, 157 |
| 1319 | 9637, 9636 | CDH17 | 109 |
| 1345 | 9689, 9688 | CDH23 | 60 |
| 1353 | 9705, 9704 | DLEU2 | 109 |
| 1362 | 9723, 9722 | PTPRG | 157, 110, 31 |
| 1367 | 9733, 9732 | TPK1 | 117 |
| 1377 | 9753, 9752 | SOAT1 | 134 |
| 1385 | 9769, 9768 | ADCY2 | 8 |
| 1390 | 9779, 9778 | ERCC5 | 110 |
| 1413 | 9826, 9825 | AUTS2 | 24 |
| 1427 | 9854, 9853 | CYP19A1 | 31, 90, 79, 154 |
| 1435 | 9870, 9869 | PTPRF | 134, 31 |

TABLE 6-continued

RELATION OF MICRORNAS TO DISEASES BY HOST GENES

| HID | MID | H. Gene | Disease(s) |
|---|---|---|---|
| 1513 | 10029, 10028 | ABCA4 | 113 |
| 1518 | 10039, 10038 | ITGA3 | 31, 154, 118, 79, 51 |
| 1520 | 10043, 10042 | NGFR | 31, 8, 92, 144, 123 |
| 1524 | 10051, 10050 | CALCR | 160, 136, 31 |
| 1541 | 10084, 10083 | ST7 | 51, 31, 24, 90, 83 |
| 1542 | 10086, 10085 | PTPRF | 134, 31 |
| 1547 | 10096, 10095 | PTOV1 | 154 |
| 1606 | 10224, 10223 | GPC3 | 31, 90 |
| 1643 | 10298, 10297 | F13A1 | 48, 56, 49 |
| 1662 | 10338, 10337 | CD8B1 | 92 |
| 1663 | 10340, 10339 | HIP1 | 51, 154, 109 |
| 1671 | 10356, 10355 | AUTS2 | 24 |
| 1715 | 10444, 10443 | UBE3A | 24 |
| 1753 | 10520, 10519 | ADAM12 | 109, 90, 47, 134, 122, 112 |
| 1766 | 10546, 10545 | NSF | 162 |
| 1771 | 10556, 10555 | LPP | 110, 109 |
| 1776 | 10566, 10565 | SDC2 | 24 |
| 1801 | 10619, 10618 | IGF1R | 110, 154, 118, 31 |
| 1812 | 10641, 10640 | IL15 | 167, 110, 31, 92 |
| 1866 | 10749, 10748 | HMGA2 | 79, 110 |
| 1877 | 10771, 10770 | GRIK2 | 82 |
| 1879 | 10775, 10774 | RORA | 154, 31 |
| 1890 | 10799, 10798, 10797, 10796 | EIF4A2 | 88, 112 |
| 1900 | 10819, 10818 | SREBF2 | 134, 95, 51, 154 |
| 1911 | 10841, 10840 | ELAVL4 | 167 |
| 1915 | 10849, 10848 | MTAP | 110, 109, 133 |
| 1932 | 10884, 10883 | HOXC5 | 112, 42 |
| 1950 | 10920, 10919 | WWOX | 122, 83, 31 |
| 1958 | 10936, 10935 | CALCR | 160, 136, 31 |
| 1973 | 10968, 10967 | TGIF | 83 |
| 2008 | 11038, 11037 | GYPC | 114 |
| 2009 | 11040, 11039 | GYPC | 114 |
| 2028 | 11078, 11077 | CSEN | 8 |
| 2037 | 11096, 11095 | FYN | 112, 109, 92, 157 |
| 2125 | 11275, 11274 | NISCH | 98 |
| 2142 | 11309, 11308 | TMEFF2 | 154, 51, 30 |
| 2146 | 11317, 11316 | HLA-DRB5 | 109, 105, 64, 123 |
| 2149 | 11325, 11324 | GNAO1 | 8 |
| 2156 | 11340, 11339 | FLT4 | 110, 31, 90, 109, 112, 154, 133, 51 |
| 2182 | 11403, 11402 | HTR2C | 162, 29, 120 |
| 2210 | 11461, 11460 | IMP-1 | 51, 31 |
| 2232 | 11507, 11506 | TPK1 | 117 |
| 2265 | 11573, 11572 | CSEN | 8 |
| 2268 | 11579, 11578 | CASP8 | 8, 167, 157, 92, 51, 31, 133, 110 |
| 2269 | 11581, 11580 | COL4A2 | 157, 154 |
| 2281 | 11605, 11604 | VWF | 64, 53, 31, 105, 103, 92, 132 |
| 2283 | 11609, 11608 | KCNH1 | 42, 31 |
| 2285 | 11613, 11612 | BIK | 31 |
| 2287 | 11617, 11616 | PTPRG | 157, 110, 31 |
| 2340 | 11723, 11722 | CRKL | 109 |
| 2379 | 11804, 11803 | CTNNBIP1 | 51, 118 |
| 2399 | 11844, 11843 | RANBP17 | 109 |
| 2412 | 11870, 11869 | ERBB4 | 31, 51, 154 |
| 2417 | 11886, 11885 | GPC1 | 31 |
| 2431 | 11914, 11913 | ROBO1 | 31, 157, 110 |
| 2451 | 11954, 11953 | SCN5A | 185, 34 |
| 2473 | 11998, 11997 | ABAT | 162 |
| 2480 | 12012, 12011 | CEACAM5 | 31, 110, 133, 51 |
| 2482 | 12016, 12015 | TP73 | 118, 112, 110, 51, 35, 31, 109, 90, 59 |
| 2494 | 12043, 12042 | PBX1 | 109 |
| 2498 | 12051, 12050 | MECP2 | 24, 133 |
| 2517 | 12089, 12088 | PRKCG | 31, 8, 154, 51 |
| 2538 | 12131, 12130 | TUB | 134 |
| 2543 | 12141, 12140 | ST7 | 51, 31, 24, 90, 83 |
| 2549 | 12153, 12152 | HLF | 109 |
| 2551 | 12157, 12156 | SEMA3F | 110 |
| 2558 | 12171, 12170 | APLP2 | 8 |
| 2583 | 12221, 12220 | RANBP17 | 109 |
| 2589 | 12236, 12235 | NTRK3 | 116, 8, 109, 157 |
| 2595 | 12248, 12247 | C3 | 51, 31, 8, 105, 92, 64, 134, 110 |
| 2615 | 12288, 12287 | GRIK1 | 82, 77, 70, 10 |
| 2636 | 12329, 12328 | PBX1 | 109 |
| 2651 | 12359, 12358 | DLEU2 | 109 |
| 2662 | 12381, 12380 | DAPK1 | 51, 31, 30, 112, 110, 109, 176, 133 |
| 2668 | 12393, 12392 | CDC27 | 118 |
| 2677 | 12411, 12410 | PAH | 162 |

TABLE 6-continued

RELATION OF MICRORNAS TO DISEASES BY HOST GENES

| HID | MID | H. Gene | Disease(s) |
|---|---|---|---|
| 2734 | 12528, 12527 | ALK | 112, 93 |
| 2769 | 12597, 12596 | ED1 | 166, 118 |
| 2781 | 12621, 12620 | GRM7 | 162 |
| 2788 | 12635, 12634 | HDGF | 90, 83 |
| 2808 | 12677, 12676 | DPYD | 30, 157, 106, 83, 51, 31 |
| 2831 | 12727, 12726 | CAST | 98, 63, 8, 160, 111, 109 |
| 2841 | 12747, 12746 | TBX2 | 31 |
| 2853 | 12771, 12770 | CALCR | 160, 136, 31 |
| 2860 | 12785, 12784 | MYH7 | 129, 100 |
| 2861 | 12787, 12786 | AUTS2 | 24 |
| 2881 | 12830, 12829 | SERPINA5 | 172 |
| 2883 | 12834, 12833 | CACNA1G | 109, 51 |
| 2887 | 12842, 12841 | CDH13 | 31, 176, 133, 110, 51, 167 |
| 2892 | 12852, 12851 | ITGA5 | 51, 35, 155, 112, 109, 90, 133, 122, 118 |
| 2917 | 12902, 12901 | MITF | 118, 60 |
| 2918 | 12904, 12903 | DYSF | 129 |
| 2932 | 12932, 12931 | MME | 167, 133, 110, 8 |
| 2938 | 12944, 12943 | RORA | 154, 31 |
| 2943 | 12954, 12953 | ST7 | 51, 31, 24, 90, 83 |
| 2966 | 13000, 12999 | PTPRF | 134, 31 |
| 2973 | 13014, 13013 | KCNQ1 | 60, 21 |
| 2980 | 13028, 13027 | MEIS1 | 109 |
| 2998 | 13064, 13063 | HOXB3 | 109 |
| 3003 | 13074, 13073 | CSEN | 8 |
| 3023 | 13119, 13118 | PPP2R1B | 51, 31, 110 |
| 3039 | 13154, 13153 | DYSF | 129 |
| 3052 | 13180, 13179 | CDH23 | 60 |
| 3056 | 13191, 13190 | ELN | 110 |
| 3105 | 13293, 13292 | AUTS2 | 24 |
| 3172 | 13430, 13429 | AUTS2 | 24 |
| 3178 | 13442, 13441 | OTOF | 60 |
| 3214 | 13514, 13513 | FUT8 | 138, 51 |
| 3222 | 13530, 13529 | HLF | 109 |
| 3227 | 13540, 13539 | TCF4 | 162, 29 |
| 3250 | 13586, 13585 | ACTN4 | 31 |
| 3300 | 13686, 13685 | ACPP | 181, 154, 30 |
| 3308 | 13702, 13701 | AR | 154, 92, 110, 51, 8, 31 |
| 3312 | 13710, 13709 | GLP1R | 132, 64 |
| 3338 | 13762, 13761 | KCNQ1 | 60, 21 |
| 3361 | 13811, 13810 | RORA | 154, 31 |
| 3409 | 13907, 13906 | GRIA3 | 82, 77, 29 |
| 3422 | 13933, 13932 | DDC | 167, 105, 162, 29, 24, 144, 36, 64, 23, 133 |
| 3427 | 13943, 13942 | PTPRG | 157, 110, 31 |
| 3489 | 14066, 14065 | EDNRA | 64, 51, 42, 132, 108, 98, 31, 174, 134 |
| 3504 | 14096, 14095 | COPEB | 154 |
| 3542 | 14173, 14172 | MLLT2 | 109 |
| 3561 | 14211, 14210 | GYPC | 114 |
| 3592 | 14272, 14271 | FKBP5 | 154 |
| 3608 | 14304, 14303 | BCL11A | 112, 109, 93 |
| 3613 | 14318, 14317, 14316 | HTR2C | 162, 29, 120 |
| 3618 | 14328, 14327 | ALCAM | 118 |
| 3684 | 14460, 14459 | ERBB4 | 31, 51, 154 |
| 3693 | 14478, 14477 | ZNFN1A1 | 112, 109 |
| 3754 | 14601, 14600 | EPB41 | 114 |
| 3756 | 14605, 14604 | SLC7A5 | 51 |
| 3778 | 14651, 14650 | SDC2 | 24 |
| 3794 | 14683, 14682 | ST7 | 51, 31, 24, 90, 83 |
| 3803 | 14702, 14701 | WT1 | 31, 133, 110 |
| 3856 | 14808, 14807 | STS | 31 |
| 3878 | 14855 | ADAM12 | 109, 90, 47, 134, 122, 112 |
| 3885 | 14869, 14868 | FGFR2 | 79, 31, 30, 154 |
| 3890 | 14879, 14878 | C3 | 51, 31, 8, 105, 92, 64, 134, 110 |
| 3902 | 14903, 14902 | DLEU2 | 109 |
| 3924 | 14946, 14945 | HOXC8 | 42, 51 |
| 3928 | 14954, 14953 | PTPRN2 | 64, 105 |
| 3929 | 14956, 14955 | HTR2C | 162, 29, 120 |
| 3935 | 14968, 14967 | GNAO1 | 8 |
| 3955 | 15008, 15007 | PRDX1 | 70, 8, 109 |
| 3997 | 15099, 15098 | PRKCA | 51, 31, 150, 110, 64, 8, 132 |
| 4000 | 15106, 15105 | CDH5 | 118 |
| 4006 | 15118, 15117 | RUNX1 | 109, 160 |
| 4014 | 15134, 15133 | GNAO1 | 8 |
| 4020 | 15146, 15145 | AMPH | 31 |
| 4025 | 15156, 15155 | ETS1 | 110, 51, 31 |
| 4059 | 15222, 15221 | APPBP2 | 31 |
| 4069 | 15242, 15241 | MLLT2 | 109 |

TABLE 6-continued

RELATION OF MICRORNAS TO DISEASES BY HOST GENES

| HID | MID | H. Gene | Disease(s) |
|---|---|---|---|
| 4085 | 15274, 15273 | ALK | 112, 93 |
| 4086 | 15276, 15275 | PTN | 118, 31, 167, 154, 141, 133 |
| 4136 | 15376, 15375 | PTPRN2 | 64, 105 |
| 4145 | 15394, 15393 | APBB1 | 144, 8 |
| 4152 | 15408, 15407 | DYSF | 129 |
| 4160 | 15424, 15423 | PLCB1 | 167 |
| 4162 | 15428, 15427 | DPYD | 30, 157, 106, 83, 51, 31 |
| 4171 | 15452, 15451 | MLLT3 | 109 |
| 4179 | 15468, 15467 | ALK | 112, 93 |
| 4211 | 15532, 15531 | TRPM1 | 118 |
| 4217 | 15544, 15543 | IGFBP2 | 64, 31, 51, 132, 110, 105, 134 |
| 4229 | 15568, 15567 | ALK | 112, 93 |
| 4232 | 15574, 15573 | LPP | 110, 109 |
| 4270 | 15653, 15652 | NF1 | 31, 118, 110, 51, 167 |
| 4275 | 15663, 15662 | MGAT5 | 88, 51, 118, 90 |
| 4286 | 15685, 15684 | MST1R | 133, 31, 110, 51 |
| 4289 | 15691, 15690 | NTRK1 | 31, 116, 173, 167, 8 |
| 4300 | 15713, 15712 | FHIT | 133, 110, 42, 31 |
| 4315 | 15743, 15742 | APBA2 | 75, 51, 8 |
| 4323 | 15759, 15758 | CACNA1A | 120, 61 |
| 4344 | 15801, 15800 | GRIA3 | 82, 77, 29 |
| 4352 | 15817, 15816 | COL11A2 | 60 |
| 4360 | 15833, 15832 | RAD51L1 | 110 |
| 4384 | 15885, 15884 | TERT | 110, 51, 31, 133 |
| 4389 | 15895, 15894 | APBA2 | 75, 51, 8 |
| 4391 | 15899, 15898 | TPO | 60, 174, 102, 61 |
| 4401 | 15919, 15918 | TMC1 | 60 |
| 4402 | 15921, 15920 | AK1 | 86 |
| 4406 | 15929, 15928 | MLLT3 | 109 |
| 4410 | 15936 | CDK6 | 133, 51, 31, 167 |
| 4422 | 15960, 15959 | VWF | 64, 53, 31, 105, 103, 92, 132 |
| 4423 | 15962, 15961 | NR3C2 | 57, 98 |
| 4446 | 16008, 16007 | FHIT | 133, 110, 42, 31 |
| 4454 | 16024, 16023 | DCC | 51 |
| 4469 | 16054, 16053 | GRIA2 | 8, 77, 82, 162 |
| 4470 | 16056, 16055 | ATP1A1 | 98, 64, 8, 105 |
| 4472 | 16060, 16059 | PTPRG | 157, 110, 31 |
| 4476 | 16068, 16067 | SCG3 | 154 |
| 4477 | 16070, 16069 | CBFA2T1 | 109 |
| 4480 | 16076, 16075 | FKBP5 | 154 |
| 4498 | 16115 | ERBB4 | 31, 51, 154 |
| 4509 | 16137, 16136 | HOXB3 | 109 |
| 4529 | 16177, 16176 | GRM7 | 162 |
| 4547 | 16213, 16212 | CDX1 | 106, 51 |
| 4587 | 16293, 16292 | SLC7A5 | 51 |
| 4589 | 16297, 16296 | RANBP17 | 109 |
| 4596 | 16311, 16310 | CACNA1A | 120, 61 |
| 4608 | 16335, 16334 | APBA2 | 75, 51, 8 |
| 4618 | 16355, 16354 | NTRK2 | 10, 154, 8, 162 |
| 4619 | 16357, 16356 | OTOF | 60 |
| 4628 | 16375, 16374 | PTPRN2 | 64, 105 |
| 4659 | 16437, 16436 | CACNA1A | 120, 61 |
| 4660 | 16439, 16438 | CUBN | 117 |
| 4672 | 16464, 16463 | MTAP | 110, 109, 133 |
| 4674 | 16468, 16467 | DYSF | 129 |
| 4680 | 16480, 16479 | PTPRN | 64, 105, 85 |
| 4695 | 16510, 16509 | PRKCA | 51, 31, 150, 110, 64, 8, 132 |
| 4706 | 16533, 16532 | KCNH1 | 42, 31 |
| 4711 | 16543, 16542 | GRIA3 | 82, 77, 29 |
| 4714 | 16549, 16548 | GLP1R | 132, 64 |
| 4723 | 16567, 16566 | THRA | 157, 150 |
| 4761 | 16643, 16642 | PSG1 | 70 |
| 4792 | 16706, 16705 | SEMA3F | 110 |
| 4802 | 16729, 16728 | MPZ | 112 |
| 4858 | 16840, 16839 | AUTS2 | 24 |
| 4864 | 16852, 16851 | NF1 | 31, 118, 110, 51, 167 |
| 4866 | 16856, 16855 | RPA1 | 110, 51, 31, 133 |
| 4872 | 16868, 16867 | PTPRN | 64, 105, 85 |
| 4886 | 16896, 16895 | CD3Z | 93, 157, 111 |
| 4897 | 16918, 16917 | MSN | 70, 92, 160 |
| 4898 | 16920, 16919 | GAP43 | 8, 62, 10, 162, 29 |
| 4900 | 16924, 16923 | PAX2 | 157 |
| 4909 | 16942, 16941 | MYH6 | 129, 100 |
| 4919 | 16962, 16961 | HK2 | 134, 132, 64 |
| 4929 | 16982, 16981 | ZNFN1A1 | 112, 109 |
| 4936 | 16996, 16995 | TNC | 118, 110, 98, 31, 180, 154, 79, 51 |

TABLE 6-continued

RELATION OF MICRORNAS TO DISEASES BY HOST GENES

| HID | MID | H. Gene | Disease(s) |
|---|---|---|---|
| 4941 | 17006, 17005 | PLCB1 | 167 |
| 4959 | 17043, 17042 | PTPRF | 134, 31 |
| 5001 | 17130, 17129 | ERBB2 | 110, 133, 154, 26, 176, 167, 51, 31, 30 |
| 5026 | 17183, 17182 | YWHAG | 118 |
| 5037 | 17205, 17204 | KCNN3 | 162, 29 |
| 5040 | 17211, 17210 | DPYD | 30, 157, 106, 83, 51, 31 |
| 5070 | 17272, 17271 | MUC1 | 110, 133, 31 |
| 5079 | 17290, 17289 | CDC10 | 112 |
| 5126 | 17384, 17383 | GRB7 | 83, 31 |
| 5134 | 17400, 17399 | HTR2C | 162, 29, 120 |
| 5139 | 17410, 17409 | ROBO1 | 31, 157, 110 |
| 5143 | 17418, 17417 | GRIA2 | 8, 77, 82, 162 |
| 5166 | 17464, 17463 | ALK | 112, 93 |
| 5174 | 17480, 17479 | CENPF | 90, 31 |
| 5189 | 17510, 17509 | PROS1 | 172 |
| 5231 | 17594, 17593 | CTNND2 | 154 |
| 5263 | 17659, 17658 | BCL9 | 112, 109 |
| 5309 | 17751, 17750 | MLLT3 | 109 |
| 5331 | 17796, 17795 | PTPRF | 134, 31 |
| 5332 | 17798, 17797 | GRIA4 | 82, 77, 8 |
| 5350 | 17834, 17833 | PAPPA | 53, 70 |
| 5363 | 17860, 17859 | GRIN2B | 162, 77, 8 |
| 5406 | 17948, 17947 | SYN2 | 8, 162 |
| 5409 | 17954, 17953 | DYSF | 129 |
| 5504 | 18146, 18145 | ST7 | 51, 31, 24, 90, 83 |
| 5518 | 18174, 18173 | CPB2 | 172, 127 |
| 5556 | 18250, 18249 | MAP2K5 | 154 |
| 5563 | 18264, 18263 | PRKCA | 51, 31, 150, 110, 64, 8, 132 |
| 5603 | 18344, 18343 | MUC1 | 110, 133, 31 |
| 5630 | 18397, 18396 | FMR2 | 84 |
| 5636 | 18409, 18408 | PRDM2 | 90, 51, 79, 31, 112, 110 |
| 5638 | 18413, 18412 | THRB | 157, 154, 150, 133, 31, 167 |
| 5647 | 18433, 18432 | MOBP | 123 |
| 5670 | 18479, 18478 | APBA2 | 75, 51, 8 |
| 5686 | 18511, 18510 | LPA | 52, 8 |
| 5697 | 18535, 18534 | ACTN4 | 31 |
| 5711 | 18567, 18566 | CDH13 | 31, 176, 133, 110, 51, 167 |
| 5721 | 18587, 18586 | SREBF1 | 132, 92, 64, 134 |
| 5725 | 18595, 18594 | SCN5A | 185, 34 |
| 5738 | 18621, 18620 | TCF4 | 162, 29 |
| 5745 | 18635, 18634 | HTR2C | 162, 29, 120 |
| 5765 | 18675, 18674 | CSEN | 8 |
| 5803 | 18754, 18753 | PTPRF | 134, 31 |
| 5820 | 18789, 18788 | FMR2 | 84 |
| 5827 | 18803, 18802 | HOXA3 | 109 |
| 5832 | 18813, 18812 | HSD11B1 | 134 |
| 5833 | 18815, 18814 | GRIN2B | 162, 77, 8 |
| 5869 | 18887, 18886 | HSPG2 | 133, 110, 31, 8 |
| 5890 | 18931, 18930 | DAB1 | 162 |
| 5901 | 18955, 18954 | TIAM1 | 157, 70, 31 |
| 5913 | 18978, 18977 | ITGA11 | 133 |
| 5923 | 18998, 18997 | PTCH | 30, 27, 166, 83, 31 |
| 5942 | 19036, 19035 | DCC | 51 |
| 5943 | 19038, 19037 | SFTPB | 110 |
| 5967 | 19091, 19090 | GFRA1 | 116 |
| 6006 | 19170, 19169 | CDH13 | 31, 176, 133, 110, 51, 167 |
| 6025 | 19207, 19206 | AUTS2 | 24 |
| 6044 | 19245, 19244 | BCL11B | 109 |
| 6057 | 19271, 19270 | PTPRG | 157, 110, 31 |
| 6070 | 19297, 19296 | CXADR | 154, 30 |
| 6082 | 19321, 19320 | GABRA3 | 82, 29, 47, 123 |
| 6118 | 19393, 19392 | DMD | 129 |
| 6127 | 19411, 19410 | PRKCG | 31, 8, 154, 51 |
| 6151 | 19459, 19458 | STS | 31 |
| 6152 | 19461, 19460 | HTR2C | 162, 29, 120 |
| 6159 | 19475, 19474 | PARK2 | 144, 61 |
| 6164 | 19485, 19484 | ED1 | 166, 118 |
| 6213 | 19583, 19582 | NCOR2 | 109, 31 |
| 6220 | 19597, 19596 | CRHR1 | 57 |
| 6233 | 19624, 19623 | GRM3 | 162, 29 |
| 6255 | 19668, 19667 | LIPC | 97, 64, 53, 132, 105 |
| 6272 | 19702, 19701 | TIE | 109, 31, 4, 166, 157, 118 |
| 6285 | 19728, 19727 | PAX5 | 112 |
| 6289 | 19736, 19735 | MME | 167, 133, 110, 8 |
| 6327 | 19812, 19811 | IGSF4 | 133, 110, 90, 154, 31 |
| 6329 | 19816, 19815 | GRM7 | 162 |

TABLE 6-continued

RELATION OF MICRORNAS TO DISEASES BY HOST GENES

| HID | MID | H. Gene | Disease(s) |
|---|---|---|---|
| 6338 | 19834, 19833 | RAD51L1 | 110 |
| 6342 | 19842, 19841 | GOLGA5 | 173 |
| 6344 | 19846, 19845 | BAI1 | 133, 110, 51 |
| 6385 | 19929, 19928 | CTNNA1 | 152, 51 |
| 6398 | 19956, 19955 | AUTS2 | 24 |
| 6408 | 19976, 19975 | LGI1 | 82 |
| 6418 | 19996, 19995 | KCNQ3 | 82 |
| 6420 | 20000, 19999 | MYO7A | 60 |
| 6421 | 20002, 20001 | NTRK3 | 116, 8, 109, 157 |
| 6447 | 20060, 20059 | CHD4 | 63 |
| 6503 | 20172, 20171 | ACVR1B | 150, 140 |
| 6505 | 20176, 20175 | CDK6 | 133, 51, 31, 167 |
| 6521 | 20208, 20207 | SGCD | 100, 129 |
| 6542 | 20252, 20251 | HMGA2 | 79, 110 |
| 6571 | 20311, 20310 | HK2 | 134, 132, 64 |
| 6575 | 20319, 20318 | DBP | 87 |
| 6577 | 20323, 20322 | MTAP | 110, 109, 133 |
| 6580 | 20329, 20328 | TGFBI | 83 |
| 6582 | 20333, 20332 | KCNQ3 | 82 |
| 6588 | 20345, 20344 | SLC7A5 | 51 |
| 6600 | 20369, 20368 | PTPRF | 134, 31 |
| 6602 | 20373, 20372 | FLJ22795 | 51, 110 |
| 6611 | 20391, 20390 | TGM1 | 133, 8 |
| 6612 | 20393, 20392 | CHRNB1 | 124 |
| 6614 | 20397, 20396 | PAX2 | 157 |
| 6670 | 20516, 20515 | GPC3 | 31, 90 |
| 6671 | 20518, 20517 | SCN5A | 185, 34 |
| 6676 | 20528, 20527 | CACNA1G | 109, 51 |
| 6696 | 20571, 20570 | PRKCA | 51, 31, 150, 110, 64, 8, 132 |
| 6742 | 20665, 20664 | GRIK4 | 162, 82 |
| 6756 | 20693, 20692 | HTR2C | 162, 29, 120 |
| 6760 | 20701, 20700 | NEB | 129 |
| 6776 | 20736, 20735 | TGFBR3 | 31 |
| 6779 | 20742, 20741 | HTR2C | 162, 29, 120 |
| 6789 | 20762, 20761 | GRIA3 | 82, 77, 29 |
| 6811 | 20806, 20805 | CPB1 | 141 |
| 6819 | 20822, 20821 | HD | 8, 51 |
| 6821 | 20826, 20825 | BCL11B | 109 |
| 6835 | 20854, 20853 | NLGN3 | 24 |
| 6844 | 20872, 20871 | MEST | 110, 51, 31 |
| 6846 | 20876, 20875 | CA12 | 31, 157 |
| 6847 | 20878, 20877 | GABRA3 | 82, 29, 47, 123 |
| 6867 | 20918, 20917 | BIK | 31 |
| 6887 | 20961, 20960 | CDH13 | 31, 176, 133, 110, 51, 167 |
| 6918 | 21023, 21022 | PAX3 | 118, 60 |
| 6960 | 21107, 21106 | PRKDC | 51, 109 |

TABLE 7

TISSUE AND DISEASE CODES FOR TABLE 2 AND 3

| Tissue or Disease name | ID |
|---|---|
| Prostate adenocarcinoma | 1 |
| Lung adenocarcinoma | 2 |
| Skeletal muscle | 3 |
| Spleen | 4 |
| Lung | 5 |
| Lung adenocarcinoma | 6 |
| Placenta | 7 |
| Embryonic Stem cells | 8 |
| Prostate adenocarcinoma | 9 |
| Prostate | 10 |
| Brain Substantia Nigra | 11 |
| Testis | 12 |
| Uterus carcinoma cell line (HeLa) | 13 |
| Adipose | 14 |
| Lung carcinoma cell line (H1299) | 15 |
| Lung carcinoma cell line (H1299) with P53 | 16 |
| Overy and Small Intestine (mixture) | 17 |
| Embryonic Stem carcinoma cells | 18 |
| Brain | 19 |
| Brain with Alzheimer | 20 |
| Uterus carcinoma cell line (cMagi) with HIV | 21 |
| T cell line (MT2) | 22 |
| T cell line (MT2) with HIV | 23 |
| Placenta and Brain Substantia Nigra (mixture) | 24 |
| B cell line | 25 |
| T cell line (MT2) with HIV and Brain Substantia Nigra (mixture) | 26 |
| T cell line (MT2) with HIV and Lung adenocarcinoma (mixture) | 27 |

TABLE 8

DISEASE CODES FOR TABLES 5 AND 6

| Disease Name | ID |
|---|---|
| Addisons disease | 1 |
| Adenovirus | 2 |

TABLE 8-continued

DISEASE CODES FOR TABLES 5 AND 6

| Disease Name | ID |
|---|---|
| Adrenal cortical carcinoma | 3 |
| Aids | 4 |
| Allergic contact dermatitis | 5 |
| Alopecia | 6 |
| Alpha thalassemia | 7 |
| Alzheimer | 8 |
| Amyloidosis | 9 |
| Amyotrophic Lateral Sclerosis | 10 |
| Anal cancer | 11 |
| Anorexia Nervosa | 12 |
| Antisocial Personality Disorder | 13 |
| Aortic Aneurysm | 14 |
| Aortic stenosis | 15 |
| Aplastic anemia | 16 |
| Appendiciti | 17 |
| Asthma | 18 |
| Atherosclerosis | 19 |
| Atopic dermatiti | 20 |
| Atrial fibrillation | 21 |
| Atrophic gastriris | 22 |
| Attention Deficit Disorder | 23 |
| Autism | 24 |
| Bacillary Dysentery | 25 |
| Barrett Esophagus | 26 |
| Basal cell carcinoma | 27 |
| Beta Thalassemia | 28 |
| Bipolar Disorder | 29 |
| Bladder cancer | 30 |
| Breast cancer | 31 |
| Bronchiectasis | 32 |
| Bulimia | 33 |
| Bundle-Branch Block | 34 |
| Burkitt lymphoma | 35 |
| Carcinoid | 36 |
| Cataract | 37 |
| Celiac Disease | 38 |
| Cerebral Hemorrhage | 39 |
| Cerebral Infarction | 40 |
| Cerebrovascular Accident | 41 |
| Cervical cancer | 42 |
| Chlamydia | 43 |
| Cholelithiasis | 44 |
| Cholestasis | 45 |
| Chronic obstructive pulmonary disease | 46 |
| Cirrhosis | 47 |
| Cleft Lip | 48 |
| Cleft Palate | 49 |
| Clostridium | 50 |
| Colorectal cancer | 51 |
| Coronary artery disease | 52 |
| Coronary disease | 53 |
| Coronary spasm | 54 |
| Coxsackievirus | 55 |
| Crohn disease | 56 |
| Cushing Syndrome | 57 |
| Cystic fibrosis | 58 |
| Cytomegalovirus | 59 |
| Deafness | 60 |
| Dementia | 61 |
| Depressive Disorder | 62 |
| Dermatomyositis | 63 |
| Diabetes Mellitus | 64 |
| Diabetic Nephropathy | 65 |
| Diabetic Neuropathies | 66 |
| Diabetic Retinopathy | 67 |
| Diphtheria | 68 |
| Diverticulitis | 69 |
| Down Syndrome | 70 |
| Duodenal Neoplasms | 71 |
| Duodenal Ulcer | 72 |
| Dyslexia | 73 |
| E.coli | 74 |
| EBV | 75 |
| Emphysema | 76 |
| Encephalitis | 77 |
| Endocarditis | 78 |
| Endometrial carcinoma | 79 |
| Enterovirus | 80 |
| Enuresis | 81 |
| Epilepsy | 82 |
| Esophageal cancer | 83 |
| Fragile X Syndrome | 84 |
| Gestational Diabetes | 85 |
| Hemolytic anemia | 86 |
| Hemophilia | 87 |
| Hepatitis | 88 |
| Hepatocellular carcinoma | 89 |
| Hepatocellular carcinoma | 90 |
| Herpes | 91 |
| HIV | 92 |
| Hodgkin Disease | 93 |
| HTLV | 94 |
| Hypercholesterolemia | 95 |
| Hyperglycemia | 96 |
| Hyperlipidemia | 97 |
| Hypertension | 98 |
| Hypertrophic Cardiomopathy | 99 |
| Hypertrophic cardiomyopathy | 100 |
| Infectious Mononucleosis | 101 |
| Infertility | 102 |
| Inflammatory Bowel Diseases | 103 |
| Influenza | 104 |
| Insulin-Dependent Diabetes Mellitus | 105 |
| Intestinal Neoplasms | 106 |
| Kidney Failure | 107 |
| Left Ventricular Dysfunction | 108 |
| Leukemia | 109 |
| Lung cancer | 110 |
| Lupus Erythematosus | 111 |
| Lymphoma | 112 |
| Macular Degeneration | 113 |
| Malaria | 114 |
| Measles | 115 |
| Medullary thyroid carcinoma | 116 |
| Megaloblastic anemia | 117 |
| Melanoma | 118 |
| Meningitis | 119 |
| Migraine | 120 |
| Multiinfarct dementia | 121 |
| Multiple Myeloma | 122 |
| Multiple Sclerosis | 123 |
| Myasthenia Gravis | 124 |
| Mycobacterium | 125 |
| Mycoplasma | 126 |
| Myocardial Infarction | 127 |
| Myocarditis | 128 |
| Myopathy | 129 |
| Nephrogenic diabetes insipidus | 130 |
| Nephrolithiasis | 131 |
| Non-Insulin-Dependent Diabetes Mellitus | 132 |
| Nonsmall cell lung cancer | 133 |
| Obesity | 134 |
| Osteoarthritis | 135 |
| Osteoporosis | 136 |
| Otitis Media | 137 |
| Ovarian cancer | 138 |
| Pagets Disease | 139 |
| Pancreatic cancer | 140 |
| Pancreatitis | 141 |
| Papilloma | 142 |
| Paramyxoviridae | 143 |
| Parkinson | 144 |
| Peptic Ulcer | 145 |
| Peripheral Vascular Diseases | 146 |
| Peritonitis | 147 |
| Pertussis | 148 |
| Picornaviridae | 149 |
| Pituitary tumor | 150 |
| Polyposis | 151 |
| Polyposis coli | 152 |
| Postpartum depression | 153 |
| Prostate cancer | 154 |

TABLE 8-continued

DISEASE CODES FOR TABLES 5 AND 6

| Disease Name | ID |
|---|---|
| Psoriasis | 155 |
| Psoriatic arthritis | 156 |
| Renal cell carcinoma | 157 |
| Renal Tubular Acidosis | 158 |
| Respiratory Syncytial Virus | 159 |
| Rheumatoid arthritis | 160 |
| Rhinitis | 161 |
| Schizophrenia | 162 |
| Sickle cell anemia | 163 |
| Sideroblastic anemia | 164 |
| Sinusitis | 165 |
| Skin Neoplasms | 166 |
| Small cell carcinoma | 167 |
| Stroke | 168 |
| Sudden cardiac death | 169 |
| Syphilis | 170 |
| Thrombocytopenia | 171 |
| Thrombosis | 172 |
| Thyroid carcinoma | 173 |
| Thyroiditis | 174 |
| Toxoplasmosis | 175 |
| Transitional cell carcinoma | 176 |
| Trichomonas vaginitis | 177 |
| Tuberculosis | 178 |
| Turner Syndrome | 179 |
| Ulcerative colitis | 180 |
| Urethral neoplasms | 181 |
| Urinary calculi | 182 |
| Urticaria | 183 |
| Vascular dementia | 184 |
| Ventricular Fibrillation | 185 |
| Ventricular tachycardia | 186 |
| Virus Diseases | 187 |

TABLE 9

RELATION OF TARGET GENES TO DISEASE

| Gene Name | Disease Code |
|---|---|
| A2M | 8, 76, 144 |
| AAAS | 1 |
| AANAT | 27, 118 |
| AARS | 63 |
| AAT1 | 14 |
| AAT2 | 14 |
| ABAT | 162 |
| ABCA1 | 53 |
| ABCA4 | 113 |
| ABCB1 | 31, 51, 92, 167, 110, 133, 152 |
| ABCB11 | 45 |
| ABCB4 | 31, 44, 45 |
| ABCB7 | 164 |
| ABCC1 | 31, 110 |
| ABCC2 | 51, 90 |
| ABCC3 | 30, 110, 133, 167 |
| ABCC4 | 110 |
| ABCC5 | 92, 110 |
| ABCC6 | 109 |
| ABCC8 | 64, 132 |
| ABCD1 | 1 |
| ABCD3 | 51 |
| ABCG2 | 31, 109, 110 |
| ABL1 | 31, 51, 109 |
| ABL2 | 109 |
| ABO | 30, 109 |
| ABP1 | 42, 79, 154 |
| ACE | 8, 31, 65, 110, 127, 133 |
| ACHE | 8, 10 |
| ACO1 | 8 |
| ACP1 | 64, 105, 134 |
| ACP5 | 31, 107, 160 |
| ACPP | 30, 154, 181 |

TABLE 9-continued

RELATION OF TARGET GENES TO DISEASE

| Gene Name | Disease Code |
|---|---|
| ACR | 102 |
| ACTA1 | 129 |
| ACTB | 8, 31, 51, 167 |
| ACTC | 100, 129, 162 |
| ACTG1 | 60 |
| ACTN4 | 31 |
| ACVR1 | 31, 150 |
| ACVR1B | 140, 150 |
| ACVR2 | 150 |
| ACY1 | 110, 157, 167 |
| AD2 | 8 |
| AD5 | 8 |
| AD6 | 8 |
| AD7C-NTP | 8 |
| AD8 | 8 |
| ADA | 86 |
| ADAM10 | 21, 135 |
| ADAM11 | 31 |
| ADAM12 | 47, 90, 109, 112, 122, 134 |
| ADAM17 | 160 |
| ADAM2 | 8 |
| ADAMTS13 | 4, 171 |
| ADAMTS4 | 160 |
| ADCY1 | 8 |
| ADCY2 | 8 |
| ADCY8 | 8 |
| ADCYAP1 | 110, 140, 150, 154, 167 |
| ADD1 | 98 |
| ADFN | 60 |
| ADH1B | 83 |
| ADH1C | 31, 127 |
| ADM | 3, 52, 64, 132, 154, 79, 85, 108 |
| ADORA1 | 8, 58, 186 |
| ADORA3 | 118 |
| ADPRT | 31, 51, 110 |
| ADRA2A | 8, 23, 62, 134, 162 |
| ADRA2C | 23 |
| ADRB1 | 8, 52, 53, 98, 134 |
| ADRB2 | 8, 18, 58, 132, 134, 64, 97, 98 |
| ADRB3 | 53, 64, 67, 134, 97, 98, 132 |
| ADRBK1 | 53, 58, 98, 160 |
| ADSL | 24 |
| AF15Q14 | 109 |
| AF3P21 | 109 |
| AF5Q31 | 109 |
| AFM | 90 |
| AFP | 31, 154 |
| AGER | 8, 9, 64, 146, 105, 132, 133 |
| AGR2 | 31 |
| AGRN | 8 |
| AGRP | 12, 134 |
| AGT | 8, 64, 65, 98, 105, 132 |
| AGTR1 | 3, 15, 53, 127, 98, 99, 105, 64, 65, 95 |
| AGTR2 | 57, 95, 108 |
| AHR | 31, 79, 110, 154 |
| AIF1 | 40 |
| AIRE | 1, 64, 105, 174 |
| AK1 | 86 |
| AKAP12 | 110, 124 |
| AKR1B1 | 64, 66, 90, 105 |
| AKR1B10 | 90 |
| AKT1 | 10, 31, 64, 133, 154, 162, 79, 110, 132 |
| AKT2 | 31, 83, 110 |
| AKT3 | 31, 51, 110, 154 |
| ALAS2 | 164 |
| ALB | 4, 8, 31, 133, 167, 105, 110, 132, 51, 64, 92 |
| ALCAM | 118 |
| ALDH1A1 | 133, 157 |
| ALDH3A1 | 31, 83, 90 |
| ALDOA | 110 |
| ALK | 93, 112 |
| ALMS1 | 134 |
| ALOX12 | 64, 98, 132, 154 |
| ALOX15 | 51, 154 |
| ALOX15B | 154 |
| ALOX5 | 18, 31, 92, 140, 154, 180, 109, 110, 112 |

TABLE 9-continued

RELATION OF TARGET GENES TO DISEASE

| Gene Name | Disease Code |
|---|---|
| ALOX5AP | 18, 92, 127, 168 |
| ALPL | 31 |
| ALPP | 70, 79 |
| ALS2 | 10 |
| ALS4 | 10 |
| ALS6 | 10 |
| ALSFTD | 10, 61 |
| AMACR | 51, 154 |
| AMBP | 92, 110 |
| AMFR | 30, 118, 133, 154 |
| AMN | 117 |
| AMPH | 31 |
| AMT | 96 |
| AMY2A | 64, 105 |
| ANG | 31, 42, 51, 109, 118, 154 |
| ANGPT1 | 31, 42, 133 |
| ANGPT2 | 31, 51, 90 |
| ANGPT4 | 31, 157 |
| ANON | 12 |
| ANP32A | 92 |
| ANPEP | 51, 123 |
| ANXA1 | 31, 83, 110, 154 |
| ANXA2 | 110, 154, 167 |
| ANXA3 | 43 |
| AOC3 | 8, 61, 103, 107, 121 |
| AOCH | 49 |
| AOMS1 | 134 |
| AOMS2 | 134 |
| APBA1 | 51 |
| APBA2 | 8, 51, 75 |
| APBB1 | 8, 144 |
| APC | 31, 51, 83, 167, 151, 152, 154, 106, 110, 133 |
| APCS | 8, 9, 64, 132 |
| APEH | 157 |
| APEX1 | 10, 42, 51, 109 |
| APLP1 | 8 |
| APLP2 | 8 |
| APM1 | 12, 64, 92, 98, 132, 134 |
| APOA2 | 64, 95, 98, 127, 132 |
| APOA4 | 8, 9, 53, 134, 141, 105, 127, 132, 64, 95, 97 |
| APOB | 4, 8, 31, 105, 132, 64, 92, 95 |
| APOBEC1 | 51 |
| APOBEC3G | 92 |
| APOC1 | 8, 64, 95, 97, 132 |
| APOC2 | 8, 64, 132 |
| APOC3 | 8, 53, 64, 134, 97, 105, 132 |
| APOD | 8, 29, 31, 132, 162, 64, 123, 127 |
| APOH | 64, 111 |
| APOL1 | 162 |
| APOL2 | 162 |
| APOL4 | 162 |
| APP | 8, 9, 31, 123, 162 |
| APPBP2 | 31 |
| APRIN | 154 |
| APRT | 131, 182 |
| APXL | 118 |
| AQP1 | 157 |
| AQP2 | 81, 130 |
| AR | 8, 31, 51, 92, 110, 154 |
| AREG | 30, 31, 42, 155, 133, 51, 154 |
| ARG2 | 64 |
| ARH | 95 |
| ARHA | 31, 51, 89, 154, 159, 90, 110, 118 |
| ARHB | 31 |
| ARHC | 31 |
| ARHI | 31, 138 |
| ARHU | 31, 51, 157 |
| ARMD1 | 113 |
| ARMET | 140 |
| ARNT | 31, 109 |
| ARVCF | 29 |
| ARX | 82 |
| AS1 | 18 |
| ASAH1 | 20, 106, 154 |
| ASC | 17, 31 |
| ASCL1 | 167 |
| ASGR1 | 47, 88, 90 |
| ASPSCR1 | 157 |
| ATF1 | 118 |
| ATF2 | 31, 110, 118 |
| ATF3 | 51 |
| ATF6 | 8 |
| ATIC | 112 |
| ATM | 31, 93, 112 |
| ATP10A | 24 |
| ATP1A1 | 8, 64, 98, 105 |
| ATP1A2 | 120 |
| ATP1A4 | 120 |
| ATP2A1 | 129 |
| ATP2A2 | 29 |
| ATP6B1 | 60, 158 |
| ATP6V0A4 | 158 |
| ATP6V1B1 | 158 |
| ATP6V1G2 | 160 |
| ATP7B | 31 |
| ATP8B1 | 45 |
| ATPIF1 | 129 |
| ATRX | 31, 51, 112 |
| AURKB | 51 |
| AUTS1 | 24 |
| AUTS2 | 24 |
| AUTS3 | 24 |
| AUTS4 | 24 |
| AVP | 110, 167 |
| AVPR1A | 24, 57, 98 |
| AVPR1B | 36, 57, 110, 150 |
| AVPR2 | 130 |
| AXIN1 | 90 |
| AXIN2 | 51 |
| AXL | 51, 90, 109, 110, 167 |
| AZGP1 | 31, 154 |
| AZU1 | 8 |
| B2M | 4, 8, 9, 123, 133, 92, 110, 118, 31, 51, 77 |
| B3GALT1 | 51 |
| B3GALT2 | 154 |
| BAALC | 109 |
| BACE | 8 |
| BACE2 | 8, 31, 51, 70 |
| BAD | 8, 109, 110, 118 |
| BAG1 | 31, 42, 109 |
| BAI1 | 51, 110, 133 |
| BAK1 | 8, 31, 51, 166, 110, 133, 154 |
| BAL | 112 |
| BARD1 | 31 |
| BAX | 8, 31, 51, 123, 167, 110, 133 |
| BBP | 8 |
| BCAR1 | 2, 31, 118 |
| BCAR3 | 31 |
| BCAS1 | 31, 51 |
| BCAS2 | 31 |
| BCHE | 8, 110 |
| BCL1 | 112 |
| BCL10 | 31, 42, 51, 157, 112, 122, 154, 79, 109, 110 |
| BCL11A | 93, 109, 112 |
| BCL11B | 109 |
| BCL2 | 4, 8, 31, 167, 112, 123, 133, 51, 92, 110 |
| BCL2L1 | 8, 31, 51, 167, 123, 133, 154, 92, 110, 122 |
| BCL3 | 48, 49, 83, 109, 112 |
| BCL6 | 4, 31, 112 |
| BCL7A | 93, 112 |
| BCL8 | 112 |
| BCL9 | 109, 112 |
| BCMP11 | 31 |
| BCPR | 31 |
| BDKRB1 | 160 |
| BDKRB2 | 18, 64, 92, 132, 154, 160 |
| BDNF | 8, 123 |
| BF | 174 |
| BFSP2 | 37 |
| BGLAP | 31, 64, 92, 136, 105, 110, 132 |
| BID | 90, 154 |
| BIK | 31 |

TABLE 9-continued

RELATION OF TARGET GENES TO DISEASE

| Gene Name | Disease Code |
| --- | --- |
| BIN1 | 31, 118, 154 |
| BIRC2 | 42, 83, 123 |
| BIRC3 | 110, 112, 122, 123 |
| BIRC4 | 51, 109, 122, 133 |
| BIRC5 | 31, 51, 110, 133, 140 |
| BIRC7 | 118 |
| BLCAP | 30, 157 |
| BLM | 51, 106, 109 |
| BLMH | 8, 35, 112 |
| BLR1 | 4, 92, 109, 112, 122, 123 |
| BLZF1 | 109 |
| BMP1 | 154 |
| BMP2 | 154 |
| BMP3 | 154 |
| BMP6 | 154 |
| BMPR1A | 151 |
| BMPR2 | 98, 154 |
| BMX | 154 |
| BPGM | 86 |
| BRAF | 51, 110, 118 |
| BRCA1 | 31, 51, 138 |
| BRCA2 | 31, 51, 110, 133, 140, 154 |
| BRCA3 | 31 |
| BRCATA | 31 |
| BRCD1 | 31 |
| BRIP1 | 31 |
| BRS3 | 110, 134 |
| BSG | 92, 118, 166 |
| BSND | 60 |
| BST2 | 122 |
| BTC | 79 |
| BUB1 | 51, 109, 110, 112, 133 |
| BUB1B | 51, 109, 112 |
| BULN | 33 |
| BZRP | 8, 31, 162 |
| C11orf17 | 31, 154 |
| C13orf1 | 109 |
| C1QA | 111 |
| C1QB | 8, 10 |
| C1R | 8, 77, 123 |
| C1S | 8, 111 |
| C21orf107 | 70 |
| C21orf33 | 60 |
| C3 | 8, 31, 51, 110, 134, 64, 92, 105 |
| C3AR1 | 18, 119, 123 |
| C4A | 64, 105, 111, 127 |
| C4BPA | 148 |
| C4BPB | 148 |
| C5 | 8, 92, 119, 127 |
| C5orf7 | 109 |
| C5R1 | 18, 92, 119, 123 |
| C6orf15 | 155 |
| C6orf18 | 155 |
| C7 | 8 |
| C9 | 8, 63, 119, 123, 127 |
| CA1 | 109, 133, 141 |
| CA12 | 31, 157 |
| CA2 | 158 |
| CA9 | 31, 42, 51, 118, 133, 157 |
| CAAR | 37 |
| CAB2 | 31 |
| CACNA1A | 61, 120 |
| CACNA1G | 51, 109 |
| CACNA2D2 | 133 |
| CACNB2 | 82, 167 |
| CACNB4 | 82 |
| CALB1 | 8, 10, 51, 82, 144 |
| CALB2 | 8, 51, 162 |
| CALCA | 110, 136, 167 |
| CALCB | 116, 160 |
| CALCR | 31, 136, 160 |
| CALCRL | 98 |
| CALR | 35, 38, 51, 160, 111, 112, 154 |
| CANX | 31, 58 |
| CAPN10 | 64, 132 |
| CARD15 | 56, 103, 156, 180 |
| CARD4 | 103 |
| CART | 134 |
| CASP1 | 4, 31, 51, 92, 123 |
| CASP10 | 93, 112, 133 |
| CASP2 | 8, 109 |
| CASP3 | 8, 31, 42, 154, 110, 123, 133, 51, 92, 109 |
| CASP5 | 51, 79, 133 |
| CASP6 | 31, 118, 154 |
| CASP7 | 31, 51, 154, 157 |
| CASP8 | 8, 31, 51, 157, 167, 92, 110, 133 |
| CASP9 | 4, 8, 31, 122, 133, 51, 90, 110 |
| CASQ2 | 186 |
| CASR | 31, 64, 132, 136 |
| CAST | 8, 63, 98, 109, 111, 160 |
| CAT | 4, 8, 31, 110, 132, 133, 51, 64, 92 |
| CATM | 37 |
| CAV1 | 31, 47, 51, 154, 155, 83, 92, 110 |
| CAV2 | 83, 154 |
| CBFA2T1 | 109 |
| CBFA2T3 | 31, 109 |
| CBL | 109, 112 |
| CBS | 19, 70 |
| CCA1 | 37 |
| CCAL1 | 135 |
| CCFDN | 37 |
| CCK | 8, 64, 132, 167 |
| CCKAR | 44, 64, 132, 134, 141, 162 |
| CCKBR | 51, 64, 110, 132, 162, 167 |
| CCL1 | 5, 92, 125, 159 |
| CCL11 | 18, 20, 56, 165, 180, 183, 92, 93, 159 |
| CCL13 | 18, 155 |
| CCL17 | 5, 18, 20, 93, 109 |
| CCL2 | 8, 31, 64, 167, 123, 132, 133, 92, 105, 110 |
| CCL20 | 155, 160 |
| CCL21 | 20 |
| CCL24 | 18 |
| CCL3 | 4, 31, 51, 92, 94, 123 |
| CCL4 | 4, 8, 31, 123, 133, 92, 94, 110 |
| CCL5 | 31, 42, 92, 94, 123, 133 |
| CCL7 | 18, 20, 92, 123, 180 |
| CCL8 | 92, 112 |
| CCNA1 | 109 |
| CCNB1 | 8, 31, 51, 110, 133 |
| CCNC | 31, 109 |
| CCND1 | 31, 51, 110, 180, 133, 112, 122, 167 |
| CCND2 | 31, 51 |
| CCND3 | 31, 35, 109, 112, 118, 122 |
| CCNE1 | 31, 110, 133, 167 |
| CCNE2 | 31, 42, 109, 133, 167 |
| CCNI | 31 |
| CCNP | 37 |
| CCNT1 | 92 |
| CCR1 | 88, 91, 92, 123, 160 |
| CCR2 | 4, 18, 61, 135, 136, 160, 92, 122, 123 |
| CCR3 | 18, 20, 92, 93, 123 |
| CCR4 | 18, 20, 88, 112, 123, 92, 93, 111 |
| CCR5 | 4, 61, 92, 123 |
| CCR6 | 94, 109, 112, 122, 160 |
| CCR7 | 31, 59, 92, 118, 93, 109, 112 |
| CCR8 | 18, 46, 92, 123 |
| CCS | 10 |
| CCSSO | 37 |
| CCT | 37 |
| CCV | 37 |
| CD14 | 4, 31, 51, 92, 123 |
| CD151 | 110, 133 |
| CD163 | 109, 123, 160 |
| CD19 | 31, 51, 92, 110 |
| CD1A | 31, 92 |
| CD1B | 20, 123 |
| CD1C | 111 |
| CD1D | 64, 105, 109 |
| CD22 | 92 |
| CD24 | 31, 35, 90, 133, 154, 167, 109, 110, 112 |
| CD33 | 31 |
| CD34 | 31, 92 |

TABLE 9-continued

RELATION OF TARGET GENES TO DISEASE

| Gene Name | Disease Code |
|---|---|
| CD36 | 31, 64, 92, 167, 114, 171, 110, 132 |
| CD37 | 109, 112 |
| CD38 | 4, 64, 92, 105, 132 |
| CD3G | 92 |
| CD3Z | 93, 111, 157 |
| CD4 | 4, 31, 92, 111 |
| CD44 | 31, 51, 92, 133, 157, 109, 110, 123 |
| CD47 | 109 |
| CD58 | 31, 51, 64, 92, 105 |
| CD59 | 4, 8, 31, 114, 51, 92, 110 |
| CD63 | 92, 118 |
| CD68 | 4, 92 |
| CD69 | 18, 31, 64, 160, 178, 92, 105, 111 |
| CD74 | 110, 133, 167 |
| CD80 | 31, 51, 64, 123, 105, 92, 110 |
| CD83 | 31, 92, 109, 157 |
| CD86 | 31, 51, 64, 92, 105, 123 |
| CD8A | 38, 88, 92, 93, 109, 157 |
| CD8B1 | 92 |
| CD9 | 31, 51, 133, 167 |
| CD97 | 112, 160 |
| CDA | 109 |
| CDC10 | 112 |
| CDC2 | 8, 31, 51, 167, 92, 110, 133 |
| CDC25A | 31, 51, 83, 112, 133 |
| CDC25B | 31, 51, 83, 112, 133 |
| CDC25C | 79, 112, 166 |
| CDC27 | 118 |
| CDC2L1 | 112, 118 |
| CDC2L2 | 118 |
| CDC42 | 31, 51 |
| CDH1 | 31 |
| CDH11 | 31, 51, 154 |
| CDH13 | 31, 51, 110, 133, 167, 176 |
| CDH17 | 109 |
| CDH23 | 60 |
| CDH5 | 118 |
| CDH6 | 157, 167 |
| CDK10 | 31, 112 |
| CDK2 | 31, 42, 51, 110, 133 |
| CDK4 | 8, 31, 51, 110, 118, 133 |
| CDK5 | 8, 10 |
| CDK5R1 | 8, 70 |
| CDK6 | 31, 51, 133, 167 |
| CDK7 | 31, 51 |
| CDK9 | 92 |
| CDKN1A | 31, 51, 79, 133, 167, 180, 90, 92, 110 |
| CDKN1B | 31, 110, 133, 167 |
| CDKN1C | 3, 30, 31, 110, 141, 51, 90, 109 |
| CDKN2A | 8, 31, 51, 133, 140, 167, 109, 110, 118 |
| CDKN2A_ARF | 31, 51, 110, 133, 180 |
| CDKN2B | 31, 110, 133, 167 |
| CDKN2C | 8, 31, 94, 122, 133, 109, 112, 118 |
| CDKN2D | 31, 109, 110, 167 |
| CDPD1 | 60 |
| CDR2 | 31 |
| CDSN | 155 |
| CDW52 | 109, 123, 160, 174 |
| CDX1 | 51, 106 |
| CDX2 | 51, 106, 151 |
| CDY1 | 102 |
| CEACAM1 | 31, 51, 79, 154, 90, 110, 118 |
| CEACAM5 | 31, 51, 110, 133 |
| CEACAM6 | 31, 51, 109, 133 |
| CEACAM8 | 135, 157, 160 |
| CEBPA | 31, 90, 109, 110 |
| CEBPB | 31, 51, 92 |
| CEBPE | 109 |
| CENPF | 31, 90 |
| CES2 | 51 |
| CETP | 53, 64, 105, 132 |
| CFLAR | 93, 109, 112, 118, 122, 123 |
| CFM1 | 58 |
| CFTR | 18, 32, 58, 102, 141 |
| CGA | 30, 31, 70, 110, 150 |
| CGB | 31, 110, 133 |
| CGB5 | 30, 110 |
| CGB7 | 110 |
| CGB8 | 30, 110 |
| CHAT | 8, 10, 124 |
| CHD3 | 63 |
| CHD4 | 63 |
| CHEK2 | 31, 51, 110, 154, 167 |
| CHGA | 110, 133, 167 |
| CHGB | 36, 110, 167 |
| CHI3L1 | 31, 160 |
| CHK | 31, 51, 166 |
| CHL1 | 162 |
| CHRM1 | 8, 144, 162 |
| CHRM2 | 8, 18, 62, 162, 169 |
| CHRM3 | 8, 18, 51, 154 |
| CHRM4 | 8, 18, 144 |
| CHRNA1 | 124 |
| CHRNA3 | 82 |
| CHRNA4 | 8, 24, 82, 144 |
| CHRNA5 | 82 |
| CHRNA7 | 8, 24, 144, 162 |
| CHRNB1 | 124 |
| CHRNB2 | 82, 162 |
| CHRNE | 124 |
| CHRNG | 124 |
| CHST2 | 51 |
| CHUK | 31, 118, 154 |
| CHX10 | 37 |
| CIP29 | 35, 90, 109, 112 |
| CIRH1A | 47 |
| CKB | 8, 109, 127 |
| CKMT1 | 93, 129 |
| CLCA1 | 51 |
| CLCN2 | 82 |
| CLCN5 | 131 |
| CLCNKB | 98 |
| CLDN1 | 31, 51 |
| CLDN11 | 123 |
| CLDN14 | 60 |
| CLOCK | 62 |
| CLTCL1 | 112 |
| CLU | 8, 10, 31, 127, 154 |
| CMD1B | 129 |
| CMD1C | 129 |
| CMD1E | 129 |
| CMD1F | 129 |
| CMD1H | 129 |
| CMD1J | 129 |
| CMD1K | 129 |
| CMH6 | 129, 144 |
| CMKBR2 | 92 |
| CMKBR5 | 92 |
| CMM | 118 |
| CNK | 110 |
| CNN1 | 90 |
| CNP | 8, 70, 123 |
| CNR1 | 31, 144, 154, 162 |
| CNTF | 8, 10, 122, 162 |
| COCH | 60 |
| COL11A2 | 60 |
| COL17A1 | 27, 91, 154 |
| COL18A1 | 31, 35, 90, 112, 157, 109, 133 |
| COL1A1 | 136 |
| COL1A2 | 136 |
| COL2A1 | 60, 135 |
| COL3A1 | 14 |
| COL4A1 | 154 |
| COL4A2 | 154, 157 |
| COL4A3 | 118 |
| COL4A4 | 67 |
| COL4A6 | 83, 154, 157 |
| COL6A1 | 70, 129 |
| COL6A2 | 129 |
| COL6A3 | 129 |
| COL9A3 | 129 |
| COMP | 160 |

TABLE 9-continued

RELATION OF TARGET GENES TO DISEASE

| Gene Name | Disease Code |
|---|---|
| COMT | 23, 29, 31, 62, 144, 162 |
| COPEB | 154 |
| COPS5 | 31, 150 |
| CORTBP2 | 24 |
| COX15 | 129 |
| COX4I1 | 8 |
| CP | 8, 64, 105, 110, 132, 144 |
| CPA5 | 24 |
| CPB1 | 141 |
| CPB2 | 127, 172 |
| CPE | 64, 105 |
| CPI | 49 |
| CPLX1 | 29, 162 |
| CPLX2 | 29, 162 |
| CPT2 | 129 |
| CPX | 49 |
| CR1 | 4, 47, 92, 123, 160, 110, 111, 122 |
| CR2 | 18, 75, 92, 109, 111 |
| CRABP1 | 42, 79, 109 |
| CRABP2 | 166 |
| CRAT | 8 |
| CREB1 | 8, 110 |
| CREBBP | 109 |
| CREM | 3, 94, 102, 111, 154 |
| CRH | 8, 110, 123 |
| CRHBP | 8, 57, 160 |
| CRHR1 | 57 |
| CRISP3 | 154 |
| CRKL | 109 |
| CRMP1 | 110 |
| CRYAA | 37 |
| CRYAB | 8, 37, 75, 123, 129 |
| CRYBA1 | 37 |
| CRYBB1 | 37 |
| CRYBB2 | 37 |
| CRYGC | 37 |
| CRYGD | 37 |
| CRYGS | 37 |
| CRYM | 60 |
| CS | 8, 47, 64, 132 |
| CSE1L | 31, 51, 109 |
| CSEN | 8 |
| CSF2 | 4, 31, 51, 166, 167, 92, 110, 133 |
| CSF3 | 4, 31, 64, 133, 167, 92, 110, 132 |
| CSH1 | 31, 70, 85 |
| CSH2 | 31 |
| CSK | 154 |
| CSN2 | 64, 105 |
| CSPG2 | 31, 109, 118, 154 |
| CSRP3 | 129, 154 |
| CST | 90, 157 |
| CST3 | 8, 9, 10, 123, 51, 53, 110 |
| CST6 | 31 |
| CSTA | 31, 154 |
| CSTB | 51, 82 |
| CTAA1 | 37 |
| CTAA2 | 37 |
| CTAG1 | 51, 83, 110, 157, 112, 118, 122 |
| CTAG2 | 30, 118, 133, 154 |
| CTGF | 31, 47, 64, 109, 65, 103, 105 |
| CTLA4 | 1, 18, 38, 174, 123, 124, 160, 105, 111, 122, 64, 92, 93 |
| CTM | 37 |
| CTNNA1 | 51, 152 |
| CTNNB1 | 31, 51, 90, 110, 133 |
| CTNNBIP1 | 51, 118 |
| CTNND1 | 30, 51, 118, 133, 154 |
| CTNND2 | 154 |
| CTPP | 37 |
| CTPP3 | 37 |
| CTPS | 109 |
| CTSB | 8, 31, 51, 110, 123, 133 |
| CTSD | 8, 31, 51, 92 |
| CTSE | 8 |
| CTSG | 8, 41, 56, 127, 172, 180 |
| CTSH | 110, 154 |
| CTSK | 135 |
| CTSL | 22, 31, 51, 76, 83, 118 |
| CTSL2 | 31, 51, 157 |
| CTSS | 8, 70, 110 |
| CTSW | 109 |
| CUBN | 117 |
| CUL2 | 157 |
| CUTL1 | 31, 109 |
| CX3CL1 | 56, 77, 92, 160 |
| CX3CR1 | 4, 92 |
| CXADR | 30, 154 |
| CXCL1 | 56, 74, 104, 166, 155, 160, 118, 135, 154 |
| CXCL10 | 31, 51, 77, 133, 92, 110, 123 |
| CXCL12 | 4, 31, 52, 154, 160, 106, 109, 112, 61, 90, 92 |
| CXCL13 | 160 |
| CXCL2 | 74, 118 |
| CXCL5 | 74, 110, 126, 133, 160 |
| CXCL9 | 5, 58, 88, 123 |
| CXCR3 | 109, 123 |
| CXCR4 | 31, 52, 91, 160, 170, 92, 154, 157 |
| CXCR6 | 92 |
| CXorf6 | 129 |
| CYLD | 157, 166 |
| CYP11A1 | 3 |
| CYP11B2 | 98 |
| CYP19A1 | 31, 79, 90, 154 |
| CYP1A1 | 27, 31, 51, 110, 154, 157, 79, 83, 88 |
| CYP1A2 | 51, 88, 141, 162 |
| CYP1B1 | 31, 51, 83, 110, 154, 166 |
| CYP21A2 | 1, 64, 105 |
| CYP27A1 | 154 |
| CYP27B1 | 42, 51, 154 |
| CYP2A6 | 51, 83, 110 |
| CYP2C19 | 30, 154 |
| CYP2C9 | 45, 88, 110 |
| CYP2D@ | 144 |
| CYP2D6 | 10, 11, 27, 162, 88, 110, 144, 30, 31, 62 |
| CYP3A4 | 90, 92, 109, 154 |
| CYP46A1 | 8 |
| CYP7A1 | 44 |
| CYP7B1 | 88 |
| CYR61 | 31, 133 |
| D12S2489E | 59 |
| D2S448 | 118, 166 |
| DAB1 | 162 |
| DAB2 | 31, 154 |
| DAB2IP | 154 |
| DAF | 4, 42, 51, 114, 123, 109, 110, 112 |
| DAO | 162 |
| DAPK1 | 30, 31, 51, 133, 176, 109, 110, 112 |
| DAZ | 102 |
| DAZL | 102 |
| DBCCR1 | 30, 176 |
| DBH | 23, 29, 162 |
| DBI | 8, 47, 162 |
| DBN1 | 8, 70 |
| DBP | 87 |
| DCC | 51 |
| DCK | 70, 109, 154 |
| DCN | 31, 51 |
| DCR | 70 |
| DCT | 118 |
| DCTD | 109 |
| DCX | 82 |
| DDB1 | 88, 113 |
| DDB2 | 88 |
| DDC | 23, 24, 29, 167, 133, 144, 162, 36, 64, 105 |
| DDIT3 | 31, 133 |
| DDR1 | 31 |
| DDX10 | 109 |
| DDX26 | 110, 133 |
| DDX6 | 51, 112 |
| DEK | 109, 111 |
| DES | 4, 110, 129, 167 |
| DEXI | 76 |
| DFFB | 31 |

TABLE 9-continued

RELATION OF TARGET GENES TO DISEASE

| Gene Name | Disease Code |
|---|---|
| DFN2 | 60 |
| DFN4 | 60 |
| DFN6 | 60 |
| DFNA16 | 60 |
| DFNA18 | 60 |
| DFNA2 | 60 |
| DFNA23 | 60 |
| DFNA24 | 60 |
| DFNA25 | 60 |
| DFNA30 | 60 |
| DFNA4 | 60 |
| DFNA44 | 60 |
| DFNA49 | 60 |
| DFNA5 | 60 |
| DFNA52 | 60 |
| DFNA7 | 60 |
| DFNB13 | 60 |
| DFNB14 | 60 |
| DFNB15 | 60 |
| DFNB17 | 60 |
| DFNB20 | 60 |
| DFNB26 | 60 |
| DFNB27 | 60 |
| DFNB31 | 60 |
| DFNB33 | 60 |
| DFNB38 | 60 |
| DFNB39 | 60 |
| DFNB40 | 60 |
| DFNB5 | 60 |
| DFNM1 | 60 |
| DHCR24 | 8 |
| DIA1 | 133 |
| DIABLO | 154 |
| DIAPH1 | 60 |
| DIO2 | 150 |
| DIRC2 | 157 |
| DISC1 | 29, 62, 162 |
| DISC2 | 162 |
| DJ1 | 144 |
| DKK3 | 133 |
| DLAT | 47 |
| DLD | 128 |
| DLEC1 | 83, 110 |
| DLEU1 | 109 |
| DLEU2 | 109 |
| DLGAP2 | 82 |
| DLST | 8 |
| DMBT1 | 51, 83, 110, 133, 154, 167 |
| DMD | 129 |
| DMT1 | 61 |
| DNASE1 | 58, 111 |
| DNMT1 | 30, 31, 51, 176, 152, 154, 157, 88, 90, 110 |
| DNMT3B | 30, 51, 88, 133, 157, 167, 90, 109, 110 |
| DNTT | 109 |
| DOK1 | 109 |
| DP1 | 152 |
| DPH2L1 | 31 |
| DPM3 | 154 |
| DPP4 | 4, 51, 64, 154, 161, 92, 118, 132 |
| DPYD | 30, 31, 51, 83, 106, 157 |
| DPYSL5 | 110 |
| DRD1 | 8, 29, 98, 144, 162 |
| DRD2 | 8, 110, 162, 167 |
| DRD3 | 23, 29, 73, 144, 162 |
| DRD4 | 12, 23, 29, 144, 162 |
| DRD5 | 23, 24, 29, 144, 162 |
| DSC3 | 31 |
| DSCAM | 70 |
| DSCR1 | 8, 70 |
| DSCR3 | 70 |
| DSCR5 | 70 |
| DSCR8 | 70, 118 |
| DSG1 | 83 |
| DSP | 31, 129 |
| DSPP | 60 |
| DSTN | 8 |
| DTNBP1 | 162 |
| DTR | 51, 68, 110, 122, 134, 154 |
| DTYMK | 31 |
| DUSP1 | 30, 31, 51, 154 |
| DUT | 51 |
| DYRK1A | 70 |
| DYSF | 129 |
| DYT1 | 144 |
| DYT3 | 144 |
| DYX1 | 73 |
| DYX2 | 73 |
| DYX3 | 73 |
| DYX5 | 73 |
| DYX6 | 73 |
| E2F4 | 31, 51, 79, 109, 154, 180 |
| EB-1 | 109 |
| EBAG9 | 30, 31, 83, 133, 140 |
| EBNA1BP2 | 75 |
| ECA1 | 82 |
| ECE1 | 51, 79 |
| ECGF1 | 30, 31, 51, 129 |
| ED1 | 118, 166 |
| EDN1 | 110 |
| EDN2 | 98 |
| EDNRA | 31, 42, 51, 132, 134, 174, 64, 98, 108 |
| EEC2 | 48 |
| EEF1A2 | 31 |
| EEF2 | 8, 31 |
| EFMR | 82 |
| EFNA1 | 31, 51, 110, 118, 157 |
| EFNB2 | 51 |
| EGF | 31, 110, 133 |
| EGFR | 31, 51, 110, 133, 167 |
| EGI | 82 |
| EGI14 | 82 |
| EGR1 | 8, 31, 110, 133 |
| EIF2S1 | 8, 31, 110, 118 |
| EIF3S3 | 31, 154 |
| EIF3S6 | 31, 133 |
| EIF4A1 | 90, 118 |
| EIF4A2 | 88, 112 |
| EIF4E | 31, 51, 110 |
| EIM | 82 |
| EJM1 | 82 |
| EJM2 | 82 |
| ELAC2 | 154 |
| ELAVL2 | 133, 167 |
| ELAVL3 | 77 |
| ELAVL4 | 167 |
| ELF3 | 31, 110, 154 |
| ELL | 109 |
| ELN | 110 |
| ELOVL4 | 113 |
| EMP1 | 31 |
| EMS1 | 31 |
| ENC1 | 51 |
| ENFL2 | 82 |
| ENG | 31, 51, 110, 118, 133, 154 |
| ENO1 | 31, 110, 111 |
| ENO2 | 31, 110, 133, 167 |
| ENO3 | 110 |
| ENPEP | 8, 157 |
| ENPP1 | 64, 132 |
| ENPP2 | 110, 118, 133, 160 |
| ENTPD1 | 93, 109, 112, 118 |
| ENUR1 | 81 |
| ENUR2 | 81 |
| EP300 | 31, 51, 109 |
| EPAS1 | 30, 31, 133, 157 |
| EPB41 | 114 |
| EPB41L3 | 133 |
| EPD | 82 |
| EPHA2 | 31, 51, 110, 157, 118, 133, 154 |
| EPHA3 | 118, 133, 157, 167 |
| EPHA4 | 31 |
| EPHB2 | 167 |

TABLE 9-continued

RELATION OF TARGET GENES TO DISEASE

| Gene Name | Disease Code |
|---|---|
| EPHX1 | 30, 46, 76, 90, 110 |
| EPM2A | 82 |
| EPO | 4, 31, 92, 110, 133, 167 |
| EPOR | 31, 109 |
| EPPS | 82 |
| EPS15 | 109 |
| EPX | 18, 31, 78, 180 |
| ERBB2 | 26, 30, 31, 154, 167, 176, 51, 110, 133 |
| ERBB3 | 31, 51, 110, 154, 166, 118, 133, 140 |
| ERBB4 | 31, 51, 154 |
| ERCC1 | 42, 51, 109, 133 |
| ERCC2 | 27, 83, 110, 118 |
| ERCC5 | 110 |
| ERCC6 | 110 |
| EREG | 30, 51, 140, 154 |
| ERG | 42, 109 |
| ERN1 | 8 |
| ERN2 | 103 |
| ERVWE1 | 4, 8, 92, 123 |
| ESR2 | 31, 110 |
| ESRRA | 31 |
| ETS1 | 31, 51, 110 |
| ETS2 | 31, 42, 51, 70, 90, 154 |
| ETV4 | 31, 110, 133 |
| EVI1 | 109 |
| EVPL | 83 |
| EXO1 | 51 |
| EXTL3 | 31, 51 |
| EYA1 | 37, 60 |
| EYA4 | 60 |
| EZH2 | 109, 112, 154 |
| F10 | 172 |
| F11 | 109, 127, 172 |
| F12 | 88, 172 |
| F13A1 | 48, 49, 56 |
| F2 | 8, 31, 51, 133, 64, 105, 132 |
| F2R | 31, 172 |
| F2RL1 | 31 |
| F3 | 4, 8, 31, 133, 51, 64, 132 |
| F5 | 53, 103, 127, 168, 172 |
| F7 | 64, 127, 132, 172 |
| F8 | 87 |
| F9 | 87 |
| FAAH | 31 |
| FABP1 | 154 |
| FABP2 | 53, 64, 97, 105, 132, 134 |
| FABP3 | 31, 127 |
| FABP4 | 30, 176 |
| FABP5 | 30, 155 |
| FABP7 | 31 |
| FACL4 | 51 |
| FADD | 51, 64, 105, 133 |
| FADS1 | 134 |
| FADS2 | 31, 109, 113 |
| FANCA | 31 |
| FAP | 118 |
| FASN | 31, 51, 110, 152, 154, 180 |
| FBL | 90, 160 |
| FBLN5 | 31, 51, 112, 157 |
| FBN1 | 14 |
| FBN2 | 14 |
| FBP1 | 64, 132 |
| FBXW7 | 31, 79 |
| FCAR | 18, 92 |
| FCER2 | 18, 20, 88, 123, 160, 92, 109, 111 |
| FCGR1A | 112 |
| FCGR2A | 123 |
| FCGR2B | 111, 112, 118 |
| FCGR3A | 4, 111 |
| FCGR3B | 18, 111, 161, 171 |
| FDXR | 51 |
| FES | 31, 109, 110, 112, 118 |
| FGA | 9, 21, 172 |
| FGB | 52, 53, 98, 127, 146, 172 |
| FGF1 | 31, 53, 64, 109, 154 |
| FGF3 | 31, 110, 167 |
| FGF5 | 31, 154, 157 |
| FGF6 | 154 |
| FGF8 | 31, 154 |
| FGFR1 | 8, 31, 51, 133 |
| FGFR2 | 30, 31, 79, 154 |
| FGFR3 | 30, 42, 51, 109, 122, 176 |
| FGFR4 | 31, 51, 150 |
| FGG | 172 |
| FGL2 | 88 |
| FH | 157 |
| FHIT | 31, 42, 110, 133 |
| FHL2 | 31, 154 |
| FIGF | 31, 51, 110 |
| FIMG1 | 124 |
| FKBP1A | 92 |
| FKBP1B | 186 |
| FKBP4 | 31 |
| FKBP5 | 154 |
| FLG | 155, 160 |
| FLJ11383 | 51 |
| FLJ14813 | 171 |
| FLJ22795 | 51, 110 |
| FLT1 | 31, 51, 110, 133 |
| FLT3 | 109 |
| FLT3LG | 16, 109, 111, 112, 157, 160 |
| FLT4 | 31, 51, 90, 133, 154, 109, 110, 112 |
| FMR1 | 24, 84 |
| FMR2 | 84 |
| FN1 | 31, 51 |
| FOLH1 | 154 |
| FOLR2 | 109 |
| FOS | 8, 31, 92, 110, 123, 133 |
| FOSB | 31 |
| FOSL1 | 31, 42, 51, 83, 110, 167 |
| FOSL2 | 31 |
| FOXA2 | 64, 132 |
| FOXN1 | 6 |
| FOXP3 | 64, 105 |
| FPEVF | 82 |
| FPGS | 51, 109 |
| FPR1 | 92 |
| FPRL1 | 8 |
| FRAT1 | 31, 42, 83 |
| FRDA | 64, 132 |
| FRK | 31 |
| FRZB | 31 |
| FSHB | 30, 92, 102, 150 |
| FSHR | 102 |
| FST | 107, 150 |
| FTH1 | 31 |
| FTL | 8, 37, 144 |
| FURIN | 31, 51, 92, 110 |
| FUS | 109 |
| FUT1 | 51 |
| FUT3 | 51 |
| FUT4 | 110 |
| FUT7 | 110, 133 |
| FUT8 | 51, 138 |
| FVT1 | 112 |
| FXYD3 | 31 |
| FY | 114, 162 |
| FYN | 92, 109, 112, 157 |
| FZD10 | 51 |
| FZD5 | 109, 160 |
| G22P1 | 30, 31, 42, 109, 111 |
| G6PC | 64, 132 |
| G6PD | 8, 31, 51, 64, 86, 132 |
| G72 | 162 |
| GABBR1 | 82 |
| GABRA1 | 82 |
| GABRA3 | 29, 47, 82, 123 |
| GABRA5 | 29 |
| GABRB3 | 24, 29, 49 |
| GABRG2 | 82 |
| GABRG3 | 24 |
| GAD1 | 8, 64, 82, 105, 144, 162 |

TABLE 9-continued

RELATION OF TARGET GENES TO DISEASE

| Gene Name | Disease Code |
|---|---|
| GAD2 | 64, 66, 82, 174, 105, 132, 162 |
| GADD45A | 109, 110, 118 |
| GADD45B | 110 |
| GADD45G | 109, 110 |
| GAL | 8, 12, 57, 134, 150 |
| GALK1 | 37 |
| GALNT3 | 31, 51 |
| GALT | 79 |
| GAP43 | 8, 10, 29, 62, 162 |
| GAPD | 8, 31, 51, 64, 105 |
| GARP | 31 |
| GAS | 51, 64, 132 |
| GAS6 | 160 |
| GASC1 | 83 |
| GATA1 | 70, 171 |
| GATA2 | 109 |
| GATA3 | 31, 60, 92 |
| GBX2 | 154 |
| GC | 64, 105, 123, 132 |
| GCGR | 64, 85, 98, 105, 132 |
| GCK | 64, 132 |
| GCKR | 64, 132 |
| GCLC | 51, 86, 109 |
| GCNT2 | 37 |
| GCSH | 96 |
| GFAP | 4, 8, 123 |
| GFPT1 | 64, 132 |
| GFRA1 | 116 |
| GFRA2 | 116 |
| GFRA3 | 116 |
| GGH | 109 |
| GHR | 12, 31, 47, 107, 134, 154, 64, 90, 105 |
| GHRHR | 110, 150 |
| GHRL | 12, 64, 132, 134, 150, 154 |
| GIPC2 | 51, 157 |
| GIPR | 57 |
| GJA3 | 37 |
| GJA4 | 31, 110 |
| GJA8 | 37 |
| GJB1 | 51 |
| GJB2 | 30, 31, 60, 155, 79, 90, 118 |
| GJB3 | 60 |
| GJB6 | 60 |
| GLDC | 96 |
| GLI | 27, 112 |
| GLI2 | 27 |
| GLP1R | 64, 132 |
| GLUL | 8, 90, 123 |
| GNA11 | 150 |
| GNAI2 | 110, 150, 186 |
| GNAL | 29, 162 |
| GNAO1 | 8 |
| GNAQ | 8, 150 |
| GNAS | 57, 150, 154 |
| GNAT2 | 113 |
| GNB3 | 8, 29, 53, 127, 132, 134, 64, 65, 98 |
| GNE | 129 |
| GNMT | 90 |
| GNRH2 | 31, 79 |
| GNRHR | 118, 154 |
| GOLGA5 | 173 |
| GOLGB1 | 92, 160 |
| GP9 | 171 |
| GPA33 | 51 |
| GPC1 | 31 |
| GPC3 | 31, 90 |
| GPD2 | 64, 132 |
| GPI | 86, 160 |
| GPR1 | 92 |
| GPR15 | 4, 92 |
| GPR2 | 5, 20, 118, 155 |
| GPR30 | 31 |
| GPR37 | 109 |
| GPR44 | 20, 92 |
| GPRK5 | 91, 98, 160 |
| GPT | 47, 88 |
| GPX1 | 86, 110, 154 |
| GPX4 | 102 |
| GRB2 | 8, 31, 109 |
| GRB7 | 31, 83 |
| GRIA1 | 8, 77, 82, 162 |
| GRIA2 | 8, 77, 82, 162 |
| GRIA3 | 29, 77, 82 |
| GRIA4 | 8, 77, 82 |
| GRIK1 | 10, 70, 77, 82 |
| GRIK2 | 82 |
| GRIK3 | 77, 162 |
| GRIK4 | 82, 162 |
| GRIK5 | 82, 162 |
| GRIN1 | 8, 10, 29, 62, 82, 162 |
| GRIN2B | 8, 77, 162 |
| GRM2 | 162 |
| GRM3 | 29, 162 |
| GRM5 | 10, 162 |
| GRM7 | 162 |
| GRN | 31 |
| GRP | 51, 71, 83, 110, 154, 167 |
| GRP58 | 102 |
| GRPR | 31, 51, 110, 154 |
| GSBS | 95 |
| GSE | 38 |
| GSK3A | 90 |
| GSN | 9, 30, 31, 154, 58, 110, 133 |
| GSR | 8, 31, 51, 110, 167, 64, 86, 105 |
| GSS | 86 |
| GSTA1 | 30, 51, 57, 154 |
| GSTA2 | 31 |
| GSTM1 | 31, 110, 133, 167 |
| GSTM3 | 18, 27, 31, 51, 110, 123 |
| GSTP1 | 31, 110, 133, 167 |
| GSTT1 | 30, 31, 51, 110 |
| GUCA2A | 51, 106 |
| GUCA2B | 51, 151 |
| GUCY2C | 51, 83 |
| GUSB | 8, 31, 51, 110 |
| GYPC | 114 |
| GYS1 | 64, 132, 134 |
| GZMA | 75, 92, 160 |
| GZMB | 31, 92 |
| HADH2 | 8 |
| HADHA | 186 |
| HAGH | 157 |
| HARS | 92 |
| HAS1 | 122 |
| HAS2 | 154 |
| HAS3 | 154 |
| HBA1 | 7, 64, 105 |
| HBA2 | 7, 163 |
| HBB | 28, 114, 163 |
| HBD | 163 |
| HBG1 | 28 |
| HBG2 | 28, 163 |
| HBZ | 7, 28 |
| HCK | 92, 109 |
| HD | 8, 51 |
| HDAC1 | 31, 109 |
| HDGF | 83, 90 |
| HDPA | 93 |
| HES1 | 31 |
| HF1 | 30, 160 |
| HFE | 28, 47, 64, 88, 105, 144 |
| HGFAC | 51 |
| HIC1 | 31, 51, 83, 133, 109, 110, 112 |
| HIP1 | 51, 109, 154 |
| HIST4H4 | 31, 84, 111 |
| HK1 | 64, 86, 132 |
| HK2 | 64, 132, 134 |
| HLA-A | 51, 64, 83, 118, 157, 162, 88, 92, 105 |
| HLA-B | 4, 8, 92, 123 |
| HLA-C | 42, 51, 64, 156, 118, 123, 155, 83, 92, 105 |
| HLA-DMB | 64, 105, 123, 160 |
| HLA-DPB1 | 38, 48, 64, 123, 124, 160, 93, 105, 109 |

TABLE 9-continued
RELATION OF TARGET GENES TO DISEASE

| Gene Name | Disease Code |
| --- | --- |
| HLA-DQA1 | 64, 105, 132 |
| HLA-DQB1 | 64, 105, 123, 132 |
| HLA-DRA | 123 |
| HLA-DRB1 | 64, 88, 105, 160, 174, 111, 123, 156 |
| HLA-DRB3 | 51, 56, 64, 123, 132, 92, 105, 111 |
| HLA-DRB4 | 38, 47, 109, 125 |
| HLA-DRB5 | 64, 105, 109, 123 |
| HLA-E | 59, 64, 77, 105, 123 |
| HLA-G | 92, 109, 112, 118, 157, 166 |
| HLF | 109 |
| HLXB9 | 109 |
| HMBS | 26, 83, 112 |
| HMGA1 | 31, 51, 110 |
| HMGA2 | 79, 110 |
| HMGB1 | 31, 90, 180 |
| HMGCR | 8, 31, 51, 132, 64, 95, 110 |
| HMMR | 31, 51, 109, 112, 122 |
| HMOX1 | 8, 123, 127, 144, 157 |
| HMOX2 | 155 |
| HN | 8 |
| HNF4A | 64, 90, 132 |
| HNMT | 18, 70, 72, 161, 162 |
| HNRPA1 | 92, 109 |
| HNRPA2B1 | 83, 92, 110, 167, 111, 133, 160 |
| HOXA1 | 24, 31, 110 |
| HOXA10 | 102, 109, 133 |
| HOXA11 | 109, 171 |
| HOXA13 | 109 |
| HOXA3 | 109 |
| HOXA4 | 109, 157 |
| HOXA5 | 109 |
| HOXA6 | 109 |
| HOXA7 | 109, 110 |
| HOXA9 | 109 |
| HOXB2 | 109 |
| HOXB3 | 109 |
| HOXB4 | 109, 157 |
| HOXB5 | 109, 157 |
| HOXB6 | 51, 109 |
| HOXB7 | 31, 109 |
| HOXB8 | 51 |
| HOXB9 | 157 |
| HOXC11 | 157 |
| HOXC4 | 27, 157, 166 |
| HOXC5 | 42, 112 |
| HOXC8 | 42, 51 |
| HOXD11 | 109 |
| HOXD13 | 109 |
| HOXD3 | 110 |
| HOXD4 | 157 |
| HOXD8 | 64, 105 |
| HP | 31, 64, 92, 105, 141 |
| HPCQTL19 | 154 |
| HPCX | 154 |
| HPN | 154 |
| HPRT1 | 107, 109, 110, 118, 123 |
| HPSE | 83 |
| HR | 6 |
| HRAS | 30 |
| HRASLS | 31, 110, 118, 157 |
| HRC | 64, 132 |
| HRG | 4, 18, 46, 107, 127 |
| HRH1 | 8, 18, 183 |
| HRH2 | 8 |
| HRH3 | 144 |
| HSAJ2425 | 31, 109 |
| HSD11B1 | 134 |
| HSD11B2 | 3, 98 |
| HSD17B1 | 31, 51, 154 |
| HSD17B2 | 51, 79, 154 |
| HSD17B3 | 154 |
| HSD3B1 | 98, 154 |
| HSD3B2 | 154 |
| HSD3B7 | 45 |
| HSF1 | 31, 154 |
| HSF4 | 37 |
| HSPA5 | 31, 51, 160 |
| HSPA8 | 8, 31, 100 |
| HSPB1 | 8 |
| HSPCA | 31, 112 |
| HSPCB | 31, 111 |
| HSPD1 | 8, 64, 105 |
| HSPG2 | 8, 31, 110, 133 |
| HT | 174 |
| HTNB | 98 |
| HTR1A | 8, 29, 62, 64, 132, 162 |
| HTR1B | 110, 120 |
| HTR1D | 120 |
| HTR1F | 73, 120 |
| HTR2A | 8, 12, 23, 120, 162, 24, 29, 62 |
| HTR2B | 120 |
| HTR2C | 29, 120, 162 |
| HTR3A | 29, 162 |
| HTR6 | 8, 29, 162 |
| HVEC | 4 |
| HYAL1 | 154 |
| HYAL2 | 110, 133, 167 |
| HYMAI | 64 |
| HYPLIP1 | 97 |
| HYPLIP2 | 97 |
| HYT1 | 98 |
| HYT2 | 98 |
| HYT3 | 98 |
| IAPP | 9, 58, 64, 132, 134 |
| IBMPFD | 61, 129, 139 |
| IBSP | 31, 51, 110, 122, 154 |
| ICA1 | 64, 105 |
| ICAM2 | 56, 92, 160, 180 |
| ICAM3 | 56, 92, 93, 160, 174, 180, 111, 112, 123 |
| ID1 | 31, 42, 79, 154, 83, 118, 141 |
| IDDM1 | 64, 105 |
| IDDM10 | 64, 105 |
| IDDM11 | 64, 105 |
| IDDM12 | 64, 105 |
| IDDM13 | 64, 105 |
| IDDM15 | 64, 105 |
| IDDM17 | 64, 105 |
| IDDM18 | 64, 105 |
| IDDM2 | 64, 105 |
| IDDM3 | 64, 105 |
| IDDM4 | 64, 105 |
| IDDM5 | 64, 105 |
| IDDM6 | 64, 105 |
| IDDM7 | 64, 105 |
| IDDM8 | 64, 105 |
| IDDMX | 64, 105 |
| IDE | 8, 64, 132 |
| IDS | 84 |
| IFNA1 | 4, 79, 88, 157, 92, 109, 118 |
| IFNA2 | 51 |
| IFNB1 | 4, 31, 51, 123, 133, 110, 115, 118, 77, 91, 92 |
| IFNG | 31, 42, 51, 178, 110, 133, 167 |
| IFNGR1 | 47, 92, 111, 114, 125, 178 |
| IFNGR2 | 125 |
| IGES | 18 |
| IGF1 | 31, 51, 60, 133, 105, 110, 132, 64, 67, 92 |
| IGF1R | 31, 110, 118, 154 |
| IGF2 | 4, 8, 31, 110, 132, 51, 64, 105 |
| IGF2R | 31, 51, 90, 110 |
| IGFALS | 47, 64, 105 |
| IGFBP1 | 31, 51, 64, 105, 132 |
| IGFBP2 | 31, 51, 64, 134, 105, 110, 132 |
| IGFBP4 | 31, 51, 64, 154, 107, 110, 132 |
| IGFBP5 | 31, 42, 64, 154, 79, 105, 107 |
| IGFBP6 | 133, 154 |
| IGFBP7 | 31, 154 |
| IGSF4 | 31, 90, 110, 133, 154 |
| IKBKB | 64, 132 |
| IL10 | 4, 8, 31, 133, 178, 110, 112, 123, 92, 105, 106, 35, 51, 64 |
| IL10RA | 133, 155 |
| IL12A | 20, 56, 92, 118, 123, 154 |

TABLE 9-continued

RELATION OF TARGET GENES TO DISEASE

| Gene Name | Disease Code |
|---|---|
| IL12B | 64, 92, 105, 123, 154 |
| IL13 | 4, 18, 31, 105, 123, 159, 51, 64, 92 |
| IL13RA1 | 93, 175 |
| IL13RA2 | 18, 175 |
| IL15 | 31, 92, 110, 167 |
| IL16 | 18, 56, 92, 112, 160 |
| IL18 | 31, 51, 64, 92, 105, 123 |
| IL1A | 4, 8, 31, 133, 105, 110, 123, 75, 90, 92, 51, 61, 64 |
| IL1B | 31, 110, 167 |
| IL1R1 | 64, 105, 135 |
| IL1R2 | 135 |
| IL1RL1 | 111 |
| IL1RN | 4, 8, 31, 132, 167, 110, 118, 123, 64, 92, 105 |
| IL21R | 112 |
| IL24 | 104, 110, 118, 133 |
| IL2RA | 31, 51, 64, 133, 155, 167, 92, 105, 123 |
| IL2RB | 92, 109, 110, 118, 162 |
| IL2RG | 56, 77, 123 |
| IL3 | 4, 8, 31, 109, 123, 133 |
| IL3RA | 92, 109 |
| IL4 | 4, 8, 31, 133, 105, 110, 123, 51, 64, 92 |
| IL4R | 18, 64, 105, 112, 123, 157 |
| IL5 | 31, 64, 92, 133, 105, 110, 123 |
| IL6R | 4, 31, 42, 127, 150, 112, 122, 123, 56, 77, 92 |
| IL6ST | 4, 8, 31, 92, 110, 133 |
| IL7 | 51, 92 |
| IL7R | 92, 109 |
| IL8 | 4, 31, 51, 110, 123, 133, 64, 92, 105 |
| IL8RA | 59 |
| IL8RB | 4, 92, 154, 155, 178 |
| ILK | 31, 65, 152, 154 |
| ILVASC | 6 |
| IMP-1 | 31, 51 |
| IMP-2 | 47, 90 |
| INA | 109, 112 |
| ING1 | 31, 83, 118 |
| INHBB | 102 |
| INPPL1 | 64, 132 |
| INS | 8, 64, 85, 132, 134, 92, 98, 105 |
| INSM1 | 110 |
| INSR | 8, 31, 64, 132, 134, 85, 105, 129 |
| IPF1 | 64, 132 |
| IRF1 | 110, 133 |
| IRF2 | 123 |
| IRF4 | 122 |
| IRS1 | 64 |
| IRS2 | 31, 64, 85, 132, 134 |
| IRTA1 | 112, 122 |
| ISGF3G | 31, 109, 118 |
| ISL1 | 64, 132, 134 |
| ITGA11 | 133 |
| ITGA2 | 31, 51, 110, 127, 169, 171 |
| ITGA2B | 53, 64, 127, 154, 171 |
| ITGA3 | 31, 51, 79, 118, 154 |
| ITGA4 | 31, 92, 123 |
| ITGA5 | 35, 51, 90, 133, 118, 155, 109, 112, 122 |
| ITGA6 | 27, 31, 51, 175, 154, 160, 166, 90, 110, 142 |
| ITGA7 | 129 |
| ITGA9 | 110, 133, 167 |
| ITGAL | 4, 51, 92, 123 |
| ITGAM | 4, 8, 31, 92, 123 |
| ITGAX | 92 |
| ITGB1 | 4, 31, 51, 167, 110, 123, 133, 64, 92, 105 |
| ITGB2 | 92, 123 |
| ITGB3 | 40, 41, 51, 172, 127, 154, 171, 102, 111, 118, 53, 67, 92 |
| ITGB5 | 31 |
| ITGB7 | 64, 105, 109, 112, 122 |
| ITM2B | 61 |
| IVL | 31, 42, 75, 155, 83, 110, 133 |
| IVNS1ABP | 104 |
| JAG1 | 42, 60 |
| JAG2 | 42, 83, 122 |
| JAK1 | 31, 122, 154, 157 |
| JAK2 | 31, 51, 109, 154, 122 |
| JAK3 | 20, 109, 112, 157 |
| JRK | 82 |
| JUN | 8, 31, 51, 110, 123, 133 |
| JUNB | 31, 92, 93, 109, 112 |
| JUP | 31, 51, 118, 133 |
| KAI1 | 30, 31, 42, 133, 154, 51, 83, 110 |
| KCNA1 | 31 |
| KCNA5 | 21 |
| KCNE1 | 21 |
| KCNH1 | 31, 42 |
| KCNJ11 | 64, 132 |
| KCNJ2 | 21 |
| KCNJ3 | 31, 64, 132 |
| KCNJ6 | 64, 70, 132 |
| KCNJ8 | 53 |
| KCNJ9 | 64, 132 |
| KCNN3 | 29, 162 |
| KCNN4 | 58 |
| KCNQ1 | 21, 60 |
| KCNQ2 | 82 |
| KCNQ3 | 82 |
| KCNQ4 | 60 |
| KIAA1199 | 60 |
| KIR2DL1 | 92, 155 |
| KIR3DL1 | 4 |
| KISS1 | 31, 118 |
| KIT | 31, 51, 92, 167, 109, 110, 183 |
| KITLG | 31, 51, 92, 110, 133, 167 |
| KL | 107, 136, 157 |
| KLF1 | 28 |
| KLF4 | 31, 51, 152 |
| KLF5 | 31, 53, 154 |
| KLHL4 | 49 |
| KLK1 | 79, 98, 141 |
| KLK10 | 31, 154 |
| KLK11 | 154 |
| KLK13 | 31 |
| KLK2 | 154 |
| KLK3 | 31, 107, 154 |
| KLK4 | 154 |
| KLK5 | 31, 154 |
| KLK6 | 8 |
| KLK8 | 8 |
| KLKB1 | 107 |
| KLRB1 | 123 |
| KLRC1 | 92, 118 |
| KLRD1 | 59, 92, 102, 118 |
| KRAS2 | 51 |
| KRT13 | 30, 42 |
| KRT14 | 31, 110 |
| KRT17 | 42 |
| KRT18 | 31, 47, 110, 133 |
| KRT20 | 31, 51, 110, 154 |
| KRT7 | 31, 45, 47, 110 |
| KRT8 | 47 |
| KRTHB1 | 31 |
| L1CAM | 49, 118 |
| LAF4 | 109 |
| LAMA1 | 8, 51, 67, 110 |
| LAMA3 | 110 |
| LAMA5 | 110 |
| LAMB1 | 51, 154 |
| LAMB2 | 154 |
| LAMB3 | 133, 154 |
| LAMC2 | 51, 83, 133, 166 |
| LAMP1 | 51, 118 |
| LAMP2 | 51, 118 |
| LAMP3 | 31, 51, 83 |
| LAMR1 | 31, 51, 110, 118, 133 |
| LASP1 | 31 |
| LAT | 160 |
| LBP | 133 |
| LCAT | 64, 95, 97, 132 |
| LCK | 51, 64, 75, 167, 109, 110, 157, 83, 92, 105 |
| LCN1 | 58, 110 |
| LCN2 | 17, 51, 56, 69, 103, 180 |
| LCO | 90 |

TABLE 9-continued
RELATION OF TARGET GENES TO DISEASE

| Gene Name | Disease Code |
|---|---|
| LCP1 | 31, 112, 154 |
| LCS1 | 45 |
| LDHA | 31 |
| LDLR | 51, 64, 95, 110, 132 |
| LEF1 | 51, 112, 118 |
| LEP | 31, 64, 85, 133, 134, 92, 105, 132 |
| LEPR | 12, 31, 33, 134, 109, 150, 105, 64, 92, 110 |
| LGALS1 | 30, 31, 51, 110, 154 |
| LGALS3 | 31, 51, 110, 133 |
| LGALS3BP | 31, 88, 92, 133, 106, 110, 112 |
| LGI1 | 82 |
| LHX2 | 109 |
| LIG4 | 31, 109, 122 |
| LILRB1 | 59, 92 |
| LILRB2 | 160 |
| LIM2 | 37 |
| LIPC | 53, 64, 97, 105, 132 |
| LIPE | 64, 97, 132, 134 |
| LMNA | 21, 31, 42, 129, 133, 154, 51, 83, 110 |
| LMNB1 | 31, 42, 51, 83, 133, 154 |
| LMO1 | 109 |
| LMO2 | 109, 110 |
| LMOD1 | 174 |
| LOC90925 | 109 |
| LOH11CR2A | 31, 110 |
| LOR | 142 |
| LOST1 | 110 |
| LOX | 31 |
| LPA | 8, 52 |
| LPL | 8, 64, 105, 132 |
| LPP | 109, 110 |
| LRP1 | 8, 31, 53, 118, 154 |
| LRP2 | 8 |
| LRP5 | 64, 105, 136 |
| LRPAP1 | 8 |
| LTA | 31, 51, 64, 127, 110, 132, 105, 92, 123 |
| LTB | 47, 88, 160 |
| LTB4R | 92 |
| LTC4S | 18, 109, 165 |
| LTF | 4, 8, 31, 92 |
| LUC7L | 7 |
| LUM | 31, 42 |
| LY75 | 31 |
| LYL1 | 109 |
| LYN | 35, 51, 109, 112 |
| LYZ | 9 |
| LZTS1 | 31, 83, 133, 154 |
| MAD | 110, 166 |
| MAD1L1 | 112, 154 |
| MAD2L1 | 31, 109, 112 |
| MADCAM1 | 56, 103, 109, 112, 180 |
| MADH1 | 31, 152 |
| MADH3 | 31, 51, 56, 83, 152, 180 |
| MADH4 | 31, 110, 133, 140, 151 |
| MADH5 | 51, 109 |
| MADH6 | 90 |
| MADH7 | 56, 90, 180 |
| MAF | 37, 122 |
| MAG | 24, 123 |
| MAGEA10 | 118 |
| MAGEA3 | 30, 31, 110, 118 |
| MAGEA4 | 83, 110, 118 |
| MAGEC1 | 118 |
| MAGEE1 | 118 |
| MALT1 | 110, 112, 166 |
| MAOA | 8, 13, 23, 144, 162, 24, 29, 62 |
| MAOB | 8, 10, 23, 162, 24, 29, 144 |
| MAP1B | 8 |
| MAP2 | 8, 82, 118, 144, 162 |
| MAP2K1 | 8, 31, 51, 110 |
| MAP2K3 | 46, 137, 154 |
| MAP2K4 | 31, 51, 154 |
| MAP2K5 | 154 |
| MAP2K6 | 8 |
| MAP3K1 | 79, 154 |
| MAP3K3 | 90 |
| MAP3K4 | 31 |
| MAP3K8 | 31 |
| MAP4 | 31 |
| MAPK1 | 31, 51, 110 |
| MAPK10 | 8 |
| MAPK11 | 154 |
| MAPK14 | 31, 51, 64, 132 |
| MAPK3 | 8, 31, 51, 92, 133, 167 |
| MAPK6 | 154 |
| MAPK8 | 31 |
| MAPK8IP1 | 64 |
| MAPKAPK2 | 31 |
| MAPKAPK3 | 110 |
| MAPT | 8, 61, 70, 144 |
| MAT1A | 90 |
| MAT2A | 90 |
| MATK | 31 |
| MATN3 | 135 |
| MAX | 31 |
| MAZ | 135 |
| MBD1 | 51, 110 |
| MBD2 | 31, 51, 154 |
| MBD4 | 51 |
| MBL2 | 4, 58, 88, 92, 114, 163 |
| MBP | 4, 8, 24, 61, 123 |
| MC1R | 27, 118, 154, 166 |
| MC2R | 3 |
| MC3R | 134 |
| MC4R | 12, 33, 134 |
| MCC | 31, 51, 83, 110, 152 |
| MCP | 91, 110, 123 |
| MDK | 8, 51, 71, 106, 110 |
| MDM1 | 60 |
| MDM2 | 31, 51, 110, 133 |
| MDS1 | 109 |
| ME1 | 31 |
| MEAX | 129 |
| MEBA | 82 |
| MECP2 | 24, 133 |
| MEF2A | 52 |
| MEFV | 9 |
| MEIS1 | 109 |
| MEN1 | 31, 36, 110, 167 |
| MEP1A | 51 |
| MEST | 31, 51, 110 |
| MET | 90, 157 |
| MFGE8 | 31 |
| MFI2 | 8, 118 |
| MGAT3 | 47, 90 |
| MGAT5 | 51, 88, 90, 118 |
| MGP | 127 |
| MGR1 | 120 |
| MGR2 | 120 |
| MGR3 | 120 |
| MGR4 | 120 |
| MGR5 | 120 |
| MGR6 | 120 |
| MGST1 | 110 |
| MHC2TA | 64, 77, 92, 123, 160, 167, 105, 110, 112 |
| MIA | 51, 118, 157 |
| MICA | 1, 38, 56, 166, 178, 180, 64, 105, 155 |
| MIP | 37 |
| MIPS | 127 |
| MITF | 60, 118 |
| MJD | 82, 144 |
| MKKS | 53 |
| MKL1 | 109 |
| MLANA | 110, 118, 157, 166 |
| MLC1 | 61, 162, 184 |
| MLF1 | 109 |
| MLH1 | 31, 51, 103, 166, 110, 133, 151 |
| MLH3 | 51 |
| MLLT1 | 109 |
| MLLT10 | 109, 112 |
| MLLT2 | 109 |
| MLLT3 | 109 |

TABLE 9-continued

RELATION OF TARGET GENES TO DISEASE

| Gene Name | Disease Code |
|---|---|
| MLLT4 | 109 |
| MLLT6 | 109 |
| MLLT7 | 109 |
| MLN | 64, 66 |
| MLN51 | 31 |
| MME | 8, 110, 133, 167 |
| MMP1 | 31, 51, 110 |
| MMP10 | 31, 51, 67, 166 |
| MMP12 | 46, 51 |
| MMP13 | 14, 31, 42, 160, 166, 83, 118, 135 |
| MMP15 | 90 |
| MMP16 | 118 |
| MMP2 | 4, 8, 10, 144, 167, 123, 132, 133, 64, 110, 118, 31, 51, 61 |
| MMP26 | 79, 110, 154 |
| MMP3 | 31, 51, 56, 123, 167, 180 |
| MMP8 | 118, 160 |
| MMP9 | 31, 51, 110, 112, 133 |
| MNT | 31 |
| MOBP | 123 |
| MOG | 24, 123 |
| MPD1 | 129 |
| MPD2 | 129 |
| MPG | 31, 42, 102 |
| MPL | 171 |
| MPO | 8, 110, 123, 167 |
| MPRM | 129 |
| MPZ | 112 |
| MRE11A | 31, 112 |
| MRPL28 | 118 |
| MRXE | 82 |
| MS4A1 | 92 |
| MS4A2 | 18 |
| MSF | 31, 109 |
| MSH2 | 31, 51, 79, 151, 154, 106, 112, 13 8 |
| MSH3 | 31, 51, 79, 152, 109, 167, 83, 133 |
| MSH6 | 51, 138, 151 |
| MSLN | 31, 42, 51, 79, 83, 110 |
| MSMB | 154 |
| MSN | 70, 92, 160 |
| MSR1 | 8, 97, 154 |
| MSSE | 27 |
| MST1 | 110, 157, 167 |
| MST1R | 31, 51, 110, 133 |
| MSX1 | 48, 49 |
| MT1B | 31 |
| MT1E | 31, 154 |
| MT1X | 30, 31, 154 |
| MT2A | 31, 135, 154 |
| MT3 | 8, 31, 154 |
| MTA1 | 31 |
| MTAP | 109, 110, 133 |
| MTATP6 | 88 |
| MTBS1 | 178 |
| MTBSX | 178 |
| MTCO2 | 8, 51, 100, 129 |
| MTCP1 | 109 |
| MTHFR | 8, 31, 51, 132, 53, 64, 110 |
| MTM1 | 129 |
| MTND5 | 8, 129, 144 |
| MTNR1A | 8 |
| MTP | 95 |
| MTR | 51, 70 |
| MTRR | 70, 117 |
| MUC1 | 31, 110, 133 |
| MUC3A | 56, 180 |
| MUC4 | 26, 51, 106, 110, 133, 141 |
| MUC5B | 58, 110, 133 |
| MUC6 | 26, 31, 51, 56, 110 |
| MUC8 | 102, 110, 165 |
| MUSK | 124 |
| MVK | 90 |
| MX1 | 88, 104, 123, 143, 159 |
| MXI1 | 154, 167 |
| MYAS1 | 124 |
| MYBL1 | 35, 109, 112 |
| MYBL2 | 154 |
| MYBPC3 | 129 |
| MYCL1 | 30, 31, 42, 122, 133, 51, 83, 110 |
| MYCN | 110, 167 |
| MYF6 | 129 |
| MYH2 | 129 |
| MYH6 | 100, 129 |
| MYH7 | 100, 129 |
| MYH9 | 60 |
| MYL2 | 100, 129 |
| MYL3 | 100 |
| MYL4 | 127 |
| MYLK2 | 129 |
| MYO15A | 60 |
| MYO18B | 110 |
| MYO1A | 60 |
| MYO1G | 109 |
| MYO3A | 60 |
| MYO6 | 60 |
| MYO7A | 60 |
| MYOD1 | 31, 51 |
| MYST3 | 109 |
| N33 | 51, 110, 154 |
| NAP1 | 107 |
| NBL1 | 31 |
| NBS1 | 31, 109, 112 |
| NCAM1 | 8, 24, 31, 133, 167, 51, 92, 110 |
| NCAM2 | 70 |
| NCF1 | 134 |
| NCF2 | 8, 56, 64, 132 |
| NCKAP1 | 8 |
| NCL | 92, 109, 111 |
| NCOA1 | 31 |
| NCOA2 | 31, 109, 154 |
| NCOA3 | 31, 79, 109, 154 |
| NCOA4 | 31, 154, 173 |
| NCOR1 | 31 |
| NCOR2 | 31, 109 |
| NCSTN | 8 |
| NDP | 60 |
| NDRG1 | 51 |
| NDUFV2 | 144 |
| NEB | 129 |
| NEDD5 | 8, 109 |
| NEF3 | 8, 10, 144 |
| NEFH | 10 |
| NEFL | 8, 10, 31, 154, 70, 61, 123 |
| NEK4 | 31 |
| NES | 118 |
| NEUROD1 | 64, 105, 132 |
| NEUROG3 | 64, 132 |
| NF1 | 31, 51, 110, 118, 167 |
| NFKB1 | 31, 92, 133 |
| NFKB2 | 31, 109, 112, 122 |
| NFKBIA | 31, 51, 92, 110, 133 |
| NFKBIL1 | 123, 160, 180 |
| NGFB | 8, 123, 154 |
| NGFR | 8, 31, 92, 123, 144 |
| NHLRC1 | 82 |
| NID | 67 |
| NIDDM2 | 64 |
| NIDDM3 | 64 |
| NISCH | 98 |
| NKX3-1 | 154 |
| NLGN3 | 24 |
| NLGN4 | 24 |
| NMB | 51 |
| NME1 | 31, 90, 110, 133 |
| NME2 | 51, 110, 118 |
| NMT1 | 30, 51, 92 |
| NMTC1 | 173 |
| NOL1 | 31, 51, 110, 154 |
| NONO | 157 |
| NOS1 | 8, 10, 18, 98, 144 |
| NOS2A | 4, 8, 31, 114, 132, 133, 98, 105, 110, 64, 88, 92, 51, 58, 61 |

TABLE 9-continued
RELATION OF TARGET GENES TO DISEASE

| Gene Name | Disease Code |
|---|---|
| NOS3 | 8, 31, 54, 64, 110, 132 |
| NOTCH1 | 42, 51, 109, 167 |
| NOV | 3, 31, 154, 157 |
| NP | 18, 109, 112, 174 |
| NPHP1 | 107 |
| NPPA | 64, 98, 105, 132, 167 |
| NPPC | 107 |
| NPR3 | 51, 98 |
| NPY | 8, 31, 64, 92, 132 |
| NPY2R | 82 |
| NPY5R | 134 |
| NQO1 | 8, 30, 31, 133, 154, 182, 51, 109, 110 |
| NR0B1 | 3 |
| NR0B2 | 64, 132, 134 |
| NR1I2 | 31 |
| NR2C1 | 31, 142, 163 |
| NR2F1 | 3, 57 |
| NR2F2 | 3, 31, 57 |
| NR2F6 | 31 |
| NR3C1 | 4, 8, 31, 167, 110, 132, 134, 57, 64, 92 |
| NR3C2 | 57, 98 |
| NR4A1 | 31, 110 |
| NR4A2 | 29, 144, 162 |
| NR5A1 | 3, 150 |
| NRAS | 51 |
| NRG1 | 8, 31, 123, 154, 162 |
| NRIP1 | 31 |
| NRP1 | 154 |
| NRP2 | 36 |
| NSEP1 | 31, 133 |
| NSF | 162 |
| NTF3 | 8, 10, 118, 154, 162 |
| NTF5 | 10 |
| NTRK1 | 8, 31, 116, 167, 173 |
| NTRK2 | 8, 10, 154, 162 |
| NTRK3 | 8, 109, 116, 157 |
| NTS | 8, 110, 144, 154, 162, 167 |
| NUFIP1 | 84 |
| NUMA1 | 51, 109 |
| NUP153 | 80, 149 |
| NUP214 | 92, 109 |
| NUP88 | 31, 47, 51, 154, 90, 93, 110 |
| NUP98 | 109 |
| OADIP | 135 |
| OAS2 | 88, 109, 118, 122 |
| OASD | 60 |
| OASF | 135 |
| OATL1 | 157, 171 |
| OB10P | 134 |
| OB10Q | 134 |
| OB4 | 134 |
| OCLN | 56, 74, 92, 180 |
| OGDH | 8 |
| OGG1 | 51, 83, 110, 133, 154, 157 |
| OGT | 51 |
| OLIG2 | 109 |
| OLR1 | 8, 172 |
| OMG | 24, 123 |
| OPHN1 | 51 |
| OPLAH | 110 |
| OPRD1 | 8, 92, 144 |
| OPRK1 | 8, 92 |
| OPRM1 | 8, 144 |
| OQTL | 134 |
| OR51E2 | 154 |
| ORC5L | 109 |
| ORM1 | 31, 110 |
| ORM2 | 31, 110 |
| OSM | 31, 92, 110, 154, 118, 122, 133 |
| OSMR | 31 |
| OTOA | 60 |
| OTOF | 60 |
| OXT | 4, 110, 123, 167 |
| OXTR | 31 |
| P2RX7 | 109 |
| P2RY12 | 172 |
| P2RY2 | 58 |
| P8 | 31, 141 |
| PABPC1 | 55 |
| PACE4 | 31, 92, 110 |
| PADI4 | 160 |
| PAEP | 79, 102 |
| PAH | 162 |
| PAK1 | 31 |
| PAM | 110, 123, 154 |
| PAPPA | 53, 70 |
| PARK10 | 144 |
| PARK11 | 144 |
| PARK2 | 61, 144 |
| PARK3 | 144 |
| PARK4 | 144 |
| PARK6 | 144 |
| PARK8 | 144 |
| PARK9 | 144 |
| PAWR | 8, 10, 144, 154, 157 |
| PAX2 | 157 |
| PAX3 | 60, 118 |
| PAX4 | 64, 132 |
| PAX5 | 112 |
| PAX6 | 30, 37, 51, 64 |
| PAX7 | 110 |
| PBCA | 64, 105 |
| PBOV1 | 30, 31, 51, 110, 154 |
| PBP | 154 |
| PBX1 | 109 |
| PCAF | 31 |
| PCAP | 154 |
| PCBC | 154 |
| PCBD | 51 |
| PCC | 37 |
| PCK1 | 64, 132 |
| PCM1 | 173 |
| PCMT1 | 8, 37 |
| PCNA | 8, 31, 51, 133 |
| PCSK1 | 31, 64, 92, 150, 167, 110, 132, 134 |
| PCSK2 | 24, 64, 110, 132, 167 |
| PCSK7 | 112 |
| PCSK9 | 95 |
| PDB | 139 |
| PDB3 | 139 |
| PDB4 | 139 |
| PDCD1 | 111 |
| PDCD8 | 112, 133 |
| PDE4D | 168 |
| PDE5A | 30, 176 |
| PDGFA | 31 |
| PDGFB | 31, 51 |
| PDGFRA | 27, 106, 109, 166 |
| PDGFRL | 51, 89, 90, 133, 154 |
| PDPK1 | 64, 132 |
| PDYN | 24, 29, 46, 62, 162 |
| PEA15 | 64, 132 |
| PECAM1 | 31, 47, 56, 163, 174, 180, 135, 157, 160, 123, 127, 133, 109, 110, 118 |
| PEPD | 31 |
| PFC | 119 |
| PFKL | 29, 86 |
| PFKM | 64, 132 |
| PFN1 | 31 |
| PGA5 | 22, 145 |
| PGAM2 | 129 |
| PGC | 31, 145 |
| PGF | 51, 70, 110, 118, 157 |
| PGGT1B | 30, 31, 110 |
| PGK1 | 16, 86, 144 |
| PHB | 31 |
| PHF11 | 18 |
| PHKA1 | 109 |
| PI | 47, 76 |
| PI3 | 31, 128, 155 |
| PIAS3 | 112 |
| PICALM | 109 |

TABLE 9-continued

RELATION OF TARGET GENES TO DISEASE

| Gene Name | Disease Code |
| --- | --- |
| PIGR | 51, 110 |
| PIK3CA | 42, 110, 133, 138 |
| PIK3R1 | 31, 51, 64, 93, 132 |
| PIM1 | 112, 154 |
| PIN1 | 8 |
| PIP | 31, 139 |
| PITPNM1 | 113 |
| PITX3 | 37 |
| PKD1 | 31 |
| PKLR | 64, 132 |
| PKM2 | 31, 51, 106, 157, 110, 133, 142 |
| PLA2G10 | 51 |
| PLA2G2A | 51, 118, 141, 152, 154 |
| PLA2G7 | 4, 18, 41 |
| PLAB | 31, 154 |
| PLAGL1 | 31, 64 |
| PLAT | 31, 51, 64, 133, 152, 123, 132, 134, 92, 105, 110 |
| PLAU | 8, 31, 51, 133, 152, 92, 110, 123 |
| PLAUR | 31, 51, 92, 110, 123, 133 |
| PLCB1 | 167 |
| PLCB3 | 36 |
| PLCD1 | 8, 29, 51, 54, 152 |
| PLCG1 | 29, 31, 51, 152 |
| PLCL1 | 110, 133, 167 |
| PLD1 | 31, 51 |
| PLD2 | 31, 51, 157 |
| PLEC1 | 92, 154 |
| PLK | 51, 83, 110, 112, 133 |
| PLP1 | 123 |
| PLTP | 64, 76, 105, 146, 132, 134 |
| PLU-1 | 31 |
| PMS1 | 51, 151 |
| PMS2 | 51, 79, 118, 151, 154 |
| PNCA1 | 140 |
| PNMT | 8, 98, 144 |
| PNOC | 162 |
| POLB | 30, 31, 51, 109, 110, 154 |
| POLG | 102 |
| POLK | 133 |
| POMC | 4, 8, 31, 167, 132, 110, 123, 134, 64, 92, 105 |
| PON1 | 41, 52, 53, 132, 105, 144, 95, 64, 127 |
| PON2 | 41, 52, 53 |
| POR | 3, 31, 110 |
| POU3F4 | 60 |
| POU4F3 | 60 |
| PPARA | 30, 64, 97, 132, 154 |
| PPARD | 51, 95 |
| PPARGC1 | 64, 132, 134 |
| PPID | 31, 154 |
| PPM1D | 31, 154 |
| PPND | 61, 144 |
| PPP1CC | 31 |
| PPP1R15A | 118 |
| PPP1R3A | 51, 64, 132, 133, 167 |
| PPP2CB | 31 |
| PPP2R1B | 31, 51, 110 |
| PRCC | 157 |
| PRDM2 | 31, 51, 79, 90, 110, 112 |
| PRDX1 | 8, 70, 109 |
| PREP | 8 |
| PRF1 | 14, 51, 88, 92, 122, 123 |
| PRG2 | 18, 174 |
| PRKAA2 | 64, 132 |
| PRKAG2 | 129, 144 |
| PRKAR1A | 31, 57, 111, 150, 154, 173 |
| PRKCA | 8, 31, 51, 150, 64, 110, 132 |
| PRKCD | 154, 157 |
| PRKCE | 8, 31, 51, 154, 167, 92, 110, 133 |
| PRKCG | 8, 31, 51, 154 |
| PRKCL1 | 8 |
| PRKCM | 31, 110, 167 |
| PRKCQ | 64, 109, 132, 134 |
| PRKCZ | 8, 31 |
| PRKDC | 51, 109 |
| PRKN | 144 |
| PRKR | 8, 31, 51, 118, 187, 91, 92, 109 |
| PRL | 4, 12, 31, 105, 111, 123, 51, 64, 92 |
| PRLR | 31, 150, 154 |
| PRM1 | 102 |
| PRM2 | 102 |
| PRND | 8 |
| PRNP | 8, 61 |
| PRODH | 162 |
| PROM1 | 109 |
| PROMM | 129 |
| PROS1 | 172 |
| PROZ | 41 |
| PRSS1 | 51, 141 |
| PRSS2 | 141 |
| PRSS8 | 31, 154 |
| PRTN3 | 56, 58, 92, 180, 109, 111, 160 |
| PRY | 102 |
| PSDA | 24 |
| PSEN1 | 8, 9, 39, 70, 61 |
| PSEN2 | 8, 61 |
| PSG1 | 70 |
| PSMB8 | 64, 105, 118, 174 |
| PSMB9 | 64, 105, 118, 174 |
| PSORS1 | 155 |
| PSORS2 | 155 |
| PSORS3 | 155 |
| PSORS4 | 155 |
| PSORS5 | 155 |
| PSORS6 | 155 |
| PSORS7 | 155 |
| PTAFR | 18, 31, 50, 51, 118 |
| PTCH | 27, 30, 31, 83, 166 |
| PTCH2 | 27 |
| PTCPRN | 173 |
| PTCRA | 31 |
| PTEN | 31, 51, 79, 167, 173, 110, 133, 154 |
| PTGER2 | 42, 79 |
| PTGER4 | 30, 42, 51, 79 |
| PTGES | 51 |
| PTGIS | 98, 127 |
| PTGS1 | 31, 51, 133 |
| PTH | 3, 4, 31, 136, 98, 110, 132, 51, 64, 92 |
| PTHLH | 31, 110, 133 |
| PTHR1 | 136 |
| PTK2B | 31, 167 |
| PTK6 | 31, 51 |
| PTMA | 31, 51, 110 |
| PTN | 31, 118, 133, 141, 154, 167 |
| PTOV1 | 154 |
| PTPN1 | 8, 31, 64, 134, 83, 98, 132 |
| PTPN13 | 154 |
| PTPN6 | 31, 35, 93, 109, 112 |
| PTPRA | 31, 154 |
| PTPRC | 64, 92, 105, 123 |
| PTPRF | 31, 134 |
| PTPRG | 31, 110, 157 |
| PTPRJ | 31, 51, 56, 110 |
| PTPRN | 64, 85, 105 |
| PTPRN2 | 64, 105 |
| PTTG1 | 31, 51, 110, 150 |
| PURA | 92, 109 |
| PVR | 51 |
| PVRL1 | 48, 91 |
| PXN | 31, 51, 83, 167, 118, 92, 154 |
| PYGM | 31, 113, 150 |
| RAB3A | 8 |
| RABEP1 | 109 |
| RAC1 | 31, 51 |
| RAD50 | 42, 51 |
| RAD51 | 31, 154 |
| RAD51A | 31 |
| RAD51C | 31 |
| RAD51L1 | 110 |
| RAD52 | 31 |
| RAD54B | 93, 112 |
| RAD54L | 31, 51, 93, 112 |
| RAG2 | 111 |

TABLE 9-continued
RELATION OF TARGET GENES TO DISEASE

| Gene Name | Disease Code |
|---|---|
| RAGE | 118, 157, 176 |
| RALA | 30 |
| RAN | 154 |
| RANBP17 | 109 |
| RAP1A | 110, 154 |
| RARG | 31 |
| RASA1 | 27, 51, 110 |
| RASSF1 | 30, 31, 110, 133, 157, 167 |
| RB1 | 30, 31, 51, 110, 167, 133 |
| RB1CC1 | 31 |
| RBBP1 | 31 |
| RBL2 | 31, 35, 79, 110, 112, 133 |
| RBM15 | 109 |
| RBM5 | 110, 133, 167 |
| RBM6 | 110, 167 |
| RBP1 | 31, 79, 107, 166 |
| RBP1L1 | 31, 51, 110 |
| RCBTB1 | 109 |
| RCCP3 | 157 |
| RCV1 | 110, 167 |
| RDS | 113 |
| RDX | 110, 160 |
| REA | 31 |
| RECK | 90 |
| RECQL | 51 |
| REG1A | 51, 141 |
| REL | 31, 92, 93, 112 |
| RELA | 8, 31, 92, 110 |
| RELN | 24, 29, 83, 162 |
| REN | 8, 64, 65, 105, 132 |
| REST | 167 |
| RET | 116, 173 |
| RETN | 64, 132, 134 |
| RFC3 | 51 |
| RFH1 | 98 |
| RFP2 | 109 |
| RGS4 | 162 |
| RHD | 86 |
| RIL | 136 |
| RLF | 110, 167 |
| RLN1 | 31 |
| RLN2 | 31 |
| RNASE1 | 141 |
| RNASE2 | 92 |
| RNASEL | 154 |
| RNF14 | 154 |
| RNF7 | 51, 110, 133 |
| ROBO1 | 31, 110, 157 |
| ROCK1 | 90 |
| RORA | 31, 154 |
| RPA1 | 31, 51, 110, 133 |
| RPGR | 60, 113 |
| RPL13 | 31, 154 |
| RPL19 | 31 |
| RPL29 | 51 |
| RPL30 | 90 |
| RPN1 | 109 |
| RPN2 | 51 |
| RPS6 | 110, 157 |
| RPS6KA1 | 110, 133 |
| RPS6KA3 | 110, 167 |
| RPS6KB1 | 31 |
| RRAD | 31, 64, 132, 134 |
| RRAS | 31 |
| RRAS2 | 31 |
| RSN | 93 |
| RTN1 | 110 |
| RUNX1 | 109, 160 |
| RUNX2 | 136, 154 |
| RXRB | 162, 166 |
| RXRG | 133 |
| RYR1 | 129 |
| RYR2 | 169, 186 |
| S100A1 | 157 |
| S100A2 | 31, 118, 133 |
| S100A6 | 118, 51 |
| S100A7 | 31, 155 |
| S100A9 | 56, 58, 155, 180 |
| S100B | 8, 61 |
| S100P | 31, 56, 154, 180 |
| SAA1 | 9, 160 |
| SAFB | 31 |
| SAH | 98, 134 |
| SARDH | 90 |
| SAT | 31, 118, 133, 154, 167, 180 |
| SC5DL | 134 |
| SCA2 | 123 |
| SCA7 | 113 |
| SCABD | 60 |
| SCARB1 | 3 |
| SCD | 31, 51, 83 |
| SCG2 | 8, 36, 160 |
| SCG3 | 154 |
| SCGB1A1 | 18, 154 |
| SCGB1D2 | 31, 154 |
| SCGB2A2 | 31 |
| SCGB3A1 | 31 |
| SCGB3A2 | 18 |
| SCN10A | 123 |
| SCN1A | 82 |
| SCN1B | 82 |
| SCN4A | 154 |
| SCN5A | 34, 185 |
| SCO2 | 100, 129 |
| SCP2 | 3 |
| SCT | 24 |
| SCTR | 140 |
| SCYE1 | 118 |
| SCZD1 | 162 |
| SCZD10 | 162 |
| SCZD11 | 162 |
| SCZD2 | 162 |
| SCZD3 | 162 |
| SCZD4 | 162 |
| SCZD5 | 162 |
| SCZD6 | 162 |
| SCZD7 | 162 |
| SCZD8 | 162 |
| SCZD9 | 162 |
| SDC1 | 31, 42, 51, 122, 90, 110, 112 |
| SDC2 | 24 |
| SDHD | 36, 60, 106 |
| SE20-4 | 111, 112 |
| SEL1L | 31 |
| SELE | 4, 31, 51, 132, 133, 105, 110, 123, 64, 85, 92 |
| SELL | 4, 64, 92, 132, 105, 110, 109, 123 |
| SELP | 31, 64, 92, 95, 105, 132 |
| SELPLG | 103, 109 |
| SEMA3B | 110, 133, 167 |
| SEMA3C | 110, 160 |
| SEMA3F | 110 |
| SEPP1 | 51, 154 |
| SERPINA1 | 47, 58, 90, 107, 110 |
| SERPINA3 | 8, 31, 110 |
| SERPINA5 | 172 |
| SERPINA7 | 90, 92 |
| SERPINB3 | 155 |
| SERPINB5 | 31, 112, 154 |
| SERPINE1 | 31, 110, 154 |
| SERPINE2 | 8, 102 |
| SERPINF1 | 10, 31, 67, 113 |
| SERPINF2 | 40, 47, 52, 109, 127, 154 |
| SERPING1 | 8, 74, 111, 112, 141, 160 |
| SERPINH1 | 147 |
| SERPINI1 | 61 |
| SERPINI2 | 31 |
| SET | 109 |
| SFN | 31, 90 |
| SFRP1 | 31, 51, 180 |
| SFTPA1 | 110, 159 |
| SFTPA2 | 137, 159 |
| SFTPB | 110 |

TABLE 9-continued

RELATION OF TARGET GENES TO DISEASE

| Gene Name | Disease Code |
|---|---|
| SFTPC | 110 |
| SFTPD | 104, 159, 178 |
| SFXN5 | 144 |
| SGCD | 100, 129 |
| SH2D1A | 16, 75, 88, 160, 101, 109, 112 |
| SHBG | 31, 64, 92, 134, 154, 98, 105, 132 |
| SHC1 | 8, 31, 64, 132 |
| SHFM1D | 60 |
| SHH | 27, 49, 110, 166 |
| SHOX | 179 |
| SI | 26, 56, 74, 83 |
| SIAH1 | 31, 51, 90, 154 |
| SIAT6 | 31, 51 |
| SIAT8A | 118 |
| SIAT8B | 110, 133 |
| SIAT9 | 30, 118, 176 |
| SIL | 109 |
| SILV | 118 |
| SIM1 | 134 |
| SIM2 | 70 |
| SKP2 | 31, 51, 90, 109, 110, 112 |
| SLC11A1 | 56, 178, 180 |
| SLC16A1 | 51 |
| SLC18A2 | 144, 162 |
| SLC18A3 | 8 |
| SLC19A1 | 31, 109 |
| SLC19A2 | 64, 117 |
| SLC1A1 | 10, 29, 82, 162 |
| SLC1A2 | 8, 10, 82, 162 |
| SLC1A3 | 8, 82 |
| SLC22A1L | 31, 110 |
| SLC22A4 | 160 |
| SLC25A1 | 162 |
| SLC25A13 | 88 |
| SLC26A3 | 51 |
| SLC26A4 | 60, 173 |
| SLC2A1 | 8, 31, 51, 133, 105, 110, 132, 64, 65, 92 |
| SLC2A10 | 64, 132 |
| SLC2A2 | 64, 105, 110, 132, 134 |
| SLC2A3 | 8, 31, 92, 110, 133 |
| SLC2A4 | 31, 64, 85, 134, 105, 106, 132 |
| SLC2A5 | 31 |
| SLC3A2 | 51 |
| SLC4A1 | 8, 86, 114, 158 |
| SLC4A4 | 158 |
| SLC5A5 | 31 |
| SLC5A7 | 8 |
| SLC6A1 | 162 |
| SLC6A14 | 134 |
| SLC6A2 | 12, 23, 29, 62, 162 |
| SLC6A3 | 23, 29, 144, 162 |
| SLC6A4 | 8, 13, 23, 162, 120, 144, 153, 62, 70, 98, 24, 29, 53 |
| SLC7A5 | 51 |
| SLC9A1 | 65, 98, 109 |
| SLEB1 | 111 |
| SLEB3 | 111 |
| SLEB4 | 111 |
| SLEH1 | 86, 111 |
| SLEN1 | 111 |
| SLEN2 | 111 |
| SLEN3 | 111 |
| SLEV1 | 111 |
| SLPI | 18, 58, 76, 177, 92, 110, 133 |
| SMAP1 | 16 |
| SMARCA3 | 51, 83 |
| SMARCA4 | 31, 110, 154 |
| SMARCB1 | 157 |
| SMN1 | 10 |
| SMN2 | 10 |
| SMO | 27, 166 |
| SMS | 31, 109 |
| SNAI1 | 31, 118 |
| SNAP25 | 8, 23, 29, 62, 162 |
| SNCA | 8, 61, 70, 144 |
| SNCAIP | 144 |
| SNCB | 8, 31, 144 |
| SNCG | 8, 10, 31, 144 |
| SNRPB | 111, 118 |
| SNRPN | 111 |
| SOAT1 | 134 |
| SOCS3 | 56, 109, 112, 160 |
| SOD1 | 8, 10, 31, 132, 51, 64, 105 |
| SOD2 | 8, 10, 31, 110, 144, 51, 64, 105 |
| SOD3 | 10 |
| SORD | 37 |
| SOX13 | 64, 105 |
| SOX4 | 31 |
| SP1 | 31, 110 |
| SP100 | 47, 91 |
| SP3 | 123 |
| SPA17 | 122 |
| SPARC | 31, 51, 69, 157, 83, 118, 154 |
| SPARCL1 | 133 |
| SPDEF | 31, 154 |
| SPG7 | 31, 51, 90 |
| SPINK1 | 141 |
| SPINK5 | 18, 20 |
| SPINT1 | 31, 51, 90 |
| SPINT2 | 110 |
| SPN | 8, 51, 92, 110 |
| SPRR1B | 110 |
| SPRR3 | 83 |
| SQSTM1 | 31, 139 |
| SRA1 | 31 |
| SRC | 25, 31, 51, 109, 112, 180 |
| SRD5A2 | 31, 154 |
| SREBF1 | 64, 92, 132, 134 |
| SREBF2 | 51, 95, 134, 154 |
| SRF | 31 |
| SRI | 112 |
| SRP19 | 152 |
| SRPX | 51, 110 |
| SRY | 179 |
| SS18 | 154, 157 |
| SSA1 | 111, 133, 160 |
| SSA2 | 111 |
| SSB | 111 |
| SST | 8, 64, 105, 132 |
| SSTR1 | 31 |
| SSTR4 | 154 |
| SSTR5 | 29, 31, 51, 150, 154 |
| SSX2 | 30, 31, 51, 157, 112, 118, 154, 79, 90, 110 |
| ST14 | 31, 51 |
| ST7 | 24, 31, 51, 83, 90 |
| ST8 | 138 |
| STARD3 | 31, 83 |
| STAT1 | 31, 51, 92, 123, 125, 94, 109, 112 |
| STAT2 | 31, 109, 118 |
| STAT5A | 92 |
| STAT5B | 92, 109 |
| STAT6 | 18, 31, 160 |
| STC1 | 31 |
| STE | 31 |
| STK11 | 118, 140 |
| STMN1 | 8, 31, 110 |
| STRC | 60 |
| STS | 31 |
| SUCLA2 | 164 |
| SULT1A1 | 31 |
| SULT2A1 | 57 |
| SULT2B1 | 31 |
| SUSP1 | 112 |
| SYBL1 | 29 |
| SYCP1 | 31, 110, 112, 157 |
| SYK | 31, 109 |
| SYN1 | 8, 162 |
| SYN2 | 8, 162 |
| SYN3 | 162 |
| SYP | 8, 10, 29, 61, 144, 162 |
| TAC1 | 8, 31, 64, 92, 110, 167 |
| TACC1 | 31 |
| TACC3 | 122 |

TABLE 9-continued

RELATION OF TARGET GENES TO DISEASE

| Gene Name | Disease Code |
| --- | --- |
| TACR1 | 18, 56, 92, 160, 103, 120, 141 |
| TACR2 | 56, 103, 160, 180 |
| TAGLN | 31 |
| TAL1 | 109, 112 |
| TAL2 | 109 |
| TALDO1 | 123 |
| TAM | 70 |
| TAP1 | 31, 64, 105, 167, 174, 110, 123, 133 |
| TAT | 47, 88, 90 |
| TAZ | 99, 129 |
| TBX2 | 31 |
| TBX22 | 49 |
| TBXA2R | 18, 110, 133 |
| TBXAS1 | 98 |
| TCAP | 129 |
| TCF1 | 64, 90, 105, 132, 157 |
| TCF2 | 26, 64, 107, 132 |
| TCF4 | 29, 162 |
| TCF7 | 51, 64, 105, 112 |
| TCL1A | 4, 109, 112 |
| TCL1B | 112 |
| TCL4 | 112 |
| TCL6 | 109 |
| TCO | 173 |
| TCP1 | 70 |
| TCPT | 171 |
| TCRA | 112 |
| TCTA | 109, 167 |
| TDGF1 | 31, 42, 51, 133, 141 |
| TECTA | 60 |
| TEK | 4, 31, 90, 166, 110, 118, 133 |
| TERC | 16 |
| TERF1 | 31, 109 |
| TERT | 31, 51, 110, 133 |
| TF | 8, 110, 123, 167 |
| TFAM | 88, 129 |
| TFAP2A | 51, 118, 154, 166 |
| TFAP2C | 31, 79 |
| TFCP2 | 8, 92 |
| TFE3 | 157 |
| TFF2 | 26, 31, 145 |
| TFF3 | 51 |
| TFG | 112 |
| TFPI | 64, 105 |
| TFRC | 8, 31, 51, 110, 123, 133, 64, 92, 105 |
| TG | 64, 92, 105, 123 |
| TGFB2 | 8, 31, 51, 110, 114, 123 |
| TGFB3 | 31, 51, 110 |
| TGFBI | 83 |
| TGFBR2 | 30, 31, 42, 176, 151, 154, 167, 90, 110, 133, 51, 79, 83 |
| TGFBR3 | 31 |
| TGIF | 83 |
| TGM1 | 8, 133 |
| TGM2 | 8, 31, 110, 133 |
| TGM3 | 83 |
| TGM4 | 154 |
| TH | 23, 24, 29, 134, 144, 162 |
| THBD | 31, 47, 51, 127, 132, 167, 110, 118, 123, 64, 92, 105 |
| THBS2 | 31, 42, 51, 133, 83, 110, 127 |
| THBS4 | 127 |
| THC2 | 171 |
| THPO | 31, 110 |
| THRA | 150, 157 |
| THRB | 31, 133, 150, 154, 157, 167 |
| THRSP | 31 |
| THY1 | 109, 160 |
| TIA1 | 51, 92, 109 |
| TIAM1 | 31, 70, 157 |
| TIE | 4, 31, 109, 118, 157, 166 |
| TIEG | 31, 154 |
| TIF1 | 173 |
| TIF1G | 173 |
| TIMM8A | 60 |
| TIMP2 | 31, 51, 110, 118 |
| TIMP4 | 31 |
| TIP47 | 42 |
| TITF1 | 36, 110, 167 |
| TJP1 | 31, 74, 77, 92, 140, 155 |
| TJP2 | 31, 51, 154 |
| TK1 | 31, 51 |
| TK2 | 129 |
| TKT | 8 |
| TLX1 | 109 |
| TLX3 | 109 |
| TM4SF2 | 109 |
| TMC1 | 60 |
| TMEFF2 | 30, 51, 154 |
| TMIE | 60 |
| TMPRSS2 | 154 |
| TMPRSS3 | 60 |
| TMSB10 | 31, 51, 83, 154, 157 |
| TNC | 31, 51, 79, 154, 180, 98, 110, 118 |
| TNDM | 64 |
| TNF | 31, 35, 42, 133, 167, 110, 112, 114, 51, 79, 109 |
| TNFRSF10A | 31, 51, 110, 112 |
| TNFRSF10C | 51, 83, 110 |
| TNFRSF10D | 110 |
| TNFRSF11A | 139 |
| TNFRSF11B | 139 |
| TNFRSF1B | 31, 51, 64, 123, 134, 98, 105, 110, 92, 95, 97 |
| TNFRSF5 | 8, 31, 35, 123, 133, 180, 92, 110, 112, 42, 56, 75 |
| TNFRSF7 | 75, 92, 109, 123, 157, 111, 112, 118 |
| TNFRSF8 | 92, 123 |
| TNFRSF9 | 110, 160 |
| TNFSF10 | 31, 51, 92, 133, 110, 122, 123 |
| TNFSF11 | 31, 109, 112, 122, 154, 156 |
| TNFSF12 | 111 |
| TNFSF6 | 8, 26, 30, 123, 133, 92, 110, 111, 31, 51, 83 |
| TNFSF7 | 92, 109, 112, 122 |
| TNNC1 | 129 |
| TNNI3 | 129 |
| TNNT1 | 129 |
| TNNT2 | 129 |
| TNRC11 | 162 |
| TOC | 83 |
| TOP1 | 31, 51, 109, 110, 133 |
| TOP2B | 110, 167 |
| TP53 | 3, 4, 8, 167, 173, 123, 133, 140, 92, 110, 112, 31, 51, 90 |
| TP73 | 31, 35, 51, 110, 112, 118, 59, 90, 109 |
| TP73L | 26, 27, 30, 110, 83, 48, 166, 42, 51 |
| TPD52 | 31 |
| TPH1 | 29, 62, 162 |
| TPI1 | 86 |
| TPK1 | 117 |
| TPM1 | 100, 129, 154 |
| TPM2 | 31, 110, 129 |
| TPM3 | 112, 129 |
| TPO | 60, 61, 102, 174 |
| TPT1 | 8, 18, 51, 70 |
| TPX2 | 110 |
| TRA1 | 8, 21, 51, 88, 90 |
| TRAF1 | 75, 93, 109, 112 |
| TRAF4 | 31 |
| TRAPPC1 | 118 |
| TRBV5-3 | 92 |
| TRC8 | 157 |
| TRDD3 | 109, 123 |
| TRDV3 | 38, 92, 109, 157 |
| TREM2 | 61 |
| TRGV9 | 92, 114, 160, 166 |
| TRHR | 8, 150, 162 |
| TRIP11 | 109 |
| TRPM1 | 118 |
| TRPV6 | 154 |
| TSC1 | 30, 82, 110, 157 |
| TSG101 | 31, 42, 79, 154, 90, 92, 109 |
| TSG11 | 110 |
| TSLP | 20 |
| TSN | 109 |
| TSP50 | 31 |
| TSPY | 154 |

TABLE 9-continued

RELATION OF TARGET GENES TO DISEASE

| Gene Name | Disease Code |
|---|---|
| TSPYQ1 | 102 |
| TTC3 | 70 |
| TTC4 | 31, 118 |
| TTN | 100, 124, 129 |
| TTR | 8, 9, 64, 105 |
| TU3A | 157 |
| TUB | 134 |
| TUBB2 | 154 |
| TULP1 | 79 |
| TXN | 31, 90, 92, 109, 133, 160 |
| TXNRD3 | 90 |
| TYMS | 31, 51, 59, 133, 109, 110, 112 |
| TYRO3 | 122 |
| TYROBP | 61 |
| TYRP1 | 118 |
| UAN | 131 |
| UBB | 8, 70 |
| UBC | 157 |
| UBE1L | 110 |
| UBE2B | 102 |
| UBE2I | 110 |
| UBE3A | 24 |
| UBM2 | 118 |
| UBTF | 90, 111, 160 |
| UCHL1 | 36, 51, 110, 133, 144, 167 |
| UCN | 64, 134, 150 |
| UCP1 | 134 |
| UCP2 | 64, 132, 134 |
| UCP3 | 64, 106, 132, 134 |
| UFD1L | 162 |
| UGCG | 92 |
| UGT1A1 | 28, 31 |
| UGT2B15 | 154 |
| UMOD | 122, 157 |
| UMPK | 51 |
| UPK1A | 74 |
| UPK1B | 30, 176 |
| UPK2 | 30, 176 |
| UPK3A | 30, 139, 176 |
| UPP1 | 31, 51 |
| USF1 | 31 |
| USF2 | 31 |
| USH1C | 60 |
| USH3A | 60 |
| USP4 | 110, 167 |
| USP9Y | 102 |
| UVM1 | 118 |
| VCAM1 | 4, 31, 51, 112, 123, 132, 64, 92, 105 |
| VCL | 31, 51 |
| VCY2 | 102 |
| VDR | 4, 31, 51, 154, 123, 132, 136, 64, 105, 109 |
| VEGFC | 31, 42, 83, 157, 110, 133, 154 |
| VHL | 157 |
| VIL1 | 45 |
| VIL2 | 79, 160 |
| VIM | 8, 31, 51, 110, 167 |
| VIP | 4, 8, 51, 110, 167, 133 |
| VIPR1 | 92, 133, 154, 167 |
| VIPR2 | 154 |
| VLDLR | 8, 31, 61 |
| VMD2 | 113 |
| VSNL1 | 8, 162 |
| VSPA | 179 |
| VTN | 8, 51 |
| VWF | 31, 53, 64, 132, 92, 103, 105 |
| WAS | 171 |
| WDM | 129 |
| WEE1 | 47, 92 |
| WFS1 | 29, 64, 105 |
| WHN | 6 |
| WHSC1 | 9, 122 |
| WHSC1L1 | 31, 109 |
| WHSC2 | 92 |
| WISP1 | 31, 51 |
| WISP2 | 31, 51 |
| WISP3 | 31, 51 |
| WIT-1 | 109 |
| WNT1 | 27, 31 |
| WNT10B | 31 |
| WNT2 | 24, 31, 51, 69, 83 |
| WNT3 | 31, 110 |
| WNT3A | 122 |
| WNT7A | 79, 110 |
| WNT7B | 30, 31, 83, 110 |
| WNT8B | 82 |
| WRB | 70 |
| WRN | 127 |
| WSN | 144 |
| WT1 | 31, 110, 133 |
| WTS | 134 |
| WWOX | 31, 83, 122 |
| XBP1 | 29 |
| XCL1 | 56, 92 |
| XK | 29 |
| XLKD1 | 31, 47 |
| XPA | 51, 110 |
| XPC | 24, 166 |
| XRCC1 | 27, 31, 51, 83, 110, 166 |
| XRCC2 | 31 |
| XRCC3 | 30, 31, 118 |
| XRCC5 | 31, 42, 51, 109, 122 |
| YES1 | 51, 83, 118 |
| YWHAG | 118 |
| YWHAH | 162 |
| YY1 | 92, 109 |
| ZAP70 | 92, 118 |
| ZFY | 154 |
| ZIC2 | 110, 167 |
| ZNF145 | 109 |
| ZNF147 | 31 |
| ZNF151 | 51 |
| ZNF198 | 112 |
| ZNF217 | 31, 51, 154 |
| ZNFN1A1 | 109, 112 |
| ZNFN1A2 | 109 |
| ZXDA | 179 |
| ZXDB | 179 |

The invention claimed is:

1. A nucleic acid selected from the group consisting of:
   (a) a nucleic acid consisting of the nucleotide sequence set forth in SEQ ID NO: 4;
   (b) a RNA encoded by the nucleic acid of (a), wherein the RNA is identical in length to (a);
   (c) a nucleic acid at least 90% identical to (a) or (b); and
   (d) the complement of one of the nucleic acids of (a)-(c), wherein the complement is identical in length to the one of the nucleic acids of (a)-(c);
   wherein the nucleic acid contains a non-naturally occurring nucleotide or ribonucleotide.

2. A probe comprising a heterologous nucleic acid, wherein the heterologous nucleic acid consists of a nucleic acid sequence selected from the group consisting of:
   (a) the sequence set forth in SEQ ID NO: 4;
   (b) a RNA sequence encoded by the sequence of (a), wherein the RNA sequence is identical in length to (a);
   (c) a sequence at least 90% identical to (a) or (b); and
   (d) the complement of one of the sequences of (a)-(c), wherein the complement is identical in length to the one of the sequences of (a)-(c),
   wherein the probe comprises at least one of a non-naturally occurring nucleotide or ribonucleotide, a label, and a solid substrate.

3. A vector comprising a heterologous nucleic acid, wherein the heterologous nucleic acid consists of a nucleic acid sequence selected from the group consisting of:
   (a) the sequence set forth in SEQ ID NO: 4;
   (b) a RNA sequence encoded by the sequence of (a), wherein the RNA sequence is identical in length to (a);
   (c) a sequence at least 90% identical to (a) or (b); and
   (d) the complement of one of the sequences of (a)-(c), wherein the complement is identical in length to the one of the sequences of (a)-(c).

* * * * *

SEQUENCE LISTING

<160> NUMBER OF SEQ ID NOS: 66

<210> SEQ ID NO 1
<211> LENGTH: 87
<212> TYPE: DNA
<213> ORGANISM: Homo sapiens

<400> SEQUENCE: 1
tggtgtggtg gggcagctgg tgttgtgaat caggccgttg ccaatcagag aacggctact    60

```
tcacaacacc agggccacac cacacta                                          87

<210> SEQ ID NO 2
<211> LENGTH: 17
<212> TYPE: DNA
<213> ORGANISM: Homo sapiens

<400> SEQUENCE: 2
agctggtgtt gtgaatc                                                     17

<210> SEQ ID NO 3
<211> LENGTH: 22
<212> TYPE: DNA
<213> ORGANISM: Homo sapiens

<400> SEQUENCE: 3
ggctacttca caacaccagg gc                                               22

<210> SEQ ID NO 4
<211> LENGTH: 21
<212> TYPE: DNA
<213> ORGANISM: Homo sapiens

<400> SEQUENCE: 4
gctacttcac aacaccaggg c                                                21

<210> SEQ ID NO 5
<211> LENGTH: 22
<212> TYPE: DNA
<213> ORGANISM: Homo sapiens

<400> SEQUENCE: 5
actctaaaga gaagcgcttt gt                                               22

<210> SEQ ID NO 6
<211> LENGTH: 22
<212> TYPE: DNA
<213> ORGANISM: Homo sapiens

<400> SEQUENCE: 6
acccaccaaa gagaagcact tt                                               22

<210> SEQ ID NO 7
<211> LENGTH: 21
<212> TYPE: DNA
<213> ORGANISM: Homo sapiens

<400> SEQUENCE: 7
gtccctgtac tggaacttga g                                                21

<210> SEQ ID NO 8
<211> LENGTH: 21
<212> TYPE: DNA
<213> ORGANISM: Homo sapiens

<400> SEQUENCE: 8
gtgtccctgt actggaacgc a                                                21

<210> SEQ ID NO 9
<211> LENGTH: 20
<212> TYPE: DNA
<213> ORGANISM: Homo sapiens
```

```
<400> SEQUENCE: 9
gcctggccat gtcagctacg                                              20

<210> SEQ ID NO 10
<211> LENGTH: 21
<212> TYPE: DNA
<213> ORGANISM: Homo sapiens

<400> SEQUENCE: 10
ttgatgggag gctagtgttt c                                            21

<210> SEQ ID NO 11
<211> LENGTH: 21
<212> TYPE: DNA
<213> ORGANISM: Homo sapiens

<400> SEQUENCE: 11
gacgtggagg cgttcttagt c                                            21

<210> SEQ ID NO 12
<211> LENGTH: 20
<212> TYPE: DNA
<213> ORGANISM: Homo sapiens

<400> SEQUENCE: 12
tgacaaccgt tggggattac                                              20

<210> SEQ ID NO 13
<211> LENGTH: 85
<212> TYPE: DNA
<213> ORGANISM: Homo sapiens

<400> SEQUENCE: 13
gctcaggctg tgatttcaag ccaggggggcg ttttctata actggatgaa aagcacctcc  60
agagcttgaa gctcacagtt tgaga                                        85

<210> SEQ ID NO 14
<211> LENGTH: 87
<212> TYPE: DNA
<213> ORGANISM: Homo sapiens

<400> SEQUENCE: 14
tctcctgctg tgaccctcaa gatggaagca gtttctgttg tctgaaagga agaaagtgc   60 ttccttttg agggttactg tttgaga                                       87

<210> SEQ ID NO 15
<211> LENGTH: 83
<212> TYPE: DNA
<213> ORGANISM: Homo sapiens

<400> SEQUENCE: 15
tctcatgcag tcattctcca aaagaaagca ctttctgttg tctgaaagca gagtgccttc  60
ttttggagcg ttactgtttg aga                                          83

<210> SEQ ID NO 16
<211> LENGTH: 84
<212> TYPE: DNA
<213> ORGANISM: Homo sapiens

<400> SEQUENCE: 16
tctcatgcag tcattctcca aagggagca ctttctgttt gaagaaaac aaagtgcctc    60
```

```
cttttagagt gttactgttt gaga                                             84
```

<210> SEQ ID NO 17
<211> LENGTH: 87
<212> TYPE: DNA
<213> ORGANISM: Homo sapiens

<400> SEQUENCE: 17

```
tctcaggctg tgaccctcta aagggaagcg ctttctgtgg tcagaaagaa aagcaagtgc      60
ttccttttag agggttaccg tttggga                                          87
```

<210> SEQ ID NO 18
<211> LENGTH: 83
<212> TYPE: DNA
<213> ORGANISM: Homo sapiens

<400> SEQUENCE: 18

```
tctcatgcag tcattctcca aagaaagca ctttctgttg tctgaaagca gagtgccttc       60
ttttggagcg ttactgtttg aga                                              83
```

<210> SEQ ID NO 19
<211> LENGTH: 87
<212> TYPE: DNA
<213> ORGANISM: Homo sapiens

<400> SEQUENCE: 19

```
tctcagcctg tgaccctcta gagggaagcg ctttctgttg tctgaaagaa aagaaagtgc      60 atcttttag aggattacag tttgaga                                           87
```

<210> SEQ ID NO 20
<211> LENGTH: 87
<212> TYPE: DNA
<213> ORGANISM: Homo sapiens

<400> SEQUENCE: 20

```
tctcaagcta tgagtctaca aaggaaagcg ctttctgttg tcagaaagaa gagaaagcgc      60
ttcccttttg agggttacgg tttgaga                                          87
```

<210> SEQ ID NO 21
<211> LENGTH: 85
<212> TYPE: DNA
<213> ORGANISM: Homo sapiens

<400> SEQUENCE: 21

```
ctcaggctgt gaccctccag agggaagtac tttctgttgt ctgagagaaa agaaagtgct      60 tcccttttgga ctgtttcggt ttgag                                           85
```

<210> SEQ ID NO 22
<211> LENGTH: 81
<212> TYPE: DNA
<213> ORGANISM: Homo sapiens

<400> SEQUENCE: 22

```
caggctgtga ccctcttgag ggaagcactt tctgttgtct gaaagaagag aaagtgcttc      60
cttttagagg cttactgtct g                                                81
```

<210> SEQ ID NO 23
<211> LENGTH: 67
<212> TYPE: DNA

<213> ORGANISM: Homo sapiens

<400> SEQUENCE: 23
tgaccctcta gagggaagcg ctttctgttg tctgaaagaa aagaaagtgc atccttttag    60
aggttta    67

<210> SEQ ID NO 24
<211> LENGTH: 85
<212> TYPE: DNA
<213> ORGANISM: Homo sapiens

<400> SEQUENCE: 24
ctcaagctgt gactctccag agggatgcac tttctcttat gtgaaaaaaa agaaggcgct    60
tccctttaga gcgttacggt ttggg    85

<210> SEQ ID NO 25
<211> LENGTH: 87
<212> TYPE: DNA
<213> ORGANISM: Homo sapiens

<400> SEQUENCE: 25
tctcatgctg tgaccctcta gagggaagcg ctttctgttg tctgaaagaa aagaacgcgc    60
ttccctatag agggttaccc tttgaga    87

<210> SEQ ID NO 26
<211> LENGTH: 87
<212> TYPE: DNA
<213> ORGANISM: Homo sapiens

<400> SEQUENCE: 26
tctcatgctg tgaccctcta gagggaagca ctttctcttg tctaaaagaa aagaaagcgc    60 ttctcttag aggattactc tttgaga    87

<210> SEQ ID NO 27
<211> LENGTH: 61
<212> TYPE: DNA
<213> ORGANISM: Homo sapiens

<400> SEQUENCE: 27
ccctctacag ggaagcgctt tctgttgtct gaaagaaaag aaagtgcttc cttttagagg    60
g    61

<210> SEQ ID NO 28
<211> LENGTH: 83
<212> TYPE: DNA
<213> ORGANISM: Homo sapiens

<400> SEQUENCE: 28
tcatgctgtg ccctccaga gggaagcgct ttctgttgtc tgaaagaaaa caaagcgctc    60
ccctttagag gtttacggtt tga    83

<210> SEQ ID NO 29
<211> LENGTH: 85
<212> TYPE: DNA
<213> ORGANISM: Homo sapiens

<400> SEQUENCE: 29
ctcaggctgt gaccctctag agggaagcac tttctgttgc ttgaaagaag agaaagcgct    60
tccttttaga ggattactct ttgag    85

```
<210> SEQ ID NO 30
<211> LENGTH: 87
<212> TYPE: DNA
<213> ORGANISM: Homo sapiens

<400> SEQUENCE: 30
tctcaggctg tcgtcctcta gagggaagca ctttctgttg tctgaaagaa aagaaagtgc      60
ttccttttag agggttaccg tttgaga                                          87

<210> SEQ ID NO 31
<211> LENGTH: 87
<212> TYPE: DNA
<213> ORGANISM: Homo sapiens

<400> SEQUENCE: 31
tctcatgctg tgactctctg gagggaagca ctttctgttg tctgaaagaa aacaaagcgc      60 ttctcttttag agtgttacgg tttgaga                                         87

<210> SEQ ID NO 32
<211> LENGTH: 87
<212> TYPE: DNA
<213> ORGANISM: Homo sapiens

<400> SEQUENCE: 32
tctcatgctg tgaccctaca aagggaagca ctttctcttg tccaaaggaa aagaaggcgc      60 ttcccttttgg agtgttacgg tttgaga                                         87

<210> SEQ ID NO 33
<211> LENGTH: 87
<212> TYPE: DNA
<213> ORGANISM: Homo sapiens

<400> SEQUENCE: 33
tctcaggcag tgaccctcta gatggaagca ctgtctgttg tataaaagaa aagatcgtgc      60 atcccttttag agtgttactg tttgaga                                         87

<210> SEQ ID NO 34
<211> LENGTH: 88
<212> TYPE: DNA
<213> ORGANISM: Homo sapiens

<400> SEQUENCE: 34
tcccatgctg tgaccctcca aagggaagcg ctttctgttt gttttctctt aaacaaagtg      60
cctcccttta gagtgttacc gtttggga                                         88

<210> SEQ ID NO 35
<211> LENGTH: 87
<212> TYPE: DNA
<213> ORGANISM: Homo sapiens

<400> SEQUENCE: 35
tctcgggctg tgactctcca aagggaagaa ttttctcttg tctaaaagaa aagaacgcac      60 ttcccttttag agtgttaccg tgtgaga                                         87

<210> SEQ ID NO 36
<211> LENGTH: 87
<212> TYPE: DNA
```

<400> SEQUENCE: 36
tctcaagctg tgagtctaca aagggaagcc ctttctgttg tctaaaagaa aagaaagtgc     60
ttctctttgg tgggttacgg tttgaga                                         87

<210> SEQ ID NO 37
<211> LENGTH: 67
<212> TYPE: DNA
<213> ORGANISM: Homo sapiens

<400> SEQUENCE: 37
gtgaccctct agatggaagc actgtctgtt gtctaagaaa agatcgtgca tcccttaga      60 gtgttac                                                               67

<210> SEQ ID NO 38
<211> LENGTH: 90
<212> TYPE: DNA
<213> ORGANISM: Homo sapiens

<400> SEQUENCE: 38
tcccatgctg tgaccctcta gaggaagcac tttctgtttg ttgtctgaga aaaaacaaag     60 tgcttcccctt tagagtgtta ccgtttggga                                     90

<210> SEQ ID NO 39
<211> LENGTH: 85
<212> TYPE: DNA
<213> ORGANISM: Homo sapiens

<400> SEQUENCE: 39
tctcatgatg tgaccatctg gaggtaagaa gcactttgtg ttttgtgaaa gaaagtgctt     60
cctttcagag ggttactctt tgaga                                           85

<210> SEQ ID NO 40
<211> LENGTH: 83
<212> TYPE: DNA
<213> ORGANISM: Homo sapiens

<400> SEQUENCE: 40
tctcgtgctg tgaccctcta gagggaagca ctttctgttg aaagaaaaga acatgcatcc     60
tttcagaggg ttactctttg aga                                             83

<210> SEQ ID NO 41
<211> LENGTH: 88
<212> TYPE: DNA
<213> ORGANISM: Homo sapiens

<400> SEQUENCE: 41
tctcaggctg tgaccctcta gagggaagcg ctttctgttg gctaaaagaa aagaaagcgc     60
ttcccttcag agtgttaacg ctttgaga                                        88

<210> SEQ ID NO 42
<211> LENGTH: 85
<212> TYPE: DNA
<213> ORGANISM: Homo sapiens

<400> SEQUENCE: 42
tctcaagctg tgactgcaaa gggaagccct ttctgttgtc tgaaagaaga gaaagcgctt     60
ccctttgctg gattacggtt tgaga                                           85

```
<210> SEQ ID NO 43
<211> LENGTH: 87
<212> TYPE: DNA
<213> ORGANISM: Homo sapiens

<400> SEQUENCE: 43
tcccatgctg tgaccctcta gagggaagca ctttctgttg tctgaaagaa accaaagcgc    60 ttcccttttgg agcgttacgg tttgaga                                       87

<210> SEQ ID NO 44
<211> LENGTH: 90
<212> TYPE: DNA
<213> ORGANISM: Homo sapiens

<400> SEQUENCE: 44
tctcaggctg tgaccatctg gaggtaagaa gcactttctg ttttgtgaaa gaaaagaaag    60
tgcttccttt cagagggtta ctctttgaga                                     90

<210> SEQ ID NO 45
<211> LENGTH: 87
<212> TYPE: DNA
<213> ORGANISM: Homo sapiens

<400> SEQUENCE: 45
tctcaagctg tgggtctgca aagggaagcc ctttctgttg tctaaaagaa gagaaagcgc    60 ttcccttttgc tggattacgg tttgaga                                       87

<210> SEQ ID NO 46
<211> LENGTH: 85
<212> TYPE: DNA
<213> ORGANISM: Homo sapiens

<400> SEQUENCE: 46
tctcaggcag tgaccctcta gatggaagca ctgtctgttg tctaagaaaa gatcgtgcat    60
ccttttagag tgttactgtt tgaga                                          85

<210> SEQ ID NO 47
<211> LENGTH: 88
<212> TYPE: DNA
<213> ORGANISM: Homo sapiens

<400> SEQUENCE: 47
tcccatgctg tgaccctcta gaggaagcac tttctgtttg ttgtctgaga aaaacaaag     60 tgcttccctt tagagttact gtttggga                                       88

<210> SEQ ID NO 48
<211> LENGTH: 87
<212> TYPE: DNA
<213> ORGANISM: Homo sapiens

<400> SEQUENCE: 48
tctcaggctg tgaccctcca aagggaagaa ctttctgttg tctaaaagaa aagaacgcac    60 ttcccttttag agtgttaccg tgtgaga                                       87

<210> SEQ ID NO 49
<211> LENGTH: 87
<212> TYPE: DNA
<213> ORGANISM: Homo sapiens

<400> SEQUENCE: 49
```

```
tctcaggctg tgtccctcta gagggaagcg ctttctgttg tctgaaagaa aagaaaatgg      60 ttcccttttag agtgttacgc tttgaga                                         87

<210> SEQ ID NO 50
<211> LENGTH: 85
<212> TYPE: DNA
<213> ORGANISM: Homo sapiens

<400> SEQUENCE: 50
ctcaggctgt gacactctag agggaagcgc tttctgttgt ctgaaagaaa ggaaagtgca      60
tccttttaga gtgttactgt ttgag                                            85

<210> SEQ ID NO 51
<211> LENGTH: 85
<212> TYPE: DNA
<213> ORGANISM: Homo sapiens

<400> SEQUENCE: 51
tctcaagctg tgactgcaaa gggaagccct ttctgttgtc taaaagaaaa gaaagtgctt      60 cccttggtg aattacggtt tgaga                                             85

<210> SEQ ID NO 52
<211> LENGTH: 90
<212> TYPE: DNA
<213> ORGANISM: Homo sapiens

<400> SEQUENCE: 52
tctcaggctg tgaccttctc gaggaaagaa gcactttctg ttgtctgaaa gaaaagaaag      60
tgcttccttt cagagggtta cggtttgaga                                       90

<210> SEQ ID NO 53
<211> LENGTH: 87
<212> TYPE: DNA
<213> ORGANISM: Homo sapiens

<400> SEQUENCE: 53
tctcaagctg tgagtctaca aaggaaagcg ctttctgttg tctgaaagaa aagaaatcgc      60 ttcccttttgg agtgttacgg tttgaga                                         87

<210> SEQ ID NO 54
<211> LENGTH: 90
<212> TYPE: DNA
<213> ORGANISM: Homo sapiens

<400> SEQUENCE: 54
tctcaggttg tgaccttctc gaggaaagaa gcactttctg ttgtctgaaa gaaaagaaag      60
tgcttccttt cagagggtta cggtttgaga                                       90

<210> SEQ ID NO 55
<211> LENGTH: 87
<212> TYPE: DNA
<213> ORGANISM: Homo sapiens

<400> SEQUENCE: 55
tctcaggctg tgtccctcta cagggaagcg ctttctgttg tctgaaagaa aggaaagtgc      60
atccttttag agtgttactg tttgaga                                          87

<210> SEQ ID NO 56
<211> LENGTH: 21
```

-continued

```
<212> TYPE: DNA
<213> ORGANISM: Homo sapiens

<400> SEQUENCE: 56
gtgccgccat cttttgagtg t                                              21

<210> SEQ ID NO 57
<211> LENGTH: 23
<212> TYPE: DNA
<213> ORGANISM: Homo sapiens

<400> SEQUENCE: 57
aaagtgctgc gacatttgag cgt                                            23

<210> SEQ ID NO 58
<211> LENGTH: 23
<212> TYPE: DNA
<213> ORGANISM: Homo sapiens

<400> SEQUENCE: 58
gaagtgcttc gattttgggg tgt                                            23

<210> SEQ ID NO 59
<211> LENGTH: 22
<212> TYPE: DNA
<213> ORGANISM: Homo sapiens
<220> FEATURE:
<221> NAME/KEY: h
<222> LOCATION: (12)..(12)
<223> OTHER INFORMATION: h is a, c or t
<220> FEATURE:
<221> NAME/KEY: k
<222> LOCATION: (20)..(20)
<223> OTHER INFORMATION: k is g or t

<400> SEQUENCE: 59
aaagtgcttc chtttagagk gt                                             22

<210> SEQ ID NO 60
<211> LENGTH: 22
<212> TYPE: DNA
<213> ORGANISM: Homo sapiens

<400> SEQUENCE: 60
actcaaaatg ggggcgcttt cc                                             22

<210> SEQ ID NO 61
<211> LENGTH: 23
<212> TYPE: DNA
<213> ORGANISM: Homo sapiens

<400> SEQUENCE: 61
taagtgcttc catgttttgg tga                                            23

<210> SEQ ID NO 62
<211> LENGTH: 23
<212> TYPE: DNA
<213> ORGANISM: Homo sapiens

<400> SEQUENCE: 62
taagtgcttc catgttttag tag                                            23

<210> SEQ ID NO 63
<211> LENGTH: 23
<212> TYPE: DNA
```

```
<213> ORGANISM: Homo sapiens

<400> SEQUENCE: 63
taagtgcttc catgtttcag tgg                                              23

<210> SEQ ID NO 64
<211> LENGTH: 23
<212> TYPE: DNA
<213> ORGANISM: Homo sapiens

<400> SEQUENCE: 64
taagtgcttc catgtttgag tgt                                              23

<210> SEQ ID NO 65
<211> LENGTH: 22
<212> TYPE: DNA
<213> ORGANISM: Homo sapiens
<220> FEATURE:
<221> NAME/KEY: h
<222> LOCATION: (12)..(12)
<223> OTHER INFORMATION: h is a, c or t
<220> FEATURE:
<221> NAME/KEY: k
<222> LOCATION: (20)..(20)
<223> OTHER INFORMATION: k is g or t

<400> SEQUENCE: 65
aaagtgcttc chtttagagk gt                                               22

<210> SEQ ID NO 66
<211> LENGTH: 19
<212> TYPE: DNA
<213> ORGANISM: Homo sapiens

<400> SEQUENCE: 66
ctctagaggg aagcacttt                                                   19
```